US011806367B2

(12) United States Patent
Cherqui et al.

(10) Patent No.: US 11,806,367 B2
(45) Date of Patent: Nov. 7, 2023

(54) METHODS OF TREATING LYSOSOMAL DISORDERS

(71) Applicant: The Regents of the University of California, Oakland, CA (US)

(72) Inventors: Stephanie Cherqui, La Jolla, CA (US); Eric Adler, La Jolla, CA (US); Sylvia Evans, La Jolla, CA (US)

(73) Assignee: The Regents of the University of California, Oakland, CA (US)

( * ) Notice: Subject to any disclaimer, the term of this patent is extended or adjusted under 35 U.S.C. 154(b) by 973 days.

(21) Appl. No.: 16/493,573

(22) PCT Filed: Mar. 15, 2018

(86) PCT No.: PCT/US2018/022598

§ 371 (c)(1),
(2) Date: Sep. 12, 2019

(87) PCT Pub. No.: WO2018/170239

PCT Pub. Date: Sep. 20, 2018

(65) Prior Publication Data

US 2021/0161966 A1 Jun. 3, 2021

Related U.S. Application Data

(60) Provisional application No. 62/471,741, filed on Mar. 15, 2017, provisional application No. 62/507,713, filed on May 17, 2017.

(51) Int. Cl.

*A61K 35/28* (2015.01)
*A61K 35/14* (2015.01)
*C07K 14/705* (2006.01)
*C12N 15/86* (2006.01)
*A61P 3/00* (2006.01)
*A61K 38/00* (2006.01)
*A61K 48/00* (2006.01)

(52) U.S. Cl.

CPC .............. *A61K 35/28* (2013.01); *A61K 35/14* (2013.01); *A61P 3/00* (2018.01); *C07K 14/705* (2013.01); *C12N 15/86* (2013.01); *A61K 38/00* (2013.01); *A61K 48/00* (2013.01); *C12N 2740/15043* (2013.01)

(58) Field of Classification Search

None

See application file for complete search history.

(56) References Cited

U.S. PATENT DOCUMENTS

| | | | |
|---|---|---|---|
| 2015/0224209 A1 | 8/2015 | Kohn et al. | |
| 2016/0271181 A1 | 9/2016 | Case et al. | |
| 2019/0062385 A1 | 2/2019 | Drivas et al. | |

FOREIGN PATENT DOCUMENTS

| | | | |
|---|---|---|---|
| CN | 106459995 | A | 2/2017 |
| WO | WO-2014/011237 | A1 | 1/2014 |
| WO | WO-2015/070083 | A1 | 5/2015 |
| WO | 2017/015245 | A1 | 1/2017 |
| WO | WO-2017/003795 | A1 | 1/2017 |
| WO | WO-2018/170239 | A1 | 9/2018 |

OTHER PUBLICATIONS

Nishino, et al. (2000) "Primary LAMP-2 deficiency causes X-linked vacuolar cardiomyopathy and myopathy (Danon disease)", Nature, 406(8): 906-10. (Year: 2000).*

Oilonomopoulos, et al. (2018) "Pluripotent Stem Cell-Derived Cardiomyocytes as a Platform for Cell Therapy Applications: Progress and Hurdles for Clinical Translation", Molecular Therapy, 26(7): 1624-34. (Year: 2018).*

Dighe, et al. (2014) "Long-Term Reproducible Expression in Human Fetal Liver Hematopoietic Stem Cells with a UCOE-Based Lentiviral Vector", PLoS ONE, 9(8): 3104805, 8 pages. (Year: 2014).*

Wang, et al. (2018) "A Combined In Vivo HSC Transduction/Selection Approach Results in Efficient and Stable Gene Expression in Peripheral Blood Cells in Mice", Molecular Therapy: Methods & Clinical Development, 8: 52-64. (Year: 2018).*

Yeagy, et al., "Lentiviral Vector-Transduced Hematopoietic Stem Cell Gene Therapy for Cystinosis", Molecular Therapy, 2010, vol. 18, Supplement 1, pp. S157-S158.

Cox, Timothy M. "Innovative Treatments of Lysosomal Diseases," Best Practice & Research Clinical Endocrinology & Metabolism, 29 (2015), pp. 275-311.

Extended European Search Report dated Dec. 7, 2020, from application No. 18766923.9.

Case et al. "Stable transduction of quiescent CD34+CD38-human hematopoietic cells by HIV-1-based lentiviral ectors," Proc. Natl. Acad. Sci. USA, Mar. 1999, 96:2988-2993.

Cherqui, Stephanie. "Cysteamine therapy: a treatment for cystinosis, not a cure," Kidney International, 2012, 81:127-129.

Chevronnay et al. "Hematopoietic Stem Cells Transplantation Can Normalize Thyroid Function in a Cystinosis Mouse Model," Endocrinology, Apr. 2016, 157(4):1363-1371.

Chiaverini et al. "In vivo reflectance confocal microscopy of the skin: A noninvasive means of assessing body cystine accumulation in infantile cystinosis," J Am Acad Dermatol, Apr. 2013, 68(4):e111-e116.

Cutler et al. "Extended follow-up of methotrexate-free immunosuppression using sirolimus and tacrolimus in related and unrelated donor peripheral blood stem cell transplantation," Blood, Apr. 1, 2007, 109(7):3108-3114.

Geyer et al. "A comparison of immune reconstitution and graft-versus-host disease following myeloablative conditioning (MAC) vs. reduced toxicity conditioning (RTC) and umbilical cord blood transplantation (UCBT) in paediatric recipients," Br J Haematol, Oct. 2011, 155(2):218-234.

(Continued)

*Primary Examiner* — Robert M Kelly

(74) *Attorney, Agent, or Firm* — Foley & Lardner LLP

(57) ABSTRACT

Provided herein are methods for treating a lysosomal transmembrane protein disease or disorder through ex vivo introduction of a nucleic acid molecule into hematopoietic stem and progenitor cells (HSPCs) followed by transplantation of the HSPCs into a subject in need of treatment. Also provided are vectors containing the nucleic acid molecule.

10 Claims, 10 Drawing Sheets

Specification includes a Sequence Listing.

(56) References Cited

OTHER PUBLICATIONS

Harrison et al. "Hematopoietic Stem Cell Gene Therapy for the Multisystemic Lysosomal Storage Disorder Cystinosis," Molecular Therapy, Feb. 2013, 21(2):433-444.
Naphade et al. "Brief Reports: Lysosomal Cross-Correction by Hematopoietic Stem Cell-Derived Macrophages Via Tunneling Nanotubes," Stem Cells, 2015, 33:301-309.
Rocca et al. "Treatment of Inherited Eye Defects by Systemic Hematopoietic Stem Cell Transplantation," Invest Ophthalmol Vis Sci, Nov. 2015, 56(12):7214-7223.
Ruivo et al. "Molecular and cellular basis of lysosomal transmembrane protein dysfunction," Biochimica et Biophysica Acta, 2009, 1793:636-649.
Schleuning et al. "Calcineurin inhibitor-free GVHD prophylaxis with sirolimus, mycophenolate mofetil and ATG in Allo-SCT for leukemia patients with high relapse risk: an observational cohort study," Bone Marrow Transplantation, 2009, 43:717-723.
Yeagy et al. "Kidney preservation by bone marrow cell transplantation in hereditary nephropathy," Kidney International, 2011, 79:1198-1206.
PCT/US2018/022598 International Search Report and Written Opinion dated Jul. 26, 2018.
Besouw et al. "The origin of halitosis in cystinotic patients due to cysteamine treatment," Molecular Genetics and Metabolism, 2007, 91:228-233.
Simpson et al. "Quantitative in vivo and ex vivo confocal microscopy analysis of comeal cystine crystals in the Ctns−/−knockout mouse," Molecular Vision, 2011, 17:2212-2220.
Perez et al., "LAMP-2C inhibts MHC class II presentation of cytoplasmic antigens by disrupting chaperone-mediated autophagy", J Immunol., Mar. 15, 2016, 196(6), pp. 2457-2465.
Zhou et al., "Lamp-2a Facilitates MHC Class II Presentation of Cytoplasmic Antigens", Immunity, May 2005, vol. 22, pp. 571-581.

* cited by examiner

Ctns$^{-/-}$ mice

Treated Ctns$^{-/-}$ mice

Ctns$^{-/-}$ mice

Treated Ctns$^{-/-}$ mice

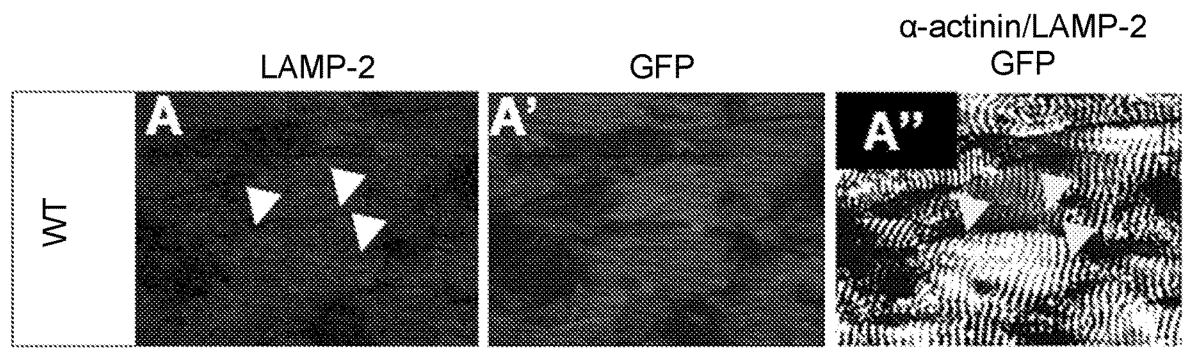
FIG. 10A
LAMP-2
GFP
α-actinin/LAMP-2
GFP
LAMP-2 KO
B
B'
B''
FIG. 10B
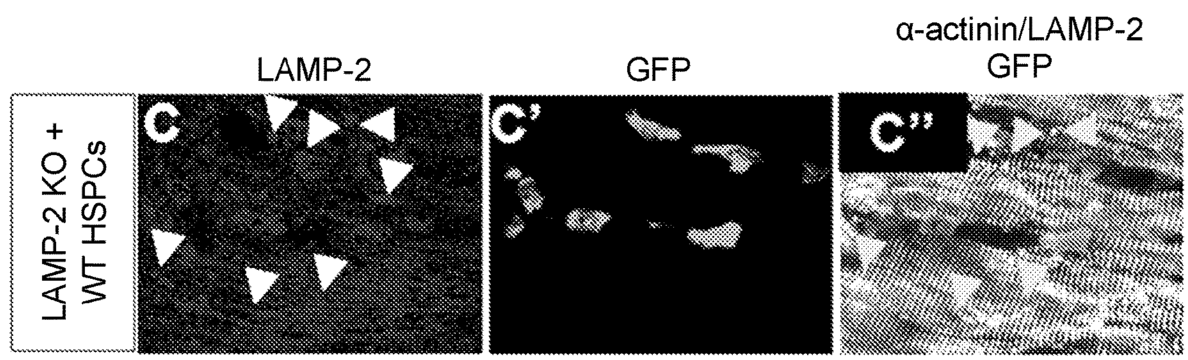
FIG. 10C

SEQUENCE LISTING

<160> NUMBER OF SEQ ID NOS: 27

<210> SEQ ID NO 1
<211> LENGTH: 367
<212> TYPE: PRT
<213> ORGANISM: homo sapiens

<400> SEQUENCE: 1

Met Ile Arg Asn Trp Leu Thr Ile Phe Ile Leu Phe Pro Leu Lys Leu
1 5 10 15

Val Glu Lys Cys Glu Ser Ser Val Ser Leu Thr Val Pro Pro Val Val
20 25 30

Lys Leu Glu Asn Gly Ser Ser Thr Asn Val Ser Leu Thr Leu Arg Pro
35 40 45

Pro Leu Asn Ala Thr Leu Val Ile Thr Phe Glu Ile Thr Phe Arg Ser
50 55 60

Lys Asn Ile Thr Ile Leu Glu Leu Pro Asp Glu Val Val Val Pro Pro
65 70 75 80

Gly Val Thr Asn Ser Ser Phe Gln Val Thr Ser Gln Asn Val Gly Gln
85 90 95

Leu Thr Val Tyr Leu His Gly Asn His Ser Asn Gln Thr Gly Pro Arg
100 105 110

Ile Arg Phe Leu Val Ile Arg Ser Ser Ala Ile Ser Ile Ile Asn Gln
115 120 125

Val Ile Gly Trp Ile Tyr Phe Val Ala Trp Ser Ile Ser Phe Tyr Pro
130 135 140

Gln Val Ile Met Asn Trp Arg Arg Lys Ser Val Ile Gly Leu Ser Phe
145 150 155 160

Asp Phe Val Ala Leu Asn Leu Thr Gly Phe Val Ala Tyr Ser Val Phe
165 170 175

Asn Ile Gly Leu Leu Trp Val Pro Tyr Ile Lys Glu Gln Phe Leu Leu
180 185 190

Lys Tyr Pro Asn Gly Val Asn Pro Val Asn Ser Asn Asp Val Phe Phe
195 200 205

Ser Leu His Ala Val Val Leu Thr Leu Ile Ile Ile Val Gln Cys Cys
210 215 220

Leu Tyr Glu Arg Gly Gly Gln Arg Val Ser Trp Pro Ala Ile Gly Phe
225 230 235 240

Leu Val Leu Ala Trp Leu Phe Ala Phe Val Thr Met Ile Val Ala Ala
245 250 255

Val Gly Val Ile Thr Trp Leu Gln Phe Leu Phe Cys Phe Ser Tyr Ile
260 265 270

Lys Leu Ala Val Thr Leu Val Lys Tyr Phe Pro Gln Ala Tyr Met Asn
275 280 285

Phe Tyr Tyr Lys Ser Thr Glu Gly Trp Ser Ile Gly Asn Val Leu Leu
290 295 300

Asp Phe Thr Gly Gly Ser Phe Ser Leu Leu Gln Met Phe Leu Gln Ser
305 310 315 320

Tyr Asn Asn Asp Gln Trp Thr Leu Ile Phe Gly Asp Pro Thr Lys Phe
325 330 335

Gly Leu Gly Val Phe Ser Ile Val Phe Asp Val Val Phe Phe Ile Gln
340 345 350

His Phe Cys Leu Tyr Arg Lys Arg Pro Gly Tyr Asp Gln Leu Asn
355 360 365

<210> SEQ ID NO 2
<211> LENGTH: 2611
<212> TYPE: DNA
<213> ORGANISM: homo sapiens

<400> SEQUENCE: 2

```
cgcctctccc aaagtctagc cgggcagggg aacgcggtgc attcctgacc ggcacctggc     60
gaggctcatg cgtcccgtga gggcggttcc tcgagcctgg gggcgctcag attgctttgg    120
agacgctgag agaacctttg cgagagcgcc ggttgacgtg cggagtgcgg ggctccgggg    180
gactgagcag cacgagaccc catcctcccc tccgggtttt cacactgggc gaagggagga    240
ctcctgagct ctgcctcttc cagtaacatt gaggattact gtgttttgtg agagctcgct    300
aggcgcccta agcaacagag ttctgagaaa tcgagaaaca tgataaggaa ttggctgact    360
atttttatcc tttttcccct gaagctcgta gagaaatgtg agtcaagcgt cagcctcact    420
gttcctcctg tcgtaaagct ggagaacggc agctcgacca acgtcagcct caccctgcgg    480
ccaccattaa atgcaaccct ggtgatcact tttgaaatca catttcgttc caaaaatatt    540
actatccttg agctccccga tgaagttgtg gtgcctcctg gagtgacaaa ctcctctttt    600
caagtgacat ctcaaaatgt tggacaactt actgtttatc tacatggaaa tcactccaat    660
cagaccggcc cgaggatacg ctttcttgtg atccgcagca gcgccattag catcataaac    720
caggtgattg gctggatcta ctttgtggcc tggtccatct ccttctaccc tcaggtgatc    780
atgaattgga ggcggaaaag tgtcattggt ctgagcttcg acttcgtggc tctgaacctg    840
acaggcttcg tggcctacag tgtattcaac atcggcctcc tctgggtgcc ctacatcaag    900
gagcagtttc tcctcaaata ccccaacgga gtgaaccccg tgaacagcaa cgacgtcttc    960
ttcagcctgc acgcggttgt cctcacgctg atcatcatcg tgcagtgctg cctgtatgag   1020
cgcggtggcc agcgcgtgtc ctggcctgcc atcggcttcc tggtgctcgc gtggctcttc   1080
gcatttgtca ccatgatcgt ggctgcagtg ggagtgatca cgtggctgca gtttctcttc   1140
tgcttctcct acatcaagct cgcagtcacg ctggtcaagt attttccaca ggcctacatg   1200
aacttttact acaaaagcac tgagggctgg agcattggca acgtgctcct ggacttcacc   1260
gggggcagct tcagcctcct gcagatgttc ctccagtcct acaacaacga ccagtggacg   1320
ctgatcttcg gagacccaac caagtttgga ctcggggtct tctccatcgt cttcgacgtc   1380
gtcttcttca tccagcactt ctgtttgtac agaaagagac cggggtatga ccagctgaac   1440
tagcacccag ggacccagtg tacccagcct ctggcctcgt gccctgctgg ggaaggcctc   1500
acccagcgaa ggccggagaa gcggttgggc cctggcacac agggctggct cagtgtgcgg   1560
acagaggaga ccactctgct cctggggcca gaggccattc aatagcctgc cttcgtccgg   1620
gcccctcctg ggcctccccg gccaggcacg tggcaccgtc gccttgacac cgccatctct   1680
tttctttaag gcttcaggca gcgcgcacag gctctggcag ccgtctcagg caggactggg   1740
caccaagctt gcagccgaag gccttgcccc aaactaccag cgtttctgca agcagcttga   1800
agggctgacc ttgcagccgg gtgagccaag ggcactttgc tgccaccgct gcattcccag   1860
agatcaagca gcccggtgcc gtggccagtg aactcagagg tgctggtgga cgggctagga   1920
ctttggggtt aggccatggg gctctttctc tgaaggccac tttcctgacg tactctctgt   1980
acataactca gcgtccgtga ctgcagtaac agccagccct acccagagta tttctgagcc   2040
```

```
atgaggggcc caccagattg gttctgaatt ggattcatgc ccagcgcatt agcatagtaa   2100

ctcctttcag attttttgga gggacgtttg gaagtggctt actctcttct gccctctctc   2160

ctacctccac cttctcagat gagccccatc tgagcacatc cagctgctcc ttacccagca   2220

tctggagtac aggacatagc tctctcctgc taccagtctg tgccttagag gtcgttaggc   2280

ctgccaaacg gcgaccagct cccctggagc gagggcaggc cccttccctc tctttcccca   2340

gacacctact tgagactcac caatttctgg cctgttcagg agcctcagat aagtatttgt   2400

acttgagacc acctcacaca atctgtatgg gcccaaccct gatctcaaac ctccttccct   2460

ctgcccaaag ctgtccttcc tatggcagga ggggtggggg tcccaggacg tgcctcatac   2520

atgacttgag cttgtcagtc cactgagttt ccttctacga gatcaacgcg aggggcctgt   2580

atcttgaatt aaagcctact cgcttccttt c                                  2611
```

```
<210> SEQ ID NO 3
<211> LENGTH: 495
<212> TYPE: PRT
<213> ORGANISM: homo sapiens

<400> SEQUENCE: 3

Met Arg Ser Pro Val Arg Asp Leu Ala Arg Asn Asp Gly Glu Glu Ser
1               5                   10                  15

Thr Asp Arg Thr Pro Leu Leu Pro Gly Ala Pro Arg Ala Glu Ala Ala
            20                  25                  30

Pro Val Cys Cys Ser Ala Arg Tyr Asn Leu Ala Ile Leu Ala Phe Phe
        35                  40                  45

Gly Phe Phe Ile Val Tyr Ala Leu Arg Val Asn Leu Ser Val Ala Leu
    50                  55                  60

Val Asp Met Val Asp Ser Asn Thr Thr Leu Glu Asp Asn Arg Thr Ser
65                  70                  75                  80

Lys Ala Cys Pro Glu His Ser Ala Pro Ile Lys Val His His Asn Gln
                85                  90                  95

Thr Gly Lys Lys Tyr Gln Trp Asp Ala Glu Thr Gln Gly Trp Ile Leu
            100                 105                 110

Gly Ser Phe Phe Tyr Gly Tyr Ile Ile Thr Gln Ile Pro Gly Gly Tyr
        115                 120                 125

Val Ala Ser Lys Ile Gly Gly Lys Met Leu Leu Gly Phe Gly Ile Leu
    130                 135                 140

Gly Thr Ala Val Leu Thr Leu Phe Thr Pro Ile Ala Ala Asp Leu Gly
145                 150                 155                 160

Val Gly Pro Leu Ile Val Leu Arg Ala Leu Glu Gly Leu Gly Glu Gly
                165                 170                 175

Val Thr Phe Pro Ala Met His Ala Met Trp Ser Ser Trp Ala Pro Pro
            180                 185                 190

Leu Glu Arg Ser Lys Leu Leu Ser Ile Ser Tyr Ala Gly Ala Gln Leu
        195                 200                 205

Gly Thr Val Ile Ser Leu Pro Leu Ser Gly Ile Ile Cys Tyr Tyr Met
    210                 215                 220

Asn Trp Thr Tyr Val Phe Tyr Phe Phe Gly Thr Ile Gly Ile Phe Trp
225                 230                 235                 240

Phe Leu Leu Trp Ile Trp Leu Val Ser Asp Thr Pro Gln Lys His Lys
                245                 250                 255

Arg Ile Ser His Tyr Glu Lys Glu Tyr Ile Leu Ser Ser Leu Arg Asn
            260                 265                 270
```

```
Gln Leu Ser Ser Gln Lys Ser Val Pro Trp Val Pro Ile Leu Lys Ser
        275                 280                 285

Leu Pro Leu Trp Ala Ile Val Val Ala His Phe Ser Tyr Asn Trp Thr
    290                 295                 300

Phe Tyr Thr Leu Leu Thr Leu Leu Pro Thr Tyr Met Lys Glu Ile Leu
305                 310                 315                 320

Arg Phe Asn Val Gln Glu Asn Gly Phe Leu Ser Ser Leu Pro Tyr Leu
                325                 330                 335

Gly Ser Trp Leu Cys Met Ile Leu Ser Gly Gln Ala Ala Asp Asn Leu
            340                 345                 350

Arg Ala Lys Trp Asn Phe Ser Thr Leu Cys Val Arg Arg Ile Phe Ser
        355                 360                 365

Leu Ile Gly Met Ile Gly Pro Ala Val Phe Leu Val Ala Ala Gly Phe
    370                 375                 380

Ile Gly Cys Asp Tyr Ser Leu Ala Val Ala Phe Leu Thr Ile Ser Thr
385                 390                 395                 400

Thr Leu Gly Gly Phe Cys Ser Ser Gly Phe Ser Ile Asn His Leu Asp
                405                 410                 415

Ile Ala Pro Ser Tyr Ala Gly Ile Leu Leu Gly Ile Thr Asn Thr Phe
            420                 425                 430

Ala Thr Ile Pro Gly Met Val Gly Pro Val Ile Ala Lys Ser Leu Thr
        435                 440                 445

Pro Asp Asn Thr Val Gly Glu Trp Gln Thr Val Phe Tyr Ile Ala Ala
    450                 455                 460

Ala Ile Asn Val Phe Gly Ala Ile Phe Phe Thr Leu Phe Ala Lys Gly
465                 470                 475                 480

Glu Val Gln Asn Trp Ala Leu Asn Asp His His Gly His Arg His
                485                 490                 495
```

<210> SEQ ID NO 4
<211> LENGTH: 2512
<212> TYPE: DNA
<213> ORGANISM: homo sapiens

<400> SEQUENCE: 4

```
cggctacttt gcgccaatcc tacgagaact cccagaactc cgcttcccta gtccaaccca      60

agccagagtt gcccacacct aagatggcgg cggggggcgg agtcggcgcg gccgcctctg     120

ggcgggaccg cggggactag acgtggccgc ggggcggtgt catcgccccc gccccgcccg     180

gtccagccag ctcggcccgg gggcttcggg ctgtcgggcc ggcgctccct tctctgccag     240

gtggcgagta cacctgctca cgtaggcgtc atgaggtctc cggttcgaga cctggcccgg     300

aacgatggcg aggagagcac ggaccgcacg cctcttctac cgggcgcccc acgggccgaa     360

gccgctccag tgtgctgctc tgctcgttac aacttagcaa ttttggcctt ttttggtttc     420

ttcattgtgt atgcattacg tgtgaatctg agtgttgcgt tagtggatat ggtagattca     480

aatacaactt tagaagataa tagaacttcc aaggcgtgtc cagagcattc tgctcccata     540

aaagttcatc ataatcaaac gggtaagaag taccaatggg atgcagaaac tcaaggatgg     600

attctcggtt ccttttttta tggctacatc atcacacaga ttcctggagg atatgttgcc     660

agcaaaatag gggggaaaat gctgctagga tttgggatcc ttggcactgc tgtcctcacc     720

ctgttcactc ccattgctgc agatttagga gttggaccac tcattgtact cagagcacta     780

gaaggactag gagagggtgt tacatttcca gccatgcatg ccatgtggtc ttcttgggct     840

ccccctcttg aaagaagcaa acttcttagc atttcatatg caggagcaca gcttgggaca     900
```

```
gtaatttctc ttcctctttc tggaataatt tgctactata tgaattggac ttatgtcttc    960

tactttttg gtactattgg aatattttgg tttcttttgt ggatctggtt agttagtgac   1020

acaccacaaa aacacaagag aatttcccat tatgaaaagg aatacattct ttcatcatta   1080

agaaatcagc tttcttcaca gaagtcagtg ccgtgggtac ccattttaaa atccctgcca   1140

ctttgggcta tcgtagttgc acacttttct tacaactgga ctttttatac tttattgaca   1200

ttattgccta cttatatgaa ggagatccta aggttcaatg ttcaagagaa tgggttttta   1260

tcttcattgc cttatttagg ctcttggtta tgtatgatcc tgtctggtca agctgctgac   1320

aatttaaggg caaaatggaa tttttcaact ttatgtgttc gcagaatttt tagccttata   1380

ggaatgattg gacctgcagt attcctggta gctgctggct tcattggctg tgattattct   1440

ttggccgttg ctttcctaac tatatcaaca acactgggag gcttttgctc ttctggattt   1500

agcatcaacc atctggatat tgctccttcg tatgctggta tcctcctggg catcacaaat   1560

acatttgcca ctattccagg aatggttggg cccgtcattg ctaaaagtct gacccctgat   1620

aacactgttg gagaatggca aaccgtgttc tatattgctg ctgctattaa tgtttttggt   1680

gccattttct ttacactatt cgccaaaggt gaagtacaaa actgggctct caatgatcac   1740

catggacaca gacactgaag gaaccaataa ataatcctgc ctctattaat gtatttttat   1800

ttatcatgta acctcaaagt gccttctgta ttgtgtaagc attctatgtc ttttttaat   1860

tgtacttgta ttagattttt aaggcctata atcatgaaat atcactagtt gccagaataa   1920

taaaatgaac tgtgtttaat tatgaataat atgtaagcta ggacttctac tttaggttca   1980

catacctgcc tgctagtcgg gcaacatgaa gtaggacagt tctgttgatt ttttagggcc   2040

atactaaagg gaatgagctg aaacagacct cctgatacct ttgcttaatt aaactagatg   2100

ataattctca ggtactgata aacacctgtt gttgttcact ttcctcataa aaattgtcag   2160

ctctctctga cacttagacc tcaaacttta gcatctctgt ggagctgcca tccactgtat   2220

aatttcgcct ggcaactgga ctgaggggag tgtgcccagg cagctgccaa gcactccctc   2280

cctggcttca gggtcagagt gcccagcgtt tatcagaggc agcatccaag cccagagcca   2340

gtgtcgactc ttcggctggt gcctttcctc tgaggggcta tcaatgtgta gataaagccc   2400

tgagtaggca agagcagtga gatccactgc tatggtcttg atacatcctc aaactttccc   2460

ttcccagcac agaggaatat tggctggcat gcaacctgca aaagaaaaat gc           2512
```

```
<210> SEQ ID NO 5
<211> LENGTH: 537
<212> TYPE: PRT
<213> ORGANISM: homo sapiens

<400> SEQUENCE: 5

Gly Ala Ala Ser Ala Glu Leu Val Ile Gly Trp Cys Ile Phe Gly Pro
1               5                   10                  15

Leu Leu Leu Ala Ile Phe Ala Phe Cys Trp Ile Tyr Val Arg Lys Tyr
            20                  25                  30

Gln Ser Gln Arg Glu Ser Glu Val Val Ser Thr Ile Thr Ala Ile Phe
        35                  40                  45

Ser Leu Ala Ile Ala Leu Ile Thr Ser Ala Leu Leu Pro Val Asp Ile
    50                  55                  60

Phe Leu Val Ser Tyr Met Lys Asn Gln Asn Gly Thr Phe Lys Asp Trp
65                  70                  75                  80

Ala Asn Ala Asn Val Ser Arg Gln Ile Glu Asp Thr Val Leu Tyr Gly
```

```
                85                  90                  95

Tyr Tyr Thr Leu Tyr Ser Val Ile Leu Phe Cys Val Phe Phe Trp Ile
            100                 105                 110

Pro Phe Val Tyr Phe Tyr Tyr Glu Glu Lys Asp Asp Asp Asp Thr Ser
        115                 120                 125

Lys Cys Thr Gln Ile Lys Thr Ala Phe Lys Tyr Thr Leu Gly Phe Ala
    130                 135                 140

Val Ile Cys Ala Leu Leu Leu Leu Val Gly Ala Phe Val Pro Leu Asn
145                 150                 155                 160

Val Pro Asn Asn Lys Asn Ser Thr Glu Trp Glu Lys Val Lys Phe Leu
                165                 170                 175

Phe Glu Glu Leu Gly Ser Ser His Gly Leu Ala Ala Leu Ser Phe Ser
            180                 185                 190

Ile Ser Ser Leu Thr Leu Ile Gly Met Leu Ala Ala Ile Thr Tyr Thr
        195                 200                 205

Ala Tyr Gly Met Ser Ala Leu Pro Leu Asn Leu Ile Lys Gly Thr Arg
    210                 215                 220

Ser Ala Ala Tyr Glu Arg Leu Glu Asn Thr Glu Asp Ile Glu Glu Val
225                 230                 235                 240

Glu Gln His Ile Gln Thr Ile Lys Ser Lys Ser Lys Asp Gly Arg Pro
                245                 250                 255

Leu Pro Ala Arg Asp Lys Arg Ala Leu Lys Gln Phe Glu Glu Arg Leu
            260                 265                 270

Arg Thr Leu Arg Lys Arg Glu Arg His Leu Glu Tyr Ile Glu Asn Ser
        275                 280                 285

Trp Trp Thr Lys Phe Cys Gly Ala Leu Arg Pro Leu Lys Ile Ile Trp
    290                 295                 300

Gly Ile Phe Phe Ile Leu Val Ala Leu Leu Phe Ile Ile Ser Leu Phe
305                 310                 315                 320

Leu Ser Asn Leu Asp Lys Ala Leu His Ser Ala Gly Ile Asp Ser Gly
                325                 330                 335

Phe Ile Ile Phe Gly Ala Asn Leu Ser Asn Pro Leu Asn Met Leu Leu
            340                 345                 350

Pro Val Leu Gln Thr Val Phe Pro Leu Asp Tyr Ile Leu Ile Thr Ile
        355                 360                 365

Ile Ile Met Tyr Phe Ile Phe Thr Ser Met Ala Gly Ile Arg Asn Ile
    370                 375                 380

Gly Ile Trp Phe Phe Trp Val Arg Leu Tyr Lys Ile Arg Arg Gly Arg
385                 390                 395                 400

Thr Arg Pro Gln Ala Leu Leu Phe Leu Cys Met Ile Leu Leu Leu Ile
                405                 410                 415

Val Leu His Thr Ser Tyr Met Ile Tyr Ser Leu Ala Pro Gln Tyr Val
            420                 425                 430

Met Tyr Gly Ser Gln Asn Tyr Leu Ile Glu Ser Asn Ile Thr Tyr Asp
        435                 440                 445

Asp His Lys Asn Asn Ser Ala Phe Pro Val Pro Lys Arg Cys Asp Ala
    450                 455                 460

Asp Ala Pro Glu Asp Gln Cys Thr Val Thr Arg Thr Tyr Leu Phe Leu
465                 470                 475                 480

His Lys Phe Trp Phe Phe Ser Ala Ala Tyr Tyr Phe Gly Asn Trp Ala
                485                 490                 495

Phe Leu Val Val Phe Leu Ile Gly Leu Ile Val Ser Cys Cys Lys Gly
            500                 505                 510
```

```
Lys Lys Ser Val Ile Glu Gly Val Asp Glu Asp Asp Ser Asp Ile Ser
        515                 520                 525

Asp Asp Glu Pro Ser Val Tyr Ser Val
    530                 535


<210> SEQ ID NO 6
<211> LENGTH: 1979
<212> TYPE: DNA
<213> ORGANISM: homo sapiens

<400> SEQUENCE: 6

ggcgcggctt cggcggagct ggtgatcggc tggtgcatat ttggcccctt actactggct      60

atttttgcat tctgttggat atatgttcgt aaataccaaa gtcagcggga aagtgaagtt     120

gtctccacca taacggcaat tttttctctg gcgattgcac ttatcacatc agcacttctt     180

ccagtggata tatttttggt ttcttacatg aaaaatcaaa atggtacatt taaggactgg     240

gccaatgcta atgtcagcag acagatcgag gacactgtgt tatatggtta ctacacctta     300

tattctgtta tattattctg tgtgtttttc tggatccctt ttgtctactt ctactatgaa     360

gaaaaggatg atgatgatac tagtaaatgt actcaaatta aaactgcatt caagtatact     420

ttgggatttg ctgtaatttg tgcacttctt cttttagttg gagcttttgt tcctctaaat     480

gttcctaata acaaaaattc tacagagtgg gaaaaagtga agttcctgtt tgaagaactt     540

ggaagtagtc atggtttagc tgcattgtca ttttctatta gttctctgac cttgattgga     600

atgttggcag ctataactta cacagcctat ggcatgtctg cattaccttt aaatctaata     660

aaaggcacta gaagcgctgc ttacgaacgt ttagaaaaca ctgaagacat tgaagaagtg     720

gagcaacaca ttcaaacgat taaatcaaaa agcaaagatg gtcggccttt gccagcaagg     780

gataaacgcg ccttaaaaca atttgaagaa aggttaagaa cacttaggaa aagagagagg     840

cacttagaat acattgaaaa cagctggtgg acaaaatttt gtggtgctct gcgtcccctg     900

aagatcattt ggggaatatt tttcatctta gttgcattgc tgtttataat ttctctcttc     960

ctgtcaaatt tggataaagc ccttcattca gctggaatag attctggttt tataattttt    1020

ggagctaact tgagtaatcc actgaatatg cttttgcctg tactacaaac agtgtttcct    1080

cttgattata ttcttataac aattattatt atgtacttta tttttacttc aatggcggga    1140

attcgaaata tcggcatatg gttcttttgg gttagactat ataaaattag aagaggtaga    1200

accaggcccc aggccctctt atttctttgc atgatacttc tgcttattgt ccttcacact    1260

agctacatga tttatagtct tgctccccaa tatgtcatgt atggaagcca aaattactta    1320

atagagagca atataactta tgatgaccat aaaaacaatt cagccttccc tgtgccaaag    1380

agatgtgatg ctgatgcccc tgaagaccaa tgtactgtta cgcggacata cctgttcctt    1440

cacaagttct ggttctttag tgctgcatac tattttggta actgggcttt tcttgtggta    1500

ttcttgattg gattaattgt atcctgttgt aaagggaaga aatcagtcat tgaaggagta    1560

gatgaagatg attcagacat aagtgatgat gagccctctg tctattctgt ttgagagcct    1620

ctgtcttagg ggttttataa tgctgactga atgtctatta tgcatttttt aaagtgttaa    1680

actaacatta ggatgaactg actagcttca tcaaaaatgg gagcatggct attaaaaaaa    1740

ctatattttt tatgttatct gaagtaacat tattgtatca tagattaaca tttaaaattg    1800

ctgtaataat tctatgtaaa tataaaacta tggactttgt gagggaatgt ttgtggaaat    1860

ctttttctc tagtgtataa tagtgttgaa ttgattaaaa gtcttccaga attaatattc    1920
```

```
cctcttgtca cttcttaaaa acataataaa tcacttctac ctgtgcaaaa aaaaaaaaa    1979


<210> SEQ ID NO 7
<211> LENGTH: 518
<212> TYPE: PRT
<213> ORGANISM: homo sapiens

<400> SEQUENCE: 7

Met Ala Gly Leu Arg Asn Glu Ser Glu Gln Glu Pro Leu Leu Gly Asp
1               5                   10                  15

Thr Pro Gly Ser Arg Glu Trp Asp Ile Leu Glu Thr Glu Glu His Tyr
            20                  25                  30

Lys Ser Arg Trp Arg Ser Ile Arg Ile Leu Tyr Leu Thr Met Phe Leu
        35                  40                  45

Ser Ser Val Gly Phe Ser Val Val Met Met Ser Ile Trp Pro Tyr Leu
    50                  55                  60

Gln Lys Ile Asp Pro Thr Ala Asp Thr Ser Phe Leu Gly Trp Val Ile
65                  70                  75                  80

Ala Ser Tyr Ser Leu Gly Gln Met Val Ala Ser Pro Ile Phe Gly Leu
                85                  90                  95

Trp Ser Asn Tyr Arg Pro Arg Lys Glu Pro Leu Ile Val Ser Ile Leu
            100                 105                 110

Ile Ser Val Ala Ala Asn Cys Leu Tyr Ala Tyr Leu His Ile Pro Ala
        115                 120                 125

Ser His Asn Lys Tyr Tyr Met Leu Val Ala Arg Gly Leu Leu Gly Ile
    130                 135                 140

Gly Ala Gly Asn Val Ala Val Val Arg Ser Tyr Thr Ala Gly Ala Thr
145                 150                 155                 160

Ser Leu Gln Glu Arg Thr Ser Ser Met Ala Asn Ile Ser Met Cys Gln
                165                 170                 175

Ala Leu Gly Phe Ile Leu Gly Pro Val Phe Gln Thr Cys Phe Thr Phe
            180                 185                 190

Leu Gly Glu Lys Gly Val Thr Trp Asp Val Ile Lys Leu Gln Ile Asn
        195                 200                 205

Met Tyr Thr Thr Pro Val Leu Leu Ser Ala Phe Leu Gly Ile Leu Asn
    210                 215                 220

Ile Ile Leu Ile Leu Ala Ile Leu Arg Glu His Arg Val Asp Asp Ser
225                 230                 235                 240

Gly Arg Gln Cys Lys Ser Ile Asn Phe Glu Glu Ala Ser Thr Asp Glu
                245                 250                 255

Ala Gln Val Pro Gln Gly Asn Ile Asp Gln Val Ala Val Val Ala Ile
            260                 265                 270

Asn Val Leu Phe Phe Val Thr Leu Phe Ile Phe Ala Leu Phe Glu Thr
        275                 280                 285

Ile Ile Thr Pro Leu Thr Met Asp Met Tyr Ala Trp Thr Gln Glu Gln
    290                 295                 300

Ala Val Leu Tyr Asn Gly Ile Ile Leu Ala Ala Leu Gly Val Glu Ala
305                 310                 315                 320

Val Val Ile Phe Leu Gly Val Lys Leu Leu Ser Lys Lys Ile Gly Glu
                325                 330                 335

Arg Ala Ile Leu Leu Gly Gly Leu Ile Val Val Trp Val Gly Phe Phe
            340                 345                 350

Ile Leu Leu Pro Trp Gly Asn Gln Phe Pro Lys Ile Gln Trp Glu Asp
        355                 360                 365
```

```
Leu His Asn Asn Ser Ile Pro Asn Thr Thr Phe Gly Glu Ile Ile Ile
    370                 375                 380

Gly Leu Trp Lys Ser Pro Met Glu Asp Asp Asn Glu Arg Pro Thr Gly
385                 390                 395                 400

Cys Ser Ile Glu Gln Ala Trp Cys Leu Tyr Thr Pro Val Ile His Leu
                405                 410                 415

Ala Gln Phe Leu Thr Ser Ala Val Leu Ile Gly Leu Gly Tyr Pro Val
            420                 425                 430

Cys Asn Leu Met Ser Tyr Thr Leu Tyr Ser Lys Ile Leu Gly Pro Lys
        435                 440                 445

Pro Gln Gly Val Tyr Met Gly Trp Leu Thr Ala Ser Gly Ser Gly Ala
    450                 455                 460

Arg Ile Leu Gly Pro Met Phe Ile Ser Gln Val Tyr Ala His Trp Gly
465                 470                 475                 480

Pro Arg Trp Ala Phe Ser Leu Val Cys Gly Ile Ile Val Leu Thr Ile
                485                 490                 495

Thr Leu Leu Gly Val Val Tyr Lys Arg Leu Ile Ala Leu Ser Val Arg
            500                 505                 510

Tyr Gly Arg Ile Gln Glu
        515


<210> SEQ ID NO 8
<211> LENGTH: 1909
<212> TYPE: DNA
<213> ORGANISM: homo sapiens

<400> SEQUENCE: 8

aggttacaag cagcagatcc caccttcagt cctggctctg acaagccctc cagcttcacg      60

ccacccggga tgggagaaag caggtgtcgc gagagttggg cgcaagacgc cttgtaggga     120

gtgtaactat ggccggcctg cggaacgaaa gtgaacagga gccgctctta ggcgacacac     180

ctggaagcag agaatgggac attttagaga ctgaagagca ttataagagc cgatggagat     240

ctattaggat tttatatctt actatgtttc tcagcagtgt agggttttct gtagtgatga     300

tgtccatatg gccatatctc caaaagattg atccgacagc tgatacaagt tttttgggct     360

gggttattgc ttcatatagt cttggccaaa tggtagcttc acctatattt ggtttatggt     420

ctaattatag accaagaaaa gagcctctta ttgtctccat cttgatttcc gtggcagcca     480

actgcctcta tgcatatctc cacatcccag cttctcataa taaatactac atgctggttg     540

ctcgtggatt gttgggaatt ggagcaggaa atgtagcagt tgttagatca tatactgctg     600

gtgctacttc ccttcaggaa agaacaagtt ccatggcaaa cataagcatg tgtcaagcat     660

taggttttat tctaggtcca gtttttcaga cttgttttac attccttgga gaaaaaggtg     720

tgacatggga tgtgattaaa ctgcagataa acatgtatac aacaccagtt ttacttagcg     780

ccttcctggg aattttaaat attattctga tccttgccat actaagagaa catcgtgtgg     840

atgactcagg aagacagtgt aaaagtatta attttgaaga agcaagtaca gatgaagctc     900

aggttcccca aggaaatatt gaccaggttg ctgttgtggc catcaatgtt ctgttttttg     960

tgactctatt tatctttgcc ctttttgaaa ccatcattac tccattaaca atggatatgt    1020

atgcctggac tcaagaacaa gctgtgttat ataatggcat aatacttgct gctcttgggg    1080

ttgaagccgt tgttattttc ttaggagtta agttgctttc caaaaagatt ggcgagcgtg    1140

ctattctact gggaggactc atcgttgtat gggttggctt ctttatcttg ttaccttggg    1200

gaaatcaatt tcccaaaata cagtgggaag atttgcacaa taattcaatc cctaatacca    1260
```

```
catttgggga aattattatt ggtctttgga agtctccaat ggaagatgac aatgaaagac   1320

caactggttg ctcgattgaa caagcctggt gcctctacac cccggtgatt catctggccc   1380

agttccttac atcagctgtg ctaataggat taggctatcc agtctgcaat cttatgtcct   1440

atactctata ttcaaaaatt ctaggaccaa aacctcaggg tgtatacatg ggctggttaa   1500

cagcatctgg aagtggagcc cggattcttg ggcctatgtt catcagccaa gtgtatgctc   1560

actggggacc acgatgggca ttcagcctgg tgtgtggaat aatagtgctc accatcaccc   1620

tcctgggagt ggtttacaaa agactcattg ctctttctgt aagatatggg aggattcagg   1680

aataaactag ctaagactgt gatggaaact acttgctgtg tggcacttcc tggtctaaag   1740

ctctgctaga caattgcggt gagccagtct ccaagaatca gactacagat attgcagatt   1800

ttgaagaaca agaacatatg ttgaataaca gagagaattc tacatgtcat tgtgaatagt   1860

aggttatata aaaacatact agatgataat ttcaaaaaaa aaaaaaaaa               1909
```

<210> SEQ ID NO 9
<211> LENGTH: 438
<212> TYPE: PRT
<213> ORGANISM: homo sapiens

<400> SEQUENCE: 9

```
Met Gly Gly Cys Ala Gly Ser Arg Arg Arg Phe Ser Asp Ser Glu Gly
1               5                   10                  15

Glu Glu Thr Val Pro Glu Pro Arg Leu Pro Leu Leu Asp His Gln Gly
            20                  25                  30

Ala His Trp Lys Asn Ala Val Gly Phe Trp Leu Leu Gly Leu Cys Asn
        35                  40                  45

Asn Phe Ser Tyr Val Val Met Leu Ser Ala Ala His Asp Ile Leu Ser
    50                  55                  60

His Lys Arg Thr Ser Gly Asn Gln Ser His Val Asp Pro Gly Pro Thr
65                  70                  75                  80

Pro Ile Pro His Asn Ser Ser Ser Arg Phe Asp Cys Asn Ser Val Ser
                85                  90                  95

Thr Ala Ala Val Leu Leu Ala Asp Ile Leu Pro Thr Leu Val Ile Lys
            100                 105                 110

Leu Leu Ala Pro Leu Gly Leu His Leu Leu Pro Tyr Ser Pro Arg Val
        115                 120                 125

Leu Val Ser Gly Ile Cys Ala Ala Gly Ser Phe Val Leu Val Ala Phe
    130                 135                 140

Ser His Ser Val Gly Thr Ser Leu Cys Gly Val Val Phe Ala Ser Ile
145                 150                 155                 160

Ser Ser Gly Leu Gly Glu Val Thr Phe Leu Ser Leu Thr Ala Phe Tyr
                165                 170                 175

Pro Arg Ala Val Ile Ser Trp Trp Ser Ser Gly Thr Gly Gly Ala Gly
            180                 185                 190

Leu Leu Gly Ala Leu Ser Tyr Leu Gly Leu Thr Gln Ala Gly Leu Ser
        195                 200                 205

Pro Gln Gln Thr Leu Leu Ser Met Leu Gly Ile Pro Ala Leu Leu Leu
    210                 215                 220

Ala Ser Tyr Phe Leu Leu Leu Thr Ser Pro Glu Ala Gln Asp Pro Gly
225                 230                 235                 240

Gly Glu Glu Glu Ala Glu Ser Ala Ala Arg Gln Pro Leu Ile Arg Thr
                245                 250                 255
```

```
Glu Ala Pro Glu Ser Lys Pro Gly Ser Ser Ser Ser Leu Ser Leu Arg
            260                 265                 270

Glu Arg Trp Thr Val Phe Lys Gly Leu Leu Trp Tyr Ile Val Pro Leu
        275                 280                 285

Val Val Val Tyr Phe Ala Glu Tyr Phe Ile Asn Gln Gly Leu Phe Glu
    290                 295                 300

Leu Leu Phe Phe Trp Asn Thr Ser Leu Ser His Ala Gln Gln Tyr Arg
305                 310                 315                 320

Trp Tyr Gln Met Leu Tyr Gln Ala Gly Val Phe Ala Ser Arg Ser Ser
                325                 330                 335

Leu Arg Cys Cys Arg Ile Arg Phe Thr Trp Ala Leu Ala Leu Leu Gln
            340                 345                 350

Cys Leu Asn Leu Val Phe Leu Leu Ala Asp Val Trp Phe Gly Phe Leu
        355                 360                 365

Pro Ser Ile Tyr Leu Val Phe Leu Ile Ile Leu Tyr Glu Gly Leu Leu
    370                 375                 380

Gly Gly Ala Ala Tyr Val Asn Thr Phe His Asn Ile Ala Leu Glu Thr
385                 390                 395                 400

Ser Asp Glu His Arg Glu Phe Ala Met Ala Ala Thr Cys Ile Ser Asp
                405                 410                 415

Thr Leu Gly Ile Ser Leu Ser Gly Leu Leu Ala Leu Pro Leu His Asp
            420                 425                 430

Phe Leu Cys Gln Leu Ser
        435
```

<210> SEQ ID NO 10
<211> LENGTH: 1689
<212> TYPE: DNA
<213> ORGANISM: homo sapiens

<400> SEQUENCE: 10

```
cccctagaca agccggagct gggaccggca atcgggcgtt gatccttgtc acctgtcgca     60

gaccctcatc cctcccgtgg gagccccctt tggacactct atgaccctgg accctcgggg    120

gacctgaact tgatgcgatg ggaggctgtg caggctcgcg gcggcgcttt tcggattccg    180

agggggagga gaccgtcccg gagccccggc tccctctgtt ggaccatcag ggcgcgcatt    240

ggaagaacgc ggtgggcttc tggctgctgg gcctttgcaa caacttctct tatgtggtga    300

tgctgagtgc cgcccacgac atccttagcc acaagaggac atcgggaaac cagagccatg    360

tggacccagg cccaacgccg atcccccaca acagctcatc acgatttgac tgcaactctg    420

tctctacggc tgctgtgctc ctggcggaca tcctccccac actcgtcatc aaattgttgg    480

ctcctcttgg ccttcacctg ctgccctaca gcccccgggt tctcgtcagt gggatttgtg    540

ctgctggaag cttcgtcctg gttgcctttt ctcattctgt ggggaccagc ctgtgtggtg    600

tggtcttcgc tagcatctca tcaggccttg gggaggtcac cttcctctcc ctcactgcct    660

tctaccccag ggccgtgatc tcctggtggt cctcagggac tgggggagct gggctgctgg    720

gggccctgtc ctacctgggc ctcacccagg ccggcctctc ccctcagcag accctgctgt    780

ccatgctggg tatccctgcc ctgctgctgg ccagctattt cttgttgctc acatctcctg    840

aggcccagga ccctggaggg gaagaagaag cagagagcgc agcccggcag cccctcataa    900

gaaccgaggc cccggagtcg aagccaggct ccagctccag cctctccctt cgggaaaggt    960

ggacagtatt caagggtctg ctgtggtaca ttgttccctt ggtcgtagtt tactttgccg   1020

agtatttcat taaccaggga ctttttgaac tcctcttttt ctggaacact tccctgagtc   1080
```

```
acgctcagca ataccgctgg taccagatgc tgtaccaggc tggcgtcttt gcctcccgct   1140

cttctctccg ctgctgtcgc atccgtttca cctgggccct ggccctgctg cagtgcctca   1200

acctggtgtt cctgctggca gacgtgtggt tcggctttct gccaagcatc tacctcgtct   1260

tcctgatcat tctgtatgag ggctcctgg gaggcgcagc ctacgtgaac accttccaca    1320

acatcgccct ggagaccagt gatgagcacc gggagtttgc aatggcggcc acctgcatct   1380

ctgacacact ggggatctcc ctgtcggggc tcctggcttt gcctctgcat gacttcctct   1440

gccagctctc ctgatactcg ggatcctcag gacgcaggtc acattcacct gtgggcagag   1500

ggacaggtca gacacccagg cccaccccag agaccctcca tgaactgtgc tcccagcctt   1560

cccggcaggt ctgggagtag ggaagggctg aagccttgtt tccttgcagg ggggccagcc   1620

attgtctccc acttggggag tttcttcctg gcatcatgcc ttctgaataa atgccgattt   1680

tgtccatgg                                                             1689


<210> SEQ ID NO 11
<211> LENGTH: 805
<212> TYPE: PRT
<213> ORGANISM: homo sapiens

<400> SEQUENCE: 11

Met Ala Asn Val Ser Lys Lys Val Ser Trp Ser Gly Arg Asp Arg Asp
1               5                   10                  15

Asp Glu Glu Ala Ala Pro Leu Leu Arg Arg Thr Ala Arg Pro Gly Gly
            20                  25                  30

Gly Thr Pro Leu Leu Asn Gly Ala Gly Pro Gly Ala Ala Arg Gln Ser
        35                  40                  45

Pro Arg Ser Ala Leu Phe Arg Val Gly His Met Ser Ser Val Glu Leu
    50                  55                  60

Asp Asp Glu Leu Leu Asp Pro Asp Met Asp Pro Pro His Pro Phe Pro
65                  70                  75                  80

Lys Glu Ile Pro His Asn Glu Lys Leu Leu Ser Leu Lys Tyr Glu Ser
                85                  90                  95

Leu Asp Tyr Asp Asn Ser Glu Asn Gln Leu Phe Leu Glu Glu Glu Arg
            100                 105                 110

Arg Ile Asn His Thr Ala Phe Arg Thr Val Glu Ile Lys Arg Trp Val
        115                 120                 125

Ile Cys Ala Leu Ile Gly Ile Leu Thr Gly Leu Val Ala Cys Phe Ile
    130                 135                 140

Asp Ile Val Val Glu Asn Leu Ala Gly Leu Lys Tyr Arg Val Ile Lys
145                 150                 155                 160

Gly Asn Ile Asp Lys Phe Thr Glu Lys Gly Gly Leu Ser Phe Ser Leu
                165                 170                 175

Leu Leu Trp Ala Thr Leu Asn Ala Ala Phe Val Leu Val Gly Ser Val
            180                 185                 190

Ile Val Ala Phe Ile Glu Pro Val Ala Ala Gly Ser Gly Ile Pro Gln
        195                 200                 205

Ile Lys Cys Phe Leu Asn Gly Val Lys Ile Pro His Val Val Arg Leu
    210                 215                 220

Lys Thr Leu Val Ile Lys Val Ser Gly Val Ile Leu Ser Val Val Gly
225                 230                 235                 240

Gly Leu Ala Val Gly Lys Glu Gly Pro Met Ile His Ser Gly Ser Val
                245                 250                 255
```

```
Ile Ala Ala Gly Ile Ser Gln Gly Arg Ser Thr Ser Leu Lys Arg Asp
            260                 265                 270

Phe Lys Ile Phe Glu Tyr Phe Arg Arg Asp Thr Glu Lys Arg Asp Phe
        275                 280                 285

Val Ser Ala Gly Ala Ala Ala Gly Val Ser Ala Ala Phe Gly Ala Pro
    290                 295                 300

Val Gly Gly Val Leu Phe Ser Leu Glu Glu Gly Ala Ser Phe Trp Asn
305                 310                 315                 320

Gln Phe Leu Thr Trp Arg Ile Phe Phe Ala Ser Met Ile Ser Thr Phe
                325                 330                 335

Thr Leu Asn Phe Val Leu Ser Ile Tyr His Gly Asn Met Trp Asp Leu
            340                 345                 350

Ser Ser Pro Gly Leu Ile Asn Phe Gly Arg Phe Asp Ser Glu Lys Met
        355                 360                 365

Ala Tyr Thr Ile His Glu Ile Pro Val Phe Ile Ala Met Gly Val Val
    370                 375                 380

Gly Gly Val Leu Gly Ala Val Phe Asn Ala Leu Asn Tyr Trp Leu Thr
385                 390                 395                 400

Met Phe Arg Ile Arg Tyr Ile His Arg Pro Cys Leu Gln Val Ile Glu
                405                 410                 415

Ala Val Leu Val Ala Ala Val Thr Ala Thr Val Ala Phe Val Leu Ile
            420                 425                 430

Tyr Ser Ser Arg Asp Cys Gln Pro Leu Gln Gly Gly Ser Met Ser Tyr
        435                 440                 445

Pro Leu Gln Leu Phe Cys Ala Asp Gly Glu Tyr Asn Ser Met Ala Ala
    450                 455                 460

Ala Phe Phe Asn Thr Pro Glu Lys Ser Val Val Ser Leu Phe His Asp
465                 470                 475                 480

Pro Pro Gly Ser Tyr Asn Pro Leu Thr Leu Gly Leu Phe Thr Leu Val
                485                 490                 495

Tyr Phe Phe Leu Ala Cys Trp Thr Tyr Gly Leu Thr Val Ser Ala Gly
            500                 505                 510

Val Phe Ile Pro Ser Leu Leu Ile Gly Ala Ala Trp Gly Arg Leu Phe
        515                 520                 525

Gly Ile Ser Leu Ser Tyr Leu Thr Gly Ala Ala Ile Trp Ala Asp Pro
    530                 535                 540

Gly Lys Tyr Ala Leu Met Gly Ala Ala Ala Gln Leu Gly Gly Ile Val
545                 550                 555                 560

Arg Met Thr Leu Ser Leu Thr Val Ile Met Met Glu Ala Thr Ser Asn
                565                 570                 575

Val Thr Tyr Gly Phe Pro Ile Met Leu Val Leu Met Thr Ala Lys Ile
            580                 585                 590

Val Gly Asp Val Phe Ile Glu Gly Leu Tyr Asp Met His Ile Gln Leu
        595                 600                 605

Gln Ser Val Pro Phe Leu His Trp Glu Ala Pro Val Thr Ser His Ser
    610                 615                 620

Leu Thr Ala Arg Glu Val Met Ser Thr Pro Val Thr Cys Leu Arg Arg
625                 630                 635                 640

Arg Glu Lys Val Gly Val Ile Val Asp Val Leu Ser Asp Thr Ala Ser
                645                 650                 655

Asn His Asn Gly Phe Pro Val Val Glu His Ala Asp Asp Thr Gln Pro
            660                 665                 670

Ala Arg Leu Gln Gly Leu Ile Leu Arg Ser Gln Leu Ile Val Leu Leu
```

```
        675                 680                 685

Lys His Lys Val Phe Val Glu Arg Ser Asn Leu Gly Leu Val Gln Arg
    690                 695                 700

Arg Leu Arg Leu Lys Asp Phe Arg Asp Ala Tyr Pro Arg Phe Pro Pro
705                 710                 715                 720

Ile Gln Ser Ile His Val Ser Gln Asp Glu Arg Glu Cys Thr Met Asp
                725                 730                 735

Leu Ser Glu Phe Met Asn Pro Ser Pro Tyr Thr Val Pro Gln Glu Ala
            740                 745                 750

Ser Leu Pro Arg Val Phe Lys Leu Phe Arg Ala Leu Gly Leu Arg His
        755                 760                 765

Leu Val Val Val Asp Asn Arg Asn Gln Val Val Gly Leu Val Thr Arg
    770                 775                 780

Lys Asp Leu Ala Arg Tyr Arg Leu Gly Lys Arg Gly Leu Glu Glu Leu
785                 790                 795                 800

Ser Leu Ala Gln Thr
                805


<210> SEQ ID NO 12
<211> LENGTH: 3277
<212> TYPE: DNA
<213> ORGANISM: homo sapiens

<400> SEQUENCE: 12

gccggcgctt cccggccggt gtcgctccgc ggcgggccat ggccaacgtc tctaagaagg     60

tgtcctggtc cggccgggac cgggacgacg aggaggcggc gccgctgctg cggaggacgg    120

cgcggcccgg cggggggacg ccgctgctga acggggctgg gcccggggct gcgcgccagt    180

caccacgttc tgcgcttttc cgagtcggac atatgagcag cgtggagctg gatgatgaac    240

ttttggaccc ggatatggac cctccacatc ccttccccaa ggagatccca cacaacgaga    300

agctcctgtc cctcaagtat gagagcttgg actatgacaa cagtgagaac cagctgttcc    360

tggaggagga gcggcggatc aatcacacgg ccttccggac ggtggagatc aagcgctggg    420

tcatctgcgc cctcattggg atcctcacgg gcctcgtggc ctgcttcatt gacatcgtgg    480

tggaaaacct ggctggcctc aagtacaggg tcatcaaggg caatatcgac aagttcacag    540

agaagggcgg actgtccttc tccctgttgc tgtgggccac gctgaacgcc gccttcgtgc    600

tcgtgggctc tgtgattgtg gctttcatag agccggtggc tgctggcagc ggaatccccc    660

agatcaagtg cttcctcaac ggggtgaaga tcccccacgt ggtgcggctc aagacgttgg    720

tgatcaaagt gtccggtgtg atcctgtccg tggtcggggg cctggccgtg ggaaaggaag    780

ggccgatgat ccactcaggt tcagtgattg ccgccgggat ctctcaggga aggtcaacgt    840

cactgaaacg agatttcaag atcttcgagt acttccgcag agacacagag aagcgggact    900

tcgtctccgc aggggctgcg gccggagtgt cagcggcgtt tggagccccc gtgggtgggg    960

tcctgttcag cttggaggag ggtgcgtcct tctggaacca gttcctgacc tggaggatct   1020

tctttgcttc catgatctcc acgttcaccc tgaattttgt tctgagcatt taccacggga   1080

acatgtggga cctgtccagc ccaggcctca tcaacttcgg aaggtttgac tcggagaaaa   1140

tggcctacac gatccacgag atcccggtct tcatcgccat gggcgtggtg ggcggtgtgc   1200

ttggagctgt gttcaatgcc ttgaactact ggctgaccat gtttcgaatc aggtacatcc   1260

accggccctg cctgcaggtg attgaggccg tgctggtggc cgccgtcacg gccacagttg   1320

ccttcgtgct gatctactcg tcgcgggatt gccagcccct gcagggggc tccatgtcct   1380
```

```
acccgctgca gctcttttgt gcagatggcg agtacaactc catggctgcg gccttcttca   1440

acaccccgga gaagagcgtg gtgagcctct tccacgaccc gccaggctcc tacaaccccc   1500

tgaccctcgg cctgttcacg ctggtctact tcttcctggc ctgctggacc tacgggctca   1560

cggtgtctgc cggggtcttc atcccgtccc tgctcatcgg ggctgcctgg ggccggctct   1620

ttgggatctc cctgtcctac ctcacggggg cggcgatctg ggcggacccc ggcaaatacg   1680

ccctgatggg agctgctgcc cagctgggcg ggattgtgcg gatgacactg agcctgaccg   1740

tcatcatgat ggaggccacc agcaacgtga cctacggctt ccccatcatg ctggtgctca   1800

tgaccgccaa gatcgtgggc gacgtcttca ttgagggcct gtacgacatg cacattcagc   1860

tgcagagtgt gcccttcctg cactgggagg ccccggtcac ctcacactca ctcactgcca   1920

gggaggtgat gagcacacca gtgacctgcc tgaggcggcg tgagaaggtc ggcgtcattg   1980

tggacgtgct gagcgacacg gcgtccaatc acaacggctt ccccgtggtg gagcatgccg   2040

atgacaccca gcctgcccgg ctccagggcc tgatcctgcg ctcccagctc atcgttctcc   2100

taaagcacaa ggtgtttgtg gagcggtcca acctgggcct ggtacagcgg cgcctgaggc   2160

tgaaggactt ccgagacgcc tacccgcgct tcccacccat ccagtccatc cacgtgtccc   2220

aggacgagcg ggagtgcacc atggacctct ccgagttcat gaacccctcc ccctacacgg   2280

tgccccagga ggcgtcgctc ccacgggtgt tcaagctgtt ccgggccctg ggcctgcggc   2340

acctggtggt ggtggacaac cgcaatcagg ttgtcgggtt ggtgaccagg aaggacctcg   2400

ccaggtaccg cctgggaaag agaggcttgg aggagctctc gctggcccag acgtgaggcc   2460

cagccctgcc cataatgggc actggcgctg gcaccccggc ccttctgcat ttcctcccgg   2520

agtcactggt ttctcggccc aaaccatgct ccccagcagt ggcaatggcg agcaccctgc   2580

agctgggcgg gcaggcggca ggcgcggaac tgaccctctc gcgggactga ccctgttgtg   2640

ggcagtggtc tccccccttg gcgcctcctt gcgcaggccc agcctccact ctcctcgtct   2700

aggtttcttt acctccaggg atcagctgtg tgtgtgtgac ctccctaccg ggctatcggc   2760

ctcttgggag ccagcggcag ggccggcacc tgcgtgcctg tgcccgtgtg cgtgagacag   2820

agcccttgcc cctgctgctg ccccgagggc tgccctgccc tggaagggcc cctctgcctc   2880

cacaccagtg gagtcttcga gacttgggag ctgcttggcc tcattttcag ccatgagcag   2940

acggcctgtg gtccctgggc ctgaggcacg gactcgtagc accagggttt ggaggctgcg   3000

accgccccgg agagcagctt cacactggcg ccacagagga gccccacgtg cactccccgg   3060

cctgcatccg gcttgggtac acaggcccag aggactgggg tgactcacgg gccctgtgct   3120

gtgatgttga gagctgagaa aaacctccaa ggccctgagc cccatgccca gccctgcctt   3180

ggtcccccaa tccccagagc ttggagtctg ggccccacac ccagccctgc cttggtccct   3240

gagcctcaaa gcgtggaatt gctgccctgt ggacact                            3277
```

<210> SEQ ID NO 13
<211> LENGTH: 334
<212> TYPE: PRT
<213> ORGANISM: homo sapiens

<400> SEQUENCE: 13

```
Met Glu Pro Gly Pro Thr Ala Ala Gln Arg Arg Cys Ser Leu Pro Pro
1               5                   10                  15

Trp Leu Pro Leu Gly Leu Leu Leu Trp Ser Gly Leu Ala Leu Gly Ala
            20                  25                  30
```

```
Leu Pro Phe Gly Ser Ser Pro His Arg Val Phe His Asp Leu Leu Ser
        35                  40                  45

Glu Gln Gln Leu Leu Glu Val Glu Asp Leu Ser Leu Ser Leu Leu Gln
    50                  55                  60

Gly Gly Gly Leu Gly Pro Leu Ser Leu Pro Pro Asp Leu Pro Asp Leu
65                  70                  75                  80

Asp Pro Glu Cys Arg Glu Leu Leu Leu Asp Phe Ala Asn Ser Ser Ala
                85                  90                  95

Glu Leu Thr Gly Cys Leu Val Arg Ser Ala Arg Pro Val Arg Leu Cys
            100                 105                 110

Gln Thr Cys Tyr Pro Leu Phe Gln Gln Val Val Ser Lys Met Asp Asn
        115                 120                 125

Ile Ser Arg Ala Ala Gly Asn Thr Ser Glu Ser Gln Ser Cys Ala Arg
    130                 135                 140

Ser Leu Leu Met Ala Asp Arg Met Gln Ile Val Val Ile Leu Ser Glu
145                 150                 155                 160

Phe Phe Asn Thr Thr Trp Gln Glu Ala Asn Cys Ala Asn Cys Leu Thr
                165                 170                 175

Asn Asn Ser Glu Glu Leu Ser Asn Ser Thr Val Tyr Phe Leu Asn Leu
            180                 185                 190

Phe Asn His Thr Leu Thr Cys Phe Glu His Asn Leu Gln Gly Asn Ala
        195                 200                 205

His Ser Leu Leu Gln Thr Lys Asn Tyr Ser Glu Val Cys Lys Asn Cys
    210                 215                 220

Arg Glu Ala Tyr Lys Thr Leu Ser Ser Leu Tyr Ser Glu Met Gln Lys
225                 230                 235                 240

Met Asn Glu Leu Glu Asn Lys Ala Glu Pro Gly Thr His Leu Cys Ile
                245                 250                 255

Asp Val Glu Asp Ala Met Asn Ile Thr Arg Lys Leu Trp Ser Arg Thr
            260                 265                 270

Phe Asn Cys Ser Val Pro Cys Ser Asp Thr Val Pro Val Ile Ala Val
        275                 280                 285

Ser Val Phe Ile Leu Phe Leu Pro Val Val Phe Tyr Leu Ser Ser Phe
    290                 295                 300

Leu His Ser Glu Gln Lys Lys Arg Lys Leu Ile Leu Pro Lys Arg Leu
305                 310                 315                 320

Lys Ser Ser Thr Ser Phe Ala Asn Ile Gln Glu Asn Ser Asn
                325                 330
```

<210> SEQ ID NO 14
<211> LENGTH: 2869
<212> TYPE: DNA
<213> ORGANISM: homo sapiens

<400> SEQUENCE: 14

```
ggctgtccgc ggtgccggct gggggcggag aggcggcggt gggctccctg gggtgtgtga      60

gcccggtgat ggagccgggc ccgacagccg cgcagcggag gtgttcgttg ccgccgtggc     120

tgccgctggg gctgctgctg tggtcggggc tggccctggg cgcgctcccc ttcggcagca     180

gtccgcacag ggtcttccac gacctcctgt cggagcagca gttgctggag gtggaggact     240

tgtccctgtc cctcctgcag ggtggagggc tggggcctct gtcgctgccc ccggacctgc     300

cggatctgga tcctgagtgc cgggagctcc tgctggactt cgccaacagc agcgcagagc     360

tgacagggtg tctggtgcgc agcgcccggc ccgtgcgcct ctgtcagacc tgctaccccc     420
```

```
tcttccaaca ggtcgtcagc aagatggaca acatcagccg agccgcgggg aatacttcag    480
agagtcagag ttgtgccaga agtctcttaa tggcagatag aatgcaaata gttgtgattc    540
tctcagaatt ttttaatacc acatggcagg aggcaaattg tgcaaattgt ttaacaaaca    600
acagtgaaga attatcaaac agcacagtat atttccttaa tctatttaat cacaccctga    660
cctgctttga acataacctt caggggaatg cacatagtct tttacagaca aaaaattatt    720
cagaagtatg caaaaactgc cgtgaagcat acaaaactct gagtagtctg tacagtgaaa    780
tgcaaaaaat gaatgaactt gagaataagg ctgaacctgg aacacattta tgcattgatg    840
tggaagatgc aatgaacatc actcgaaaac tatggagtcg aactttcaac tgttcagtcc    900
cttgcagtga cacagtgcct gtaattgctg tttctgtgtt cattctcttt ctacctgttg    960
tcttctacct tagtagcttt cttcactcag agcaaaagaa acgcaaactc attctgccca   1020
aacgtctcaa gtccagtacc agttttgcaa atattcagga aaattcaaac tgagacctac   1080
aaaatggaga attgacatat cacgtgaatg aatggtggaa gacacaactt ggtttcagaa   1140
agaagataaa ctgtgatttg acaagtcaag ctcttaagaa atacaaggac ttcagatcca   1200
tttttaaata agaattttcg atttttcttt ccttttccac ttctttctaa cagatttgga   1260
tatttttaat ttccaggcat agcagtgtta tctattttaa tgtgtatttg tcacaataac   1320
agaacatgca agaacaatca ttattttatt ttataggcat ttgattacta ttctagactt   1380
ctggtatctt cttactaaca taagtatctc aagtagaaaa gtttttgaaa actaacattt   1440
aaaaattaat cagttacagt aaagactttg aaaaagaaat gtacttgtta ggaagtagct   1500
taattacccc ccattgcagt attattgtta tatatatagt taatatgttg tacatcacaa   1560
taatatataa ttcagtctct agtttcccta gagtcatttt tgaaaccact gattgcaaac   1620
ctccctgaca atttttaaaa gtagtaagcc acattacatt tatctttgta aaaagattta   1680
tggtaactgg tttcttactt gacttttata aatagtattt tacatcttat ttttgccttt   1740
atttcataag taatttaaaa atcactggat tgctttatta tattcagggc aatatggatt   1800
atttttatac caaggatttg catcgtgaat taaattaagt tatttggcaa tttataattt   1860
attactactt taaatcaaat gtagcattat cacactgtat ttaaattgtc atttttttaaa   1920
ggaatatttt cttcttaaga tatatagagg attttggaga agagagacag gaggggtaaa   1980
accagcttaa ggttcagcga gcagaaaggg acctgagagg atgctcactg taagactgtt   2040
ggacagtggt gtgtattgag ggatgaatc ggaacgatag tctcatgcag aaaatagtga   2100
gattaagatc atccttattg tttctaaatt atttcaatca gatgaaagtg atacgattga   2160
aatgaaatca catagttcgt gctcagaaat tctattttgg tatgtttgta ttagccttta   2220
gaaaaaacac tccgtttcag aattgttcac agttttattt cttaggtttt tagagttcag   2280
gatttcattt attaatttct tcttgctttt ttggtggaaa taggctttgt tgtaaacatt   2340
aagaatataa aatctcctct atatagaaac aagaattttg ttaaaaagag aatttgaatc   2400
ccttcctata ctataaaatg ctctataggg agacaaagtg tttctttttt cttttatgtt   2460
tactgtttat gtggagtgaa atataaggct cttggatgta taacatactc aaaagctgtt   2520
acactttctc tgatctgctg tgatccactg aaaatgtgct ggggtttgtt ctgctgtcac   2580
tgtttatgct gctggaactt agcactgtct tgatttgaag catatgattg agagccattt   2640
gaagcaatct tcattaatgc agataaaaca agtttacatg tgcagagtta gaaaatgaca   2700
tgttcaattc tgtaagtggt gactttttga gcacctttca gtattatgta tttgtaaaaa   2760
ccattgtttt tggatataaa gctaataagc actttaaaaa aaaaaaaaaa aaaaaaaaaa   2820
```

```
aaaaaaaaaa aaaaaaaaaa aaaaaaaaaa aaagaaaaaa aaaaaaaaa              2869


<210> SEQ ID NO 15
<211> LENGTH: 580
<212> TYPE: PRT
<213> ORGANISM: homo sapiens

<400> SEQUENCE: 15

Met Thr Ala Pro Ala Gly Pro Arg Gly Ser Glu Thr Glu Arg Leu Leu
1               5                   10                  15

Thr Pro Asn Pro Gly Tyr Gly Thr Gln Ala Gly Pro Ser Pro Ala Pro
            20                  25                  30

Pro Thr Pro Pro Glu Glu Glu Asp Leu Arg Arg Arg Leu Lys Tyr Phe
        35                  40                  45

Phe Met Ser Pro Cys Asp Lys Phe Arg Ala Lys Gly Arg Lys Pro Cys
    50                  55                  60

Lys Leu Met Leu Gln Val Val Lys Ile Leu Val Val Thr Val Gln Leu
65                  70                  75                  80

Ile Leu Phe Gly Leu Ser Asn Gln Leu Ala Val Thr Phe Arg Glu Glu
                85                  90                  95

Asn Thr Ile Ala Phe Arg His Leu Phe Leu Leu Gly Tyr Ser Asp Gly
            100                 105                 110

Ala Asp Asp Thr Phe Ala Ala Tyr Thr Arg Glu Gln Leu Tyr Gln Ala
        115                 120                 125

Ile Phe His Ala Val Asp Gln Tyr Leu Ala Leu Pro Asp Val Ser Leu
    130                 135                 140

Gly Arg Tyr Ala Tyr Val Arg Gly Gly Gly Asp Pro Trp Thr Asn Gly
145                 150                 155                 160

Ser Gly Leu Ala Leu Cys Gln Arg Tyr Tyr His Arg Gly His Val Asp
                165                 170                 175

Pro Ala Asn Asp Thr Phe Asp Ile Asp Pro Met Val Val Thr Asp Cys
            180                 185                 190

Ile Gln Val Asp Pro Pro Glu Arg Pro Pro Pro Pro Pro Ser Asp Asp
        195                 200                 205

Leu Thr Leu Leu Glu Ser Ser Ser Ser Tyr Lys Asn Leu Thr Leu Lys
    210                 215                 220

Phe His Lys Leu Val Asn Val Thr Ile His Phe Arg Leu Lys Thr Ile
225                 230                 235                 240

Asn Leu Gln Ser Leu Ile Asn Asn Glu Ile Pro Asp Cys Tyr Thr Phe
                245                 250                 255

Ser Val Leu Ile Thr Phe Asp Asn Lys Ala His Ser Gly Arg Ile Pro
            260                 265                 270

Ile Ser Leu Glu Thr Gln Ala His Ile Gln Glu Cys Lys His Pro Ser
        275                 280                 285

Val Phe Gln His Gly Asp Asn Ser Phe Arg Leu Leu Phe Asp Val Val
    290                 295                 300

Val Ile Leu Thr Cys Ser Leu Ser Phe Leu Leu Cys Ala Arg Ser Leu
305                 310                 315                 320

Leu Arg Gly Phe Leu Leu Gln Asn Glu Phe Val Gly Phe Met Trp Arg
                325                 330                 335

Gln Arg Gly Arg Val Ile Ser Leu Trp Glu Arg Leu Glu Phe Val Asn
            340                 345                 350

Gly Trp Tyr Ile Leu Leu Val Thr Ser Asp Val Leu Thr Ile Ser Gly
        355                 360                 365
```

```
Thr Ile Met Lys Ile Gly Ile Glu Ala Lys Asn Leu Ala Ser Tyr Asp
    370                 375                 380

Val Cys Ser Ile Leu Leu Gly Thr Ser Thr Leu Leu Val Trp Val Gly
385                 390                 395                 400

Val Ile Arg Tyr Leu Thr Phe Phe His Asn Tyr Asn Ile Leu Ile Ala
                405                 410                 415

Thr Leu Arg Val Ala Leu Pro Ser Val Met Arg Phe Cys Cys Cys Val
            420                 425                 430

Ala Val Ile Tyr Leu Gly Tyr Cys Phe Cys Gly Trp Ile Val Leu Gly
        435                 440                 445

Pro Tyr His Val Lys Phe Arg Ser Leu Ser Met Val Ser Glu Cys Leu
    450                 455                 460

Phe Ser Leu Ile Asn Gly Asp Asp Met Phe Val Thr Phe Ala Ala Met
465                 470                 475                 480

Gln Ala Gln Gln Gly Arg Ser Ser Leu Val Trp Leu Phe Ser Gln Leu
                485                 490                 495

Tyr Leu Tyr Ser Phe Ile Ser Leu Phe Ile Tyr Met Val Leu Ser Leu
            500                 505                 510

Phe Ile Ala Leu Ile Thr Gly Ala Tyr Asp Thr Ile Lys His Pro Gly
        515                 520                 525

Gly Ala Gly Ala Glu Glu Ser Glu Leu Gln Ala Tyr Ile Ala Gln Cys
    530                 535                 540

Gln Asp Ser Pro Thr Ser Gly Lys Phe Arg Arg Gly Ser Gly Ser Ala
545                 550                 555                 560

Cys Ser Leu Leu Cys Cys Cys Gly Arg Asp Pro Ser Glu Glu His Ser
                565                 570                 575

Leu Leu Val Asn
            580
```

<210> SEQ ID NO 16
<211> LENGTH: 2051
<212> TYPE: DNA
<213> ORGANISM: homo sapiens

<400> SEQUENCE: 16

```
agatcagctg atgccggagg gtttgaagcc gcgccgcgag ggagcgaggt cgcagtgaca     60

gcggcgggcg atcggaccca ggctgccccg ccgtacccgc ctgcgtcccg cgctcccgcc    120

ccagcatgac agccccggcg ggtccgcgcg gctcagagac cgagcggctt ctgacccccca   180

accccgggta tgggacccag gcggggcctt caccggcccc tccgacaccc ccagaagagg    240

aagaccttcg ccgtcgtctc aaatactttt tcatgagtcc ctgcgacaag tttcgagcca    300

agggccgcaa gccctgcaag ctgatgctgc aagtggtcaa gatcctggtg gtcacggtgc    360

agctcatcct gtttgggctc agtaatcagc tggctgtgac attccgggaa gagaacacca    420

tcgccttccg acacctcttc ctgctgggct actcggacgg agcggatgac accttcgcag    480

cctacacgcg ggagcagctg taccaggcca tcttccatgc tgtggaccag tacctggcgt    540

tgcctgacgt gtcactgggc cggtatgcgt atgtccgtgg tgggggtgac ccttggacca    600

atggctcagg gcttgctctc tgccagcggt actaccaccg aggccacgtg gacccggcca    660

acgacacatt tgacattgat ccgatggtgg ttactgactg catccaggtg gatcccccccg   720

agcggccccc tccgcccccc agcgacgatc tcaccctctt ggaaagcagc tccagttaca    780

agaacctcac gctcaaattc cacaagctgg tcaatgtcac catccacttc cggctgaaga    840
```

```
ccattaacct ccagagcctc atcaataatg agatcccgga ctgctatacc ttcagcgtcc    900

tgatcacgtt tgacaacaaa gcacacagtg ggcggatccc catcagcctg gagacccagg    960

cccacatcca ggagtgtaag caccccagtg tcttccagca cggagacaac agcttccggc   1020

tcctgtttga cgtggtggtc atcctcacct gctccctgtc cttcctcctc tgcgcccgct   1080

cactccttcg aggcttcctg ctgcagaacg agtttgtggg gttcatgtgg cggcagcggg   1140

gacgggtcat cagcctgtgg gagcggctgg aatttgtcaa tggctggtac atcctgctcg   1200

tcaccagcga tgtgctcacc atctcgggca ccatcatgaa gatcggcatc gaggccaaga   1260

acttggcgag ctacgacgtc tgcagcatcc tcctgggcac ctcgacgctg ctggtgtggg   1320

tgggcgtgat ccgctacctg accttcttcc acaactacaa tatcctcatc gccacactgc   1380

gggtggccct gcccagcgtc atgcgcttct gctgctgcgt ggctgtcatc tacctgggct   1440

actgcttctg tggctggatc gtgctggggc cctatcatgt gaagttccgc tcactctcca   1500

tggtgtctga gtgcctgttc tcgctcatca atggggacga catgtttgtg acgttcgccg   1560

ccatgcaggc gcagcagggc cgcagcagcc tggtgtggct cttctcccag ctctaccttt   1620

actccttcat cagcctcttc atctacatgg tgctcagcct cttcatcgcg ctcatcaccg   1680

gcgcctacga caccatcaag catcccggcg gcgcaggcgc agaggagagc gagctgcagg   1740

cctacatcgc acagtgccag gacagcccca cctccggcaa gttccgccgc gggagcggct   1800

cggcctgcag ccttctctgc tgctgcggaa gggacccctc ggaggagcat tcgctgctgg   1860

tgaattgatt cgacctgact gccgttggac cgtaggccct ggactgcaga gacccccgcc   1920

cccgaccccg cttatttatt tgtagggttt gcttttaagg atcggctccc tgtcgcgccc   1980

gaggagggcc tggacctttc gtgtcggacc cttgggggcg gggagactgg gtggggaggg   2040

tgttgaataa a                                                        2051


<210> SEQ ID NO 17
<211> LENGTH: 663
<212> TYPE: PRT
<213> ORGANISM: homo sapiens

<400> SEQUENCE: 17

Met Thr Gly Ala Arg Ala Ser Ala Ala Glu Gln Arg Arg Ala Gly Arg
1               5                   10                  15

Ser Gly Gln Ala Arg Ala Ala Glu Arg Ala Ala Gly Met Ser Gly Ala
            20                  25                  30

Gly Arg Ala Leu Ala Ala Leu Leu Leu Ala Ala Ser Val Leu Ser Ala
        35                  40                  45

Ala Leu Leu Ala Pro Gly Gly Ser Ser Gly Arg Asp Ala Gln Ala Ala
    50                  55                  60

Pro Pro Arg Asp Leu Asp Lys Lys Arg His Ala Glu Leu Lys Met Asp
65                  70                  75                  80

Gln Ala Leu Leu Leu Ile His Asn Glu Leu Leu Trp Thr Asn Leu Thr
                85                  90                  95

Val Tyr Trp Lys Ser Glu Cys Cys Tyr His Cys Leu Phe Gln Val Leu
            100                 105                 110

Val Asn Val Pro Gln Ser Pro Lys Ala Gly Lys Pro Ser Ala Ala Ala
        115                 120                 125

Ala Ser Val Ser Thr Gln His Gly Ser Ile Leu Gln Leu Asn Asp Thr
    130                 135                 140

Leu Glu Glu Lys Glu Val Cys Arg Leu Glu Tyr Arg Phe Gly Glu Phe
145                 150                 155                 160
```

```
Gly Asn Tyr Ser Leu Leu Val Lys Asn Ile His Asn Gly Val Ser Glu
                165                 170                 175

Ile Ala Cys Asp Leu Ala Val Asn Glu Asp Pro Val Asp Ser Asn Leu
            180                 185                 190

Pro Val Ser Ile Ala Phe Leu Ile Gly Leu Ala Val Ile Ile Val Ile
        195                 200                 205

Ser Phe Leu Arg Leu Leu Leu Ser Leu Asp Asp Phe Asn Asn Trp Ile
    210                 215                 220

Ser Lys Ala Ile Ser Ser Arg Glu Thr Asp Arg Leu Ile Asn Ser Glu
225                 230                 235                 240

Leu Gly Ser Pro Ser Arg Thr Asp Pro Leu Asp Gly Asp Val Gln Pro
                245                 250                 255

Ala Thr Trp Arg Leu Ser Ala Leu Pro Pro Arg Leu Arg Ser Val Asp
            260                 265                 270

Thr Phe Arg Gly Ile Ala Leu Ile Leu Met Val Phe Val Asn Tyr Gly
        275                 280                 285

Gly Gly Lys Tyr Trp Tyr Phe Lys His Ala Ser Trp Asn Gly Leu Thr
    290                 295                 300

Val Ala Asp Leu Val Phe Pro Trp Phe Val Phe Ile Met Gly Ser Ser
305                 310                 315                 320

Ile Phe Leu Ser Met Thr Ser Ile Leu Gln Arg Gly Cys Ser Lys Phe
                325                 330                 335

Arg Leu Leu Gly Lys Ile Ala Trp Arg Ser Phe Leu Leu Ile Cys Ile
            340                 345                 350

Gly Ile Ile Ile Val Asn Pro Asn Tyr Cys Leu Gly Pro Leu Ser Trp
        355                 360                 365

Asp Lys Val Arg Ile Pro Gly Val Leu Gln Arg Leu Gly Val Thr Tyr
    370                 375                 380

Phe Val Val Ala Val Leu Glu Leu Leu Phe Ala Lys Pro Val Pro Glu
385                 390                 395                 400

His Cys Ala Ser Glu Arg Ser Cys Leu Ser Leu Arg Asp Ile Thr Ser
                405                 410                 415

Ser Trp Pro Gln Trp Leu Leu Ile Leu Val Leu Glu Gly Leu Trp Leu
            420                 425                 430

Gly Leu Thr Phe Leu Leu Pro Val Pro Gly Cys Pro Thr Gly Tyr Leu
        435                 440                 445

Gly Pro Gly Gly Ile Gly Asp Phe Gly Lys Tyr Pro Asn Cys Thr Gly
    450                 455                 460

Gly Ala Ala Gly Tyr Ile Asp Arg Leu Leu Leu Gly Asp Asp His Leu
465                 470                 475                 480

Tyr Gln His Pro Ser Ser Ala Val Leu Tyr His Thr Glu Val Ala Tyr
                485                 490                 495

Asp Pro Glu Gly Ile Leu Gly Thr Ile Asn Ser Ile Val Met Ala Phe
            500                 505                 510

Leu Gly Val Gln Ala Gly Lys Ile Leu Leu Tyr Tyr Lys Ala Arg Thr
        515                 520                 525

Lys Asp Ile Leu Ile Arg Phe Thr Ala Trp Cys Cys Ile Leu Gly Leu
    530                 535                 540

Ile Ser Val Ala Leu Thr Lys Val Ser Glu Asn Glu Gly Phe Ile Pro
545                 550                 555                 560

Val Asn Lys Asn Leu Trp Ser Leu Ser Tyr Val Thr Thr Leu Ser Ser
                565                 570                 575
```

```
Phe Ala Phe Phe Ile Leu Leu Val Leu Tyr Pro Val Val Asp Val Lys
            580                 585                 590

Gly Leu Trp Thr Gly Thr Pro Phe Phe Tyr Pro Gly Met Asn Ser Ile
        595                 600                 605

Leu Val Tyr Val Gly His Glu Val Phe Glu Asn Tyr Phe Pro Phe Gln
    610                 615                 620

Trp Lys Leu Lys Asp Asn Gln Ser His Lys Glu His Leu Thr Gln Asn
625                 630                 635                 640

Ile Val Ala Thr Ala Leu Trp Val Leu Ile Ala Tyr Ile Leu Tyr Arg
                645                 650                 655

Lys Lys Ile Phe Trp Lys Ile
            660


<210> SEQ ID NO 18
<211> LENGTH: 5228
<212> TYPE: DNA
<213> ORGANISM: homo sapiens

<400> SEQUENCE: 18

agggcggggc gcagcgggca ggcaagggcg gccgagcggg cggcgggcat gagcggggcg      60

ggcagggcgc tggccgcgct gctgctggcc gcgtccgtgc tgagcgccgc gctgctggcc     120

cccggcggct cttcggggcg cgatgcccag gccgcgccgc cacgagactt agacaaaaaa     180

agacatgcag agctgaagat ggatcaggct ttgctactca tccataatga acttctctgg     240

accaacttga ccgtctactg gaaatctgaa tgctgttatc actgcttgtt tcaggttctg     300

gtaaacgttc ctcagagtcc aaaagcaggg aagcctagtg ctgcagctgc ctctgtcagc     360

acccagcacg gatctatcct gcagctgaac gacaccttgg aagagaaaga agtttgtagg     420

ttggaataca gatttggaga atttggaaac tattctctct tggtaaagaa catccataat     480

ggagttagtg aaattgcctg tgacctggct gtgaacgagg atccagttga tagtaacctt     540

cctgtgagca ttgcattcct tattggtctt gctgtcatca ttgtgatatc ctttctgagg     600

ctcttgttga gtttggatga ctttaacaat tggatttcta aagccataag ttctcgagaa     660

actgatcgcc tcatcaattc tgagctggga tctcccagca ggacagaccc tctcgatggt     720

gatgttcagc cagcaacgtg gcgtctatct gccctgccgc cccgcctccg cagcgtggac     780

accttcaggg ggattgctct tatactcatg gtctttgtca attatggagg aggaaaatat     840

tggtacttca aacatgcaag ttggaatggg ctgacagtgg ctgacctcgt gttcccgtgg     900

tttgtattta ttatgggatc ttccattttt ctatcgatga cttctatact gcaacggggg     960

tgttcaaaat tcagattgct ggggaagatt gcatggagga gtttcctgtt aatctgcata    1020

ggaattatca ttgtgaatcc caattattgc cttggtccat tgtcttggga caaggtgcgc    1080

attcctggtg tgctgcagcg attgggagtg acatactttg tggttgctgt gttggagctc    1140

ctctttgcta aacctgtgcc tgaacattgt gcctcggaga ggagctgcct ttctcttcga    1200

gacatcacgt ccagctggcc ccagtggctg ctcatcctgg tgctggaagg cctgtggctg    1260

ggcttgacat tcctcctgcc agtccctggg tgccctactg gttatcttgg tcctgggggc    1320

attggagatt ttggcaagta tccaaattgc actggaggag ctgcaggcta catcgaccgc    1380

ctgctgctgg gagacgatca cctttaccag cacccatctt ctgctgtact ttaccacacc    1440

gaggtggcct atgaccccga gggcatcctg ggcaccatca actccatcgt gatggccttt    1500

ttaggagttc aggcaggaaa aatactattg tattacaagg ctcggaccaa agacatcctg    1560

attcgattca ctgcttggtg ttgtattctt gggctcattt ctgttgctct gacgaaggtt    1620
```

```
tctgaaaatg aaggctttat tccagtaaac aaaaatctct ggtccctttc gtatgtcact   1680
acgctcagtt cttttgcctt cttcatcctg ctggtcctgt acccagttgt ggatgtgaag   1740
gggctgtgga caggaacccc attcttttat ccaggaatga attccattct ggtatatgtc   1800
ggccacgagg tgtttgagaa ctacttcccc tttcagtgga agctgaagga caaccagtcc   1860
cacaaggagc acctgactca gaacatcgtc gccactgccc tctgggtgct cattgcctac   1920
atcctctata gaaagaagat tttttggaaa atctgatggc tcccactgag atgtgctgct   1980
ggaagactct agtaggcctg cagggaggac tgaagcagcc tttgttaaag ggaagcattc   2040
attaggaaat tgactggctg cgtgtttaca gactctgggg gaagacactg atgtcctcaa   2100
actggttaac tgtgacacgg ctcgccagaa ctctgcctgt ctatttgtga cttacagatt   2160
tgaaatgtaa ttgtcttttt tcctccatct tctgtggaaa tggatgtctt tggaacttca   2220
ttccgaggag ataagcttta actttccaaa agggaattgc catgggtgtt tttcttctgt   2280
ggtgagtgaa acaatctgag gtctggttct tgctgacctt gttgccctgc aaacttcctt   2340
tccacgtgta cgcgcacacc aacacgaaat gccatcactc ctactgcggc tgctatgaag   2400
cttactggtt gtgatgtgtt ataatttagt ctgttttttt gattgaatgc agtttaatgt   2460
ttccagaaag ccaaagtaat tttcttttca gatatgcaag gctttggtgg gtccaaaaaa   2520
tgtctatcac aagccatttt ttcctttcc tctctcgaaa agttaaaata tctatgtgtt   2580
attcccaaac cctcttacct atgtatctgc ctgtctgtcc atcatcttcc ttcctcccta   2640
tctctgtgta tctggatggc agccgctgcc caggggagtg gctgtgggga gggcaggtac   2700
tgtctttgcc tgtgggtcca gctgagccat ccctgctggg tgatgctggg caagaccctt   2760
ggcccgtctg ggccttggct tcctcacttg tgaaatgagc gggaagatga ctctcagttc   2820
cttccacctc ttagacatgg tgaggtaaca gacatcaaaa gcttttctga aatcttcaga   2880
agaaatagtt ccattacaga aaactcttca aaataaatag tagtgaaaac ttttaaaaac   2940
tctcattgga gtaagtcttt tcaagatgat cctccacaat ggaggcagcg ttcctacttg   3000
tcatcacaca gctgaagaca ttgtttctta ggtgtgaaat cggggacaaa ggacaaacag   3060
agacacacgg cattgttcat gggaggcatc gtcaccctcc tgggtgttct gtgggaattt   3120
cctgtgtgag gaaaacgtgg ccacagggtt gtgctgtacc caccccttccc cggcgagatg   3180
gccctcggcc tgtgccgctg cttccaccct cgccactcca tggcagcttt tggtctgttt   3240
ccggctctgc cctctgccct gaactctcat ccggcttgta cctgcctgct ggacccctcc   3300
acctggaggc cagcccatgt ctcaggccca gccctagcct cttctcctca aattctaagt   3360
gttttctctt taggtttccc tggctttgtg aatggatcat gtgtctctag gtataaacct   3420
gacatcatct ttccacccgg cttacctcca ccagatctcc ccagttctgt ctccatcttc   3480
tacctgcagc tgctctgttc tcatggtcac tgctgcatca ctgagtctgg acccttgtta   3540
tcattttcaa actggcctcc ttccctcgtt ccccacttct taaagtcacc tgtccattgc   3600
caccagatta agctttctcc agccagatca cctctctctg agaaacctcc attgacatgg   3660
aaacaccatt gtctggcaca catactcaca tactcacctt cccgtcttga tccccacaca   3720
tctttccagc ctcccctccc actccactcc ctgctctctc ctccacctcc ccatcctctt   3780
gtctcccctc ccctctgaat ccagcccagc ggggcttctc ctgcctccat cacatcacag   3840
aagtacctcc tgcttctggt tttaattaga gccttccccg attacatttt cctctgaatt   3900
ttttcctatc tacatttgat ctgtcatgtt taaacccccct acttctaagg gaacttctct   3960
```

```
aatctcttat cctcatcccc aaatagtgtt ttcttcctct gggttcttat aatgttggta   4020
tcaatctcac agcatttagt gcttcctgcc tggtgtgaca gttacctgtg tgcatgtgca   4080
atttctaatt tcccacgcta gactgtgagc ttcctaaggc aagaatcatg ccttgttggt   4140
ttctgtattc ctcatggtgc caaacacagt gccttctaca ttgcaggcgc tgaataaaca   4200
tttttaaagc aaaatgatgt ggatttttaa aataaatatt taagtgctgg taagatgagc   4260
atgtatccgg ggtgcccatg aaatgttctt ggggccgtgt ggggacagtc gtcattcctc   4320
ctcctgccac ccttttcttt cagtgagtca ctgtggatgg tcccagctgt gtcatcccaa   4380
agttcagcag ggaaagctga gctgggcctc tccaggtgag ttttctagaa gcatttctca   4440
aactgtgggt tacatcaact tgggtgtctt gagctgtaag gaaggaactc cggagtcagc   4500
tgggctacag gggagcttct ctaagtcctg cgggaggcca gacccagcct gagcttgctg   4560
ttagctagcg gaggcagctg ctggtggccc aggtgctcga caccaggcat cccctctcct   4620
cccacgaagg gtgtgccata atccccttca acaggaaatg cttcccagaa gcctctcagc   4680
agcctcccct cctgtcctat cagctagaag cgcctcgctt gtcccaagac cagcagggac   4740
agggaactgt ccgagcccgt ggctgtgtgg aggaaggcga cccccagcac aagattggtt   4800
tcctttggga agggaagagg gagtgtgttg gggtaagggg tagagcagag gaatggtcag   4860
ggggcaacaa ccgctgacag ctgcaacagg tgcatggcat ctcacaggga ggcagggagg   4920
tgcgagctcc taagtaatgg agcaaaaaaa ttctattctg tagaatgggg agagaaaatg   4980
tgacatttta attttttttt gcatttatat tcctaattcc tacttaaagt gaatatactg   5040
ccgctgtaga tcataaaatg tatcttttcc atggccaaca aggggcatct tttataaatg   5100
cataataacc cagtttgtat caaagggtat cgacttaagt gaaatttcaa catgctgtta   5160
ctttttcctt ttaatgtaat tctgttttcc aaataaatgg gggagacaaa tggaaaaaaa   5220
aaaaaaaa                                                            5228
```

<210> SEQ ID NO 19
<211> LENGTH: 1278
<212> TYPE: PRT
<213> ORGANISM: homo sapiens

<400> SEQUENCE: 19

```
Met Thr Ala Arg Gly Leu Ala Leu Gly Leu Leu Leu Leu Leu Leu Cys
1               5                   10                  15

Pro Ala Gln Val Phe Ser Gln Ser Cys Val Trp Tyr Gly Glu Cys Gly
            20                  25                  30

Ile Ala Tyr Gly Asp Lys Arg Tyr Asn Cys Glu Tyr Ser Gly Pro Pro
        35                  40                  45

Lys Pro Leu Pro Lys Asp Gly Tyr Asp Leu Val Gln Glu Leu Cys Pro
    50                  55                  60

Gly Phe Phe Phe Gly Asn Val Ser Leu Cys Cys Asp Val Arg Gln Leu
65                  70                  75                  80

Gln Thr Leu Lys Asp Asn Leu Gln Leu Pro Leu Gln Phe Leu Ser Arg
                85                  90                  95

Cys Pro Ser Cys Phe Tyr Asn Leu Leu Asn Leu Phe Cys Glu Leu Thr
            100                 105                 110

Cys Ser Pro Arg Gln Ser Gln Phe Leu Asn Val Thr Ala Thr Glu Asp
        115                 120                 125

Tyr Val Asp Pro Val Thr Asn Gln Thr Lys Thr Asn Val Lys Glu Leu
    130                 135                 140
```

```
Gln Tyr Tyr Val Gly Gln Ser Phe Ala Asn Ala Met Tyr Asn Ala Cys
145                 150                 155                 160

Arg Asp Val Glu Ala Pro Ser Ser Asn Asp Lys Ala Leu Gly Leu Leu
                165                 170                 175

Cys Gly Lys Asp Ala Asp Ala Cys Asn Ala Thr Asn Trp Ile Glu Tyr
            180                 185                 190

Met Phe Asn Lys Asp Asn Gly Gln Ala Pro Phe Thr Ile Thr Pro Val
        195                 200                 205

Phe Ser Asp Phe Pro Val His Gly Met Glu Pro Met Asn Asn Ala Thr
    210                 215                 220

Lys Gly Cys Asp Glu Ser Val Asp Glu Val Thr Ala Pro Cys Ser Cys
225                 230                 235                 240

Gln Asp Cys Ser Ile Val Cys Gly Pro Lys Pro Gln Pro Pro Pro Pro
                245                 250                 255

Pro Ala Pro Trp Thr Ile Leu Gly Leu Asp Ala Met Tyr Val Ile Met
            260                 265                 270

Trp Ile Thr Tyr Met Ala Phe Leu Leu Val Phe Phe Gly Ala Phe Phe
        275                 280                 285

Ala Val Trp Cys Tyr Arg Lys Arg Tyr Phe Val Ser Glu Tyr Thr Pro
    290                 295                 300

Ile Asp Ser Asn Ile Ala Phe Ser Val Asn Ala Ser Asp Lys Gly Glu
305                 310                 315                 320

Ala Ser Cys Cys Asp Pro Val Ser Ala Ala Phe Glu Gly Cys Leu Arg
                325                 330                 335

Arg Leu Phe Thr Arg Trp Gly Ser Phe Cys Val Arg Asn Pro Gly Cys
            340                 345                 350

Val Ile Phe Phe Ser Leu Val Phe Ile Thr Ala Cys Ser Ser Gly Leu
        355                 360                 365

Val Phe Val Arg Val Thr Thr Asn Pro Val Asp Leu Trp Ser Ala Pro
    370                 375                 380

Ser Ser Gln Ala Arg Leu Glu Lys Glu Tyr Phe Asp Gln His Phe Gly
385                 390                 395                 400

Pro Phe Phe Arg Thr Glu Gln Leu Ile Ile Arg Ala Pro Leu Thr Asp
                405                 410                 415

Lys His Ile Tyr Gln Pro Tyr Pro Ser Gly Ala Asp Val Pro Phe Gly
            420                 425                 430

Pro Pro Leu Asp Ile Gln Ile Leu His Gln Val Leu Asp Leu Gln Ile
        435                 440                 445

Ala Ile Glu Asn Ile Thr Ala Ser Tyr Asp Asn Glu Thr Val Thr Leu
    450                 455                 460

Gln Asp Ile Cys Leu Ala Pro Leu Ser Pro Tyr Asn Thr Asn Cys Thr
465                 470                 475                 480

Ile Leu Ser Val Leu Asn Tyr Phe Gln Asn Ser His Ser Val Leu Asp
                485                 490                 495

His Lys Lys Gly Asp Asp Phe Phe Val Tyr Ala Asp Tyr His Thr His
            500                 505                 510

Phe Leu Tyr Cys Val Arg Ala Pro Ala Ser Leu Asn Asp Thr Ser Leu
        515                 520                 525

Leu His Asp Pro Cys Leu Gly Thr Phe Gly Gly Pro Val Phe Pro Trp
    530                 535                 540

Leu Val Leu Gly Gly Tyr Asp Asp Gln Asn Tyr Asn Asn Ala Thr Ala
545                 550                 555                 560

Leu Val Ile Thr Phe Pro Val Asn Asn Tyr Tyr Asn Asp Thr Glu Lys
```

-continued

```
                565                 570                 575

Leu Gln Arg Ala Gln Ala Trp Glu Lys Glu Phe Ile Asn Phe Val Lys
            580                 585                 590

Asn Tyr Lys Asn Pro Asn Leu Thr Ile Ser Phe Thr Ala Glu Arg Ser
        595                 600                 605

Ile Glu Asp Glu Leu Asn Arg Glu Ser Asp Ser Asp Val Phe Thr Val
    610                 615                 620

Val Ile Ser Tyr Ala Ile Met Phe Leu Tyr Ile Ser Leu Ala Leu Gly
625                 630                 635                 640

His Ile Lys Ser Cys Arg Arg Leu Leu Val Asp Ser Lys Val Ser Leu
                645                 650                 655

Gly Ile Ala Gly Ile Leu Ile Val Leu Ser Ser Val Ala Cys Ser Leu
            660                 665                 670

Gly Val Phe Ser Tyr Ile Gly Leu Pro Leu Thr Leu Ile Val Ile Glu
        675                 680                 685

Val Ile Pro Phe Leu Val Leu Ala Val Gly Val Asp Asn Ile Phe Ile
    690                 695                 700

Leu Val Gln Ala Tyr Gln Arg Asp Glu Arg Leu Gln Gly Glu Thr Leu
705                 710                 715                 720

Asp Gln Gln Leu Gly Arg Val Leu Gly Glu Val Ala Pro Ser Met Phe
                725                 730                 735

Leu Ser Ser Phe Ser Glu Thr Val Ala Phe Phe Leu Gly Ala Leu Ser
            740                 745                 750

Val Met Pro Ala Val His Thr Phe Ser Leu Phe Ala Gly Leu Ala Val
        755                 760                 765

Phe Ile Asp Phe Leu Leu Gln Ile Thr Cys Phe Val Ser Leu Leu Gly
    770                 775                 780

Leu Asp Ile Lys Arg Gln Glu Lys Asn Arg Leu Asp Ile Phe Cys Cys
785                 790                 795                 800

Val Arg Gly Ala Glu Asp Gly Thr Ser Val Gln Ala Ser Glu Ser Cys
                805                 810                 815

Leu Phe Arg Phe Phe Lys Asn Ser Tyr Ser Pro Leu Leu Leu Lys Asp
            820                 825                 830

Trp Met Arg Pro Ile Val Ile Ala Ile Phe Val Gly Val Leu Ser Phe
        835                 840                 845

Ser Ile Ala Val Leu Asn Lys Val Asp Ile Gly Leu Asp Gln Ser Leu
    850                 855                 860

Ser Met Pro Asp Asp Ser Tyr Met Val Asp Tyr Phe Lys Ser Ile Ser
865                 870                 875                 880

Gln Tyr Leu His Ala Gly Pro Pro Val Tyr Phe Val Leu Glu Glu Gly
                885                 890                 895

His Asp Tyr Thr Ser Ser Lys Gly Gln Asn Met Val Cys Gly Gly Met
            900                 905                 910

Gly Cys Asn Asn Asp Ser Leu Val Gln Gln Ile Phe Asn Ala Ala Gln
        915                 920                 925

Leu Asp Asn Tyr Thr Arg Ile Gly Phe Ala Pro Ser Ser Trp Ile Asp
    930                 935                 940

Asp Tyr Phe Asp Trp Val Lys Pro Gln Ser Ser Cys Cys Arg Val Asp
945                 950                 955                 960

Asn Ile Thr Asp Gln Phe Cys Asn Ala Ser Val Val Asp Pro Ala Cys
                965                 970                 975

Val Arg Cys Arg Pro Leu Thr Pro Glu Gly Lys Gln Arg Pro Gln Gly
            980                 985                 990
```

```
Gly Asp Phe Met Arg Phe Leu Pro  Met Phe Leu Ser Asp  Asn Pro Asn
        995                 1000                 1005

Pro Lys  Cys Gly Lys Gly Gly  His Ala Ala Tyr Ser  Ser Ala Val
    1010                 1015                 1020

Asn Ile  Leu Leu Gly His Gly  Thr Arg Val Gly Ala  Thr Tyr Phe
    1025                 1030                 1035

Met Thr  Tyr His Thr Val Leu  Gln Thr Ser Ala Asp  Phe Ile Asp
    1040                 1045                 1050

Ala Leu  Lys Lys Ala Arg Leu  Ile Ala Ser Asn Val  Thr Glu Thr
    1055                 1060                 1065

Met Gly  Ile Asn Gly Ser Ala  Tyr Arg Val Phe Pro  Tyr Ser Val
    1070                 1075                 1080

Phe Tyr  Val Phe Tyr Glu Gln  Tyr Leu Thr Ile Ile  Asp Asp Thr
    1085                 1090                 1095

Ile Phe  Asn Leu Gly Val Ser  Leu Gly Ala Ile Phe  Leu Val Thr
    1100                 1105                 1110

Met Val  Leu Leu Gly Cys Glu  Leu Trp Ser Ala Val  Ile Met Cys
    1115                 1120                 1125

Ala Thr  Ile Ala Met Val Leu  Val Asn Met Phe Gly  Val Met Trp
    1130                 1135                 1140

Leu Trp  Gly Ile Ser Leu Asn  Ala Val Ser Leu Val  Asn Leu Val
    1145                 1150                 1155

Met Ser  Cys Gly Ile Ser Val  Glu Phe Cys Ser His  Ile Thr Arg
    1160                 1165                 1170

Ala Phe  Thr Val Ser Met Lys  Gly Ser Arg Val Glu  Arg Ala Glu
    1175                 1180                 1185

Glu Ala  Leu Ala His Met Gly  Ser Ser Val Phe Ser  Gly Ile Thr
    1190                 1195                 1200

Leu Thr  Lys Phe Gly Gly Ile  Val Val Leu Ala Phe  Ala Lys Ser
    1205                 1210                 1215

Gln Ile  Phe Gln Ile Phe Tyr  Phe Arg Met Tyr Leu  Ala Met Val
    1220                 1225                 1230

Leu Leu  Gly Ala Thr His Gly  Leu Ile Phe Leu Pro  Val Leu Leu
    1235                 1240                 1245

Ser Tyr  Ile Gly Pro Ser Val  Asn Lys Ala Lys Ser  Cys Ala Thr
    1250                 1255                 1260

Glu Glu  Arg Tyr Lys Gly Thr  Glu Arg Glu Arg Leu  Leu Asn Phe
    1265                 1270                 1275


<210> SEQ ID NO 20
<211> LENGTH: 4673
<212> TYPE: DNA
<213> ORGANISM: homo sapiens

<400> SEQUENCE: 20

tttgctcctg ctcctccgct cctcctgcgc ggggtgctga aacagcccgg ggaagtagag     60

ccgcctccgg ggagcccaac cagccgaacg ccgccggcgt cagcagcctt gcgcggccac    120

agcatgaccg ctcgcggcct ggcccttggc ctcctcctgc tgctactgtg tccagcgcag    180

gtgttttcac agtcctgtgt ttggtatgga gagtgtggaa ttgcatatgg ggacaagagg    240

tacaattgcg aatattctgg cccaccaaaa ccattgccaa aggatggata tgacttagtg    300

caggaactct gtccaggatt cttctttggc aatgtcagtc tctgttgtga tgttcggcag    360

cttcagacac taaaagacaa cctgcagctg cctctacagt ttctgtccag atgtccatcc    420
```

-continued

```
tgtttttata acctactgaa cctgttttgt gagctgacat gtagccctcg acagagtcag    480
tttttgaatg ttacagctac tgaagattat gttgatcctg ttacaaacca gacgaaaaca    540
aatgtgaaag agttacaata ctacgtcgga cagagttttg ccaatgcaat gtacaatgcc    600
tgccgggatg tggaggcccc ctcaagtaat gacaaggccc tgggactcct gtgtgggaag    660
gacgctgacg cctgtaatgc caccaactgg attgaataca tgttcaataa ggacaatgga    720
caggcacctt ttaccatcac tcctgtgttt tcagattttc cagtccatgg gatggagccc    780
atgaacaatg ccaccaaagg ctgtgacgag tctgtggatg aggtcacagc accatgtagc    840
tgccaagact gctctattgt ctgtggcccc aagccccagc cccacctcc tcctgctccc    900
tggacgatcc ttggcttgga cgccatgtat gtcatcatgt ggatcaccta catggcgttt    960
ttgcttgtgt tttttggagc attttttgca gtgtggtgct acagaaaacg gtattttgtc   1020
tccgagtaca ctcccatcga tagcaatata gctttttctg ttaatgcaag tgacaaagga   1080
gaggcgtcct gctgtgaccc tgtcagcgca gcatttgagg gctgcttgag gcggctgttc   1140
acacgctggg ggtctttctg cgtccgaaac cctggctgtg tcattttctt ctcgctggtc   1200
ttcattactg cgtgttcgtc aggcctggtg tttgtccggg tcacaaccaa tccagttgac   1260
ctctggtcag cccccagcag ccaggctcgc ctggaaaaag agtactttga ccagcacttt   1320
gggcctttct tccggacgga gcagctcatc atccgggccc ctctcactga caaacacatt   1380
taccagccat acccttcggg agctgatgta ccctttggac ctccgcttga catacagata   1440
ctgcaccagg ttcttgactt acaaatagcc atcgaaaaca ttactgcctc ttatgacaat   1500
gagactgtga cacttcaaga catctgcttg gcccctcttt caccgtataa cacgaactgc   1560
accattttga gtgtgttaaa ttacttccag aacagccatt ccgtgctgga ccacaagaaa   1620
ggggacgact tctttgtgta tgccgattac cacacgcact ttctgtactg cgtacgggct   1680
cctgcctctc tgaatgatac aagtttgctc catgaccctt gtctgggtac gtttggtgga   1740
ccagtgttcc cgtggcttgt gttgggaggc tatgatgatc aaaactacaa taacgccact   1800
gcccttgtga ttaccttccc tgtcaataat tactataatg atacagagaa gctccagagg   1860
gcccaggcct gggaaaaaga gtttattaat tttgtgaaaa actacaagaa tcccaatctg   1920
accatttcct tcactgctga acgaagtatt gaagatgaac taaatcgtga aagtgacagt   1980
gatgtcttca ccgttgtaat tagctatgcc atcatgtttc tatatatttc cctagccttg   2040
gggcacatca aaagctgtcg caggcttctg gtggattcga aggtctcact aggcatcgcg   2100
ggcatcttga tcgtgctgag ctcggtggct tgctccttgg gtgtcttcag ctacattggg   2160
ttgcccttga ccctcattgt gattgaagtc atcccgttcc tggtgctggc tgttggagtg   2220
gacaacatct tcattctggt gcaggcctac cagagagatg aacgtcttca aggggaaacc   2280
ctggatcagc agctgggcag ggtcctagga gaagtggctc ccagtatgtt cctgtcatcc   2340
ttttctgaga ctgtagcatt tttcttagga gcattgtccg tgatgccagc cgtgcacacc   2400
ttctctctct ttgcgggatt ggcagtcttc attgactttc ttctgcagat tacctgtttc   2460
gtgagtctct tggggttaga cattaaacgt caagagaaaa atcggctaga catcttttgc   2520
tgtgtcagag gtgctgaaga tggaacaagc gtccaggcct cagagagctg tttgtttcgc   2580
ttcttcaaaa actcctattc tccacttctg ctaaaggact ggatgagacc aattgtgata   2640
gcaatatttg tgggtgttct gtcattcagc atcgcagtcc tgaacaaagt agatattgga   2700
ttggatcagt ctctttcgat gccagatgac tcctacatgg tggattattt caaatccatc   2760
```

```
agtcagtacc tgcatgcggg tccgcctgtg tactttgtcc tggaggaagg gcacgactac   2820

acttcttcca aggggcagaa catggtgtgc ggcggcatgg gctgcaacaa tgattccctg   2880

gtgcagcaga tatttaacgc ggcgcagctg gacaactata cccgaatagg cttcgccccc   2940

tcgtcctgga tcgacgatta tttcgactgg gtgaagccac agtcgtcttg ctgtcgagtg   3000

gacaatatca ctgaccagtt ctgcaatgct tcagtggttg accctgcctg cgttcgctgc   3060

aggcctctga ctccggaagg caaacagagg cctcaggggg gagacttcat gagattcctg   3120

cccatgttcc tttcggataa ccctaacccc aagtgtggca aagggggaca tgctgcctat   3180

agttctgcag ttaacatcct ccttggccat ggcaccaggg tcggagccac gtacttcatg   3240

acctaccaca ccgtgctgca gacctctgct gactttattg acgctctgaa gaaagcccga   3300

cttatagcca gtaatgtcac cgaaaccatg ggcattaacg gcagtgccta ccgagtattt   3360

ccttacagtg tgttttatgt cttctacgaa cagtacctga ccatcattga cgacactatc   3420

ttcaacctcg gtgtgtccct gggcgcgata tttctggtga ccatggtcct cctgggctgt   3480

gagctctggt ctgcagtcat catgtgtgcc accatcgcca tggtcttggt caacatgttt   3540

ggagttatgt ggctctgggg catcagtctg aacgctgtat ccttggtcaa cctggtgatg   3600

agctgtggca tctccgtgga gttctgcagc cacataacca gagcgttcac ggtgagcatg   3660

aaaggcagcc gcgtggagcg cgcggaagag gcacttgccc acatgggcag ctccgtgttc   3720

agtggaatca cacttacaaa atttggaggg attgtggtgt tggcttttgc caaatctcaa   3780

attttccaga tattctactt caggatgtat ttggccatgg tcttactggg agccactcac   3840

ggattaatat ttctccctgt cttactcagt tacatagggc catcagtaaa taaagccaaa   3900

agttgtgcca ctgaagagcg atacaaagga acagagcgcg aacggcttct aaatttctag   3960

ccctctcgca gggcatcctg actgaactgt gtctaagggt cggtcggttt accactggac   4020

gggtgctgca tcggcaaggc caagttgaac accggatggt gccaaccatc ggttgtttgg   4080

cagcagcttt gaacgtagcg cctgtgaact caggaatgca cagttgactt gggaagcagt   4140

attactagat ctggaggcaa ccacaggaca ctaaacttct cccagcctct tcaggaaaga   4200

aacctcattc tttggcaagc aggaggtgac actagatggc tgtgaatgtg atccgctcac   4260

tgacactctg taaaggccaa tcaatgcact gtctgtcctc tcctttttag gagtaagcca   4320

tcccacaagt tctataccat atttttagtg acagttgagg ttgtagatac actttataac   4380

attttatagt ttaaagagct ttattaatgc aataaattaa ctttgtacac atttttatat   4440

aaaaaaacag caagtgattt cagaatgttg taggcctcat tagagcttgg tctccaaaaa   4500

tctgtttgaa aaaagcaaca tgttcttcac agtgttcccc tagaaaggaa gagatttaat   4560

tgccagttag atgtggcatg aaatgaggga caaagaaagc atctcgtagg tgtgtctact   4620

gggttttaac ttatttttct ttaataaaat acattgtttt cctaaaaaaa aaa          4673
```

```
<210> SEQ ID NO 21
<211> LENGTH: 410
<212> TYPE: PRT
<213> ORGANISM: homo sapiens

<400> SEQUENCE: 21

Met Val Cys Phe Arg Leu Phe Pro Val Pro Gly Ser Gly Leu Val Leu
1               5                   10                  15

Val Cys Leu Val Leu Gly Ala Val Arg Ser Tyr Ala Leu Glu Leu Asn
            20                  25                  30

Leu Thr Asp Ser Glu Asn Ala Thr Cys Leu Tyr Ala Lys Trp Gln Met
```

```
        35                  40                  45

Asn Phe Thr Val Arg Tyr Glu Thr Thr Asn Lys Thr Tyr Lys Thr Val
    50                  55                  60

Thr Ile Ser Asp His Gly Thr Val Thr Tyr Asn Gly Ser Ile Cys Gly
65                  70                  75                  80

Asp Asp Gln Asn Gly Pro Lys Ile Ala Val Gln Phe Gly Pro Gly Phe
                85                  90                  95

Ser Trp Ile Ala Asn Phe Thr Lys Ala Ala Ser Thr Tyr Ser Ile Asp
            100                 105                 110

Ser Val Ser Phe Ser Tyr Asn Thr Gly Asp Asn Thr Thr Phe Pro Asp
        115                 120                 125

Ala Glu Asp Lys Gly Ile Leu Thr Val Asp Glu Leu Leu Ala Ile Arg
    130                 135                 140

Ile Pro Leu Asn Asp Leu Phe Arg Cys Asn Ser Leu Ser Thr Leu Glu
145                 150                 155                 160

Lys Asn Asp Val Val Gln His Tyr Trp Asp Val Leu Val Gln Ala Phe
                165                 170                 175

Val Gln Asn Gly Thr Val Ser Thr Asn Glu Phe Leu Cys Asp Lys Asp
            180                 185                 190

Lys Thr Ser Thr Val Ala Pro Thr Ile His Thr Thr Val Pro Ser Pro
        195                 200                 205

Thr Thr Thr Pro Thr Pro Lys Glu Lys Pro Glu Ala Gly Thr Tyr Ser
    210                 215                 220

Val Asn Asn Gly Asn Asp Thr Cys Leu Leu Ala Thr Met Gly Leu Gln
225                 230                 235                 240

Leu Asn Ile Thr Gln Asp Lys Val Ala Ser Val Ile Asn Ile Asn Pro
                245                 250                 255

Asn Thr Thr His Ser Thr Gly Ser Cys Arg Ser His Thr Ala Leu Leu
            260                 265                 270

Arg Leu Asn Ser Ser Thr Ile Lys Tyr Leu Asp Phe Val Phe Ala Val
        275                 280                 285

Lys Asn Glu Asn Arg Phe Tyr Leu Lys Glu Val Asn Ile Ser Met Tyr
    290                 295                 300

Leu Val Asn Gly Ser Val Phe Ser Ile Ala Asn Asn Asn Leu Ser Tyr
305                 310                 315                 320

Trp Asp Ala Pro Leu Gly Ser Ser Tyr Met Cys Asn Lys Glu Gln Thr
                325                 330                 335

Val Ser Val Ser Gly Ala Phe Gln Ile Asn Thr Phe Asp Leu Arg Val
            340                 345                 350

Gln Pro Phe Asn Val Thr Gln Gly Lys Tyr Ser Thr Ala Gln Asp Cys
        355                 360                 365

Ser Ala Asp Asp Asp Asn Phe Leu Val Pro Ile Ala Val Gly Ala Ala
    370                 375                 380

Leu Ala Gly Val Leu Ile Leu Val Leu Leu Ala Tyr Phe Ile Gly Leu
385                 390                 395                 400

Lys His His His Ala Gly Tyr Glu Gln Phe
                405                 410


<210> SEQ ID NO 22
<211> LENGTH: 1868
<212> TYPE: DNA
<213> ORGANISM: homo sapiens

<400> SEQUENCE: 22
```

```
ccgattcctg gcttttgcaa ggctgtggtc ggtggtcatc agtgctcttg acccaggtcc     60

agcgagcctt ttccctggtg ttgcagctgt tgttgtaccg ccgccgtcgc cgccgtcgcc    120

gcctgctctg cggggtcatg gtgtgcttcc gcctcttccc ggttccgggc tcagggctcg    180

ttctggtctg cctagtcctg ggagctgtgc ggtcttatgc attggaactt aatttgacag    240

attcagaaaa tgccacttgc ctttatgcaa aatggcagat gaatttcaca gtacgctatg    300

aaactacaaa taaaacttat aaaactgtaa ccatttcaga ccatggcact gtgacatata    360

atggaagcat ttgtggggat gatcagaatg gtcccaaaat agcagtgcag ttcggacctg    420

gcttttcctg gattgcgaat tttaccaagg cagcatctac ttattcaatt gacagcgtct    480

cattttccta caacactggt gataacacaa catttcctga tgctgaagat aaaggaattc    540

ttactgttga tgaacttttg gccatcagaa ttccattgaa tgaccttttt agatgcaata    600

gtttatcaac tttggaaaag aatgatgttg tccaacacta ctgggatgtt cttgtacaag    660

cttttgtcca aaatggcaca gtgagcacaa atgagttcct gtgtgataaa gacaaaactt    720

caacagtggc acccaccata cacaccactg tgccatctcc tactacaaca cctactccaa    780

aggaaaaacc agaagctgga acctattcag ttaataatgg caatgatact tgtctgctgg    840

ctaccatggg gctgcagctg aacatcactc aggataaggt tgcttcagtt attaacatca    900

accccaatac aactcactcc acaggcagct gccgttctca cactgctcta cttagactca    960

atagcagcac cattaagtat ctagactttg tctttgctgt gaaaaatgaa aaccgatttt   1020

atctgaagga agtgaacatc agcatgtatt tggttaatgg ctccgttttc agcattgcaa   1080

ataacaatct cagctactgg gatgcccccc tgggaagttc ttatatgtgc aacaaagagc   1140

agactgtttc agtgtctgga gcatttcaga taaatacctt tgatctaagg gttcagcctt   1200

tcaatgtgac acaaggaaag tattctacag ctcaagactg cagtgcagat gacgacaact   1260

tccttgtgcc catagcggtg ggagctgcct tggcaggagt acttattcta gtgttgctgg   1320

cttattttat tggtctcaag caccatcatg ctggatatga gcaattttag aatctgcaac   1380

ctgattgatt atataaaaat acatgcaaat aacaagattt tcttacctct cagttgttga   1440

aacactttgc ttcttaaaat tgatatgttg aaactttaat tcttttatca atcccagcat   1500

tttgagatca gtctttatta ataaaacctg ttctctttaa tcagcttaaa atccaaagtg   1560

tcatatttac tggtcctgga gacaaacttg ttcaaaagaa catcaacgtg caatgtttta   1620

aggtctatct taagaagccc tggccaaatt ttgatcctaa ccttgaagta tgccttgaac   1680

ttattaacat ggccattata agaataaaat atgtagttgt gtcttaatgg aattaataaa   1740

tgtcatttca ctactggtgt tctgttttca atgtataagg actatagtga tttaaactca   1800

tcaatgtgcc tttgcataaa gttgattaaa taaatattga tgtggtataa atgcccatca   1860

gatatgct                                                            1868
```

<210> SEQ ID NO 23
<211> LENGTH: 410
<212> TYPE: PRT
<213> ORGANISM: homo sapiens

<400> SEQUENCE: 23

```
Met Val Cys Phe Arg Leu Phe Pro Val Pro Gly Ser Gly Leu Val Leu
1               5                   10                  15

Val Cys Leu Val Leu Gly Ala Val Arg Ser Tyr Ala Leu Glu Leu Asn
            20                  25                  30

Leu Thr Asp Ser Glu Asn Ala Thr Cys Leu Tyr Ala Lys Trp Gln Met
```

```
        35                  40                  45

Asn Phe Thr Val Arg Tyr Glu Thr Thr Asn Lys Thr Tyr Lys Thr Val
    50                  55                  60

Thr Ile Ser Asp His Gly Thr Val Thr Tyr Asn Gly Ser Ile Cys Gly
65                  70                  75                  80

Asp Asp Gln Asn Gly Pro Lys Ile Ala Val Gln Phe Gly Pro Gly Phe
                85                  90                  95

Ser Trp Ile Ala Asn Phe Thr Lys Ala Ala Ser Thr Tyr Ser Ile Asp
            100                 105                 110

Ser Val Ser Phe Ser Tyr Asn Thr Gly Asp Asn Thr Thr Phe Pro Asp
        115                 120                 125

Ala Glu Asp Lys Gly Ile Leu Thr Val Asp Glu Leu Leu Ala Ile Arg
    130                 135                 140

Ile Pro Leu Asn Asp Leu Phe Arg Cys Asn Ser Leu Ser Thr Leu Glu
145                 150                 155                 160

Lys Asn Asp Val Val Gln His Tyr Trp Asp Val Leu Val Gln Ala Phe
                165                 170                 175

Val Gln Asn Gly Thr Val Ser Thr Asn Glu Phe Leu Cys Asp Lys Asp
            180                 185                 190

Lys Thr Ser Thr Val Ala Pro Thr Ile His Thr Thr Val Pro Ser Pro
        195                 200                 205

Thr Thr Thr Pro Thr Pro Lys Glu Lys Pro Glu Ala Gly Thr Tyr Ser
    210                 215                 220

Val Asn Asn Gly Asn Asp Thr Cys Leu Leu Ala Thr Met Gly Leu Gln
225                 230                 235                 240

Leu Asn Ile Thr Gln Asp Lys Val Ala Ser Val Ile Asn Ile Asn Pro
                245                 250                 255

Asn Thr Thr His Ser Thr Gly Ser Cys Arg Ser His Thr Ala Leu Leu
            260                 265                 270

Arg Leu Asn Ser Ser Thr Ile Lys Tyr Leu Asp Phe Val Phe Ala Val
        275                 280                 285

Lys Asn Glu Asn Arg Phe Tyr Leu Lys Glu Val Asn Ile Ser Met Tyr
    290                 295                 300

Leu Val Asn Gly Ser Val Phe Ser Ile Ala Asn Asn Asn Leu Ser Tyr
305                 310                 315                 320

Trp Asp Ala Pro Leu Gly Ser Ser Tyr Met Cys Asn Lys Glu Gln Thr
                325                 330                 335

Val Ser Val Ser Gly Ala Phe Gln Ile Asn Thr Phe Asp Leu Arg Val
            340                 345                 350

Gln Pro Phe Asn Val Thr Gln Gly Lys Tyr Ser Thr Ala Gln Glu Cys
        355                 360                 365

Ser Leu Asp Asp Asp Thr Ile Leu Ile Pro Ile Ile Val Gly Ala Gly
    370                 375                 380

Leu Ser Gly Leu Ile Ile Val Ile Val Ile Ala Tyr Val Ile Gly Arg
385                 390                 395                 400

Arg Lys Ser Tyr Ala Gly Tyr Gln Thr Leu
                405                 410
```

<210> SEQ ID NO 24
<211> LENGTH: 4006
<212> TYPE: DNA
<213> ORGANISM: homo sapiens

<400> SEQUENCE: 24

-continued

```
ccgattcctg gcttttgcaa ggctgtggtc ggtggtcatc agtgctcttg acccaggtcc     60
agcgagcctt ttccctggtg ttgcagctgt tgttgtaccg ccgccgtcgc cgccgtcgcc    120
gcctgctctg cggggtcatg gtgtgcttcc gcctcttccc ggttccgggc tcagggctcg    180
ttctggtctg cctagtcctg ggagctgtgc ggtcttatgc attggaactt aatttgacag    240
attcagaaaa tgccacttgc ctttatgcaa aatggcagat gaatttcaca gtacgctatg    300
aaactacaaa taaaacttat aaaactgtaa ccatttcaga ccatggcact gtgacatata    360
atggaagcat ttgtggggat gatcagaatg gtcccaaaat agcagtgcag ttcggacctg    420
gcttttcctg gattgcgaat tttaccaagg cagcatctac ttattcaatt gacagcgtct    480
cattttccta caacactggt gataacacaa catttcctga tgctgaagat aaaggaattc    540
ttactgttga tgaacttttg gccatcagaa ttccattgaa tgaccttttt agatgcaata    600
gtttatcaac tttggaaaag aatgatgttg tccaacacta ctgggatgtt cttgtacaag    660
cttttgtcca aaatggcaca gtgagcacaa atgagttcct gtgtgataaa gacaaaactt    720
caacagtggc acccaccata cacaccactg tgccatctcc tactacaaca cctactccaa    780
aggaaaaacc agaagctgga acctattcag ttaataatgg caatgatact tgtctgctgg    840
ctaccatggg gctgcagctg aacatcactc aggataaggt tgcttcagtt attaacatca    900
accccaatac aactcactcc acaggcagct gccgttctca cactgctcta cttagactca    960
atagcagcac cattaagtat ctagactttg tctttgctgt gaaaaatgaa aaccgatttt   1020
atctgaagga agtgaacatc agcatgtatt tggttaatgg ctccgttttc agcattgcaa   1080
ataacaatct cagctactgg gatgcccccc tgggaagttc ttatatgtgc aacaaagagc   1140
agactgtttc agtgtctgga gcatttcaga taaatacctt tgatctaagg gttcagcctt   1200
tcaatgtgac acaaggaaag tattctacag cccaagagtg ttcgctggat gatgacacca   1260
ttctaatccc aattatagtt ggtgctggtc tttcaggctt gattatcgtt atagtgattg   1320
cttacgtaat tggcagaaga aaaagttatg ctggatatca gactctgtaa cactaatcaa   1380
tacgtgatct ctgttacaaa agaaaaaagc aagtacaagt tccaacatgc aatactggtc   1440
aacttaaggt atatttagtt gcagtccagc tctttagaat gggtggtatg gggatttca    1500
aacttaaaca aaaaactatc aactacaaat tagttgcctg actttggttt ttccaaccaa   1560
ggaatttaaa actgttattt ttacagcaaa agatgtgcaa aatcactgga ttataagttc   1620
tattttactg tcttgaatta gtatttcagt gttttcattt tagacattca gactaaaaat   1680
acaccgttta gaaaaaacaa tttttgaaaa agagattttt tttccctgca ggtagttgag   1740
ttgaacaaca tgttctaccg tggatttgta cttgctcctt ttgctctttt tgtgtgtgtg   1800
tgtgtgtgtg tgtgtgtgtg tgtgattttt gtttgcaggt taacttagct actttggcat   1860
tgctgcatat ttgacctttg agagatataa tagtagattt gaacaggggc tggtattatt   1920
atgttcttag caataaatgc ttttctaatg ccttttgaat acatttgtat ttatgtggct   1980
gtaatgacaa aagatacaaa agctttttaa aatttagagt aggtattaat cttattgttt   2040
aatctttttt ttaaaaaaac tggatatttc aatcttttaa attgcaatat ataagactat   2100
tccaactggg catttcaatc catttttag gtgctttaga gataattgct tgccagtgcc   2160
aattgagggc attagtactt tgtgctcata aattggcctc tgtatgcagt actaaaatta   2220
atgcagattt ctctttagcc ttccaacatt tcttgttgat agtgatgtat tttattattt   2280
tctttttctt aagaaatgcc agtgtgtcct agaacctaga taacgaagtg cacttacact   2340
tataaaataa cttgcatcta ggctgggcgt ggcggctcac gcctgtaatc ccagcacttt   2400
```

```
gggaggccga agtgggtgga tcacttgagg ccaggagttt gagaccagcc tggccaacat   2460

ggtgaaaccc catctctatc agaaatacaa aaaattagct gggcatggtg gtgggcgcct   2520

gtaatcccag ttactcggga ggctgaggca ggagaatcac ttgaacccgg gaggcagagg   2580

ttgcggtgag ccaagagcgc accattgcac tccagccttg ggcgacaaaa acgaaactcc   2640

atcttcaaaa caaaacaaaa caaaacaaac aaacaaacaa aacttgcatc ttaaccaaaa   2700

gtcttggttt tatcttaatc cattaaaagt tggtcttgtt tccagcttgc attgattgct   2760

acaacatcac taatttggct ttcacattta aatggttctg tgctaatcaa aactttcgtt   2820

gttattattc gttatggtag aatcattttt aattcacgtg ctttgtgttc agttttgtgg   2880

tctgagagat gtaccaattg tcaaattacc gtgtaccacc taatgtttat aggagaaagc   2940

aaaatacatc agcttggtag ttaacacatc aaatatttct tgctgcttct aggagaactt   3000

ttttggtgtg tgttggaatg gctgagcaaa tattaaaatt gttaatatgc agccatatat   3060

ggaaggttcc tgtggggttg ttttttcgtg tttttttttt ttgtggtggg attatgtgcc   3120

tcccattcac tagaaaatga gaaaattgtc tgggttccaa aatattgaca ttgaatggat   3180

caatacacac acacagacat atatatatat atatgcacac atatataggc agttgcatgc   3240

ctagcatggg tattttataa ccatataact gagttatatt ggaattataa atattttccg   3300

tcacttaaat ttgttctttg tttagcctga aaacctttat ggctcaagat cagattcctg   3360

actaacccct ctcttagagc tacagcgagc tgcattacca gcttaaaaca cttcttaggg   3420

attaaatata gatgtaattt ttcaaaatcg tttttaattt aaactgtgtt ttagtgtaaa   3480

attgttaacc ttgtaagatg gataatgtgt ataagaatgt aggccttaac tatttcacat   3540

gagtcaaaac aaagcagctt taaaaaaata attggaagca caatgcatgg cactgactga   3600

atgctgttaa tatttctaaa agtttctaca ttcagattat atgcctgatt catagtaaaa   3660

tacctctaat aaacactgtt ttatagaaaa cctgacttca gtgaatattt ttgtatttta   3720

catgggccag tttatatact gctatttaca ctattatttc ctatagctac atgttctttg   3780

taccttttgt agttttattt gtattactag attcatacct tgatggtaac gctctatctg   3840

gttttgggtg tttttcatgt tttagcattt gtataaagaa actggtccat gtaaatactt   3900

tccatgtttt ttcttcaaat gtttaaacca ctagttgatg tatggtatct ttagatattt   3960

gcctgtctgt ttgctcaaaa ttgcttctaa aacaataaag attctt                  4006
```

```
<210> SEQ ID NO 25
<211> LENGTH: 411
<212> TYPE: PRT
<213> ORGANISM: homo sapiens

<400> SEQUENCE: 25

Met Val Cys Phe Arg Leu Phe Pro Val Pro Gly Ser Gly Leu Val Leu
1               5                   10                  15

Val Cys Leu Val Leu Gly Ala Val Arg Ser Tyr Ala Leu Glu Leu Asn
            20                  25                  30

Leu Thr Asp Ser Glu Asn Ala Thr Cys Leu Tyr Ala Lys Trp Gln Met
        35                  40                  45

Asn Phe Thr Val Arg Tyr Glu Thr Thr Asn Lys Thr Tyr Lys Thr Val
    50                  55                  60

Thr Ile Ser Asp His Gly Thr Val Thr Tyr Asn Gly Ser Ile Cys Gly
65                  70                  75                  80

Asp Asp Gln Asn Gly Pro Lys Ile Ala Val Gln Phe Gly Pro Gly Phe
```

```
                85                  90                  95

Ser Trp Ile Ala Asn Phe Thr Lys Ala Ala Ser Thr Tyr Ser Ile Asp
            100                 105                 110

Ser Val Ser Phe Ser Tyr Asn Thr Gly Asp Asn Thr Thr Phe Pro Asp
        115                 120                 125

Ala Glu Asp Lys Gly Ile Leu Thr Val Asp Glu Leu Leu Ala Ile Arg
    130                 135                 140

Ile Pro Leu Asn Asp Leu Phe Arg Cys Asn Ser Leu Ser Thr Leu Glu
145                 150                 155                 160

Lys Asn Asp Val Val Gln His Tyr Trp Asp Val Leu Val Gln Ala Phe
                165                 170                 175

Val Gln Asn Gly Thr Val Ser Thr Asn Glu Phe Leu Cys Asp Lys Asp
            180                 185                 190

Lys Thr Ser Thr Val Ala Pro Thr Ile His Thr Thr Val Pro Ser Pro
        195                 200                 205

Thr Thr Thr Pro Thr Pro Lys Glu Lys Pro Glu Ala Gly Thr Tyr Ser
    210                 215                 220

Val Asn Asn Gly Asn Asp Thr Cys Leu Leu Ala Thr Met Gly Leu Gln
225                 230                 235                 240

Leu Asn Ile Thr Gln Asp Lys Val Ala Ser Val Ile Asn Ile Asn Pro
                245                 250                 255

Asn Thr Thr His Ser Thr Gly Ser Cys Arg Ser His Thr Ala Leu Leu
            260                 265                 270

Arg Leu Asn Ser Ser Thr Ile Lys Tyr Leu Asp Phe Val Phe Ala Val
        275                 280                 285

Lys Asn Glu Asn Arg Phe Tyr Leu Lys Glu Val Asn Ile Ser Met Tyr
    290                 295                 300

Leu Val Asn Gly Ser Val Phe Ser Ile Ala Asn Asn Asn Leu Ser Tyr
305                 310                 315                 320

Trp Asp Ala Pro Leu Gly Ser Ser Tyr Met Cys Asn Lys Glu Gln Thr
                325                 330                 335

Val Ser Val Ser Gly Ala Phe Gln Ile Asn Thr Phe Asp Leu Arg Val
            340                 345                 350

Gln Pro Phe Asn Val Thr Gln Gly Lys Tyr Ser Thr Ala Glu Glu Cys
        355                 360                 365

Ser Ala Asp Ser Asp Leu Asn Phe Leu Ile Pro Val Ala Val Gly Val
    370                 375                 380

Ala Leu Gly Phe Leu Ile Ile Val Val Phe Ile Ser Tyr Met Ile Gly
385                 390                 395                 400

Arg Arg Lys Ser Arg Thr Gly Tyr Gln Ser Val
                405                 410


<210> SEQ ID NO 26
<211> LENGTH: 1236
<212> TYPE: DNA
<213> ORGANISM: homo sapiens

<400> SEQUENCE: 26

atggtgtgct tccgcctctt cccggttccg ggctcagggc tcgttctggt ctgcctagtc      60

ctgggagctg tgcggtctta tgcattggaa cttaatttga cagattcaga aaatgccact     120

tgcctttatg caaaatggca gatgaatttc acagtacgct atgaaactac aaataaaact     180

tataaaactg taaccatttc agaccatggc actgtgacat ataatggaag catttgtggg     240

gatgatcaga atggtcccaa aatagcagtg cagttcggac ctggcttttc ctggattgcg     300
```

-continued

```
aattttacca aggcagcatc tacttattca attgacagcg tctcattttc ctacaacact    360

ggtgataaca caacatttcc tgatgctgaa gataaaggaa ttcttactgt tgatgaactt    420

ttggccatca gaattccatt gaatgacctt tttagatgca atagtttatc aactttggaa    480

aagaatgatg ttgtccaaca ctactgggat gttcttgtac aagcttttgt ccaaaatggc    540

acagtgagca caaatgagtt cctgtgtgat aaagacaaaa cttcaacagt ggcacccacc    600

atacacacca ctgtgccatc tcctactaca acacctactc caaaggaaaa accagaagct    660

ggaacctatt cagttaataa tggcaatgat acttgtctgc tggctaccat ggggctgcag    720

ctgaacatca ctcaggataa ggttgcttca gttattaaca tcaaccccaa tacaactcac    780

tccacaggca gctgccgttc tcacactgct ctacttagac tcaatagcag caccattaag    840

tatctagact ttgtctttgc tgtgaaaaat gaaaaccgat tttatctgaa ggaagtgaac    900

atcagcatgt atttggttaa tggctccgtt ttcagcattg caaataacaa tctcagctac    960

tgggatgccc ccctgggaag ttcttatatg tgcaacaaag agcagactgt ttcagtgtct   1020

ggagcatttc agataaatac ctttgatcta agggttcagc ctttcaatgt gacacaagga   1080

aagtattcta cagctgaaga atgttctgct gactctgacc tcaactttct tattcctgtt   1140

gcagtgggtg tggccttggg cttccttata attgttgtct ttatctctta tatgattgga   1200

agaaggaaaa gtcgtactgg ttatcagtct gtgtaa                              1236

<210> SEQ ID NO 27
<211> LENGTH: 6
<212> TYPE: PRT
<213> ORGANISM: Artificial Sequence
<220> FEATURE:
<223> OTHER INFORMATION: Synthetic construct

<400> SEQUENCE: 27

His His His His His His
1               5
```

METHODS OF TREATING LYSOSOMAL DISORDERS

CROSS REFERENCE TO RELATED APPLICATION(S)

This application is a US national phase application under 35 U.S.C. § 371 of International Patent Application No. PCT/US2018/022598, filed Mar. 15, 2018, which claims the benefit of priority under 35 U.S.C. § 119(e) of U.S. Ser. No. 62/471,741, filed Mar. 15, 2017, and of U.S. Ser. No. 62/507,713, filed May 17, 2017, the entire content of each of which is incorporated herein by reference.

GRANT INFORMATION

This invention was made with government support under Grant Nos. 2R01 DK090058. DK090058 and HL107755 awarded by the National Institutes of Health. The United States government has certain rights in the invention.

SEQUENCE LISTING

The instant application contains a Sequence Listing which has been submitted electronically in ASCII format and is hereby incorporated by reference in its entirety. Said ASCII copy, created on Mar. 15, 2018, is named 20378-201753_SL.txt and is 109 kilobytes in size.

BACKGROUND OF THE INVENTION

Field of the Invention

The invention relates generally to lysosomal diseases associated with dysfunctional transmembrane lysosomal proteins and more specifically to treatment of such diseases with hematopoietic stem and progenitor cell (HSPC) gene therapy.

Background Information

Lysosomal membrane proteins act at several crucial steps of the lysosome life cycle, including lumen acidification, metabolite export, molecular motor recruitment and fusion with other organelles. Lysosomal storage diseases are a group of inherited metabolic disorders that result from defects in lysosomal function. Lysosomes are sacs of enzymes within cells that digest large molecules and pass the fragments on to other parts of the cell for recycling. This process requires several critical enzymes. If one of these enzymes is defective (for example, because of a mutation), the large molecules accumulate within the cell, eventually killing it.

Among the ~50 known lysosomal storage diseases, several are caused by lysosomal membrane protein dysfunction. One such lysosomal membrane protein disease is cystinosis, which is characterized by the abnormal accumulation of the amino acid cystine in all cells of the body leading to multi-organ failure. Cystinosis is caused by mutations in the CTNS gene that codes for cystinosin, the lysosomal membrane-specific transporter for cystine. Intracellular metabolism of cystine, as it happens with all amino acids, requires its transport across the cell membrane. After degradation of endocytosed protein to cystine within lysosomes, it is normally transported to the cytosol. But if there is a defect in the carrier protein, cystine is accumulated in lysosomes. As cystine is highly insoluble, when its concentration in tissue lysosomes increase, its solubility is immediately exceeded and crystalline precipitates are formed in almost all organs and tissues. Another example is Danon disease, which is caused by mutations in the LAMP-2 gene, a lysosomal transmembrane protein critical for autophagic flux.

To date, there are no known cures or preventative measures for such lysosomal diseases, with current therapies being directed to treating the associated symptoms. Thus, there is a need in the art for alternative or improved methods for treating lysosomal diseases/disorders.

SUMMARY OF THE INVENTION

Accordingly, in one aspect, the invention provides a method of treating a lysosomal transmembrane protein disease or disorder in a subject. The method includes introducing a corresponding functional human lysosomal transmembrane protein into hematopoietic stem and progenitor cells (HSPCs) of the subject, and transplanting the HSPCs into the subject, thereby treating the lysosomal transmembrane protein disease or disorder. Thus, when the lysosomal transmembrane protein disease or disorder is cystinosis, the corresponding functional human lysosomal transmembrane protein is cystinosin (CTNS); the lysosomal transmembrane protein disease or disorder is Salla disease or infantile sialic acid storage disorder, the corresponding functional human lysosomal transmembrane protein is sialin (SLC17A5); the lysosomal transmembrane protein disease or disorder is Cobalamin F-type disease, the corresponding functional human lysosomal transmembrane protein is LMBD1; the lysosomal transmembrane protein disease or disorder is late infantile neuronal ceroid lipofuscinosis, the corresponding functional human lysosomal transmembrane protein is CLN7; the lysosomal transmembrane protein disease or disorder is juvenile neuronal ceroid lipofuscinosis, the corresponding functional human lysosomal transmembrane protein is Battenin (CLN3); the lysosomal transmembrane protein disease or disorder is malignant infantile osteopoetrosis, the corresponding functional human lysosomal transmembrane protein is C1C-7 or OSTM1; the lysosomal transmembrane protein disease or disorder is mucolipidosis IV, the corresponding functional human lysosomal transmembrane protein is TRPML-1; the lysosomal transmembrane protein disease or disorder is mucopolysaccharidosis type IIIC, the corresponding functional human lysosomal transmembrane protein is HGSNAT; the lysosomal transmembrane protein disease or disorder is Neiman-Pick Type C, the corresponding functional human lysosomal transmembrane protein is NPC-1; and the lysosomal transmembrane protein disease or disorder is Danon disease, the corresponding functional human lysosomal transmembrane protein is LAMP2.

In various embodiments, the step of introducing may include contacting a vector comprising a polynucleotide encoding functional human lysosomal transmembrane protein and a functional promoter with the HSPCs and allowing expression of the functional human lysosomal transmembrane protein. In various embodiments, the lysosomal transmembrane protein disease or disorder is cystinosis and the functional human lysosomal transmembrane protein is CTNS. In various embodiments, the lysosomal transmembrane protein disease or disorder is Danon disease and the functional human lysosomal transmembrane protein is LAMP2. The LAMP2 may be an isoform selected from the group consisting of LAMP-2A, LAMP-2B, LAMP-2C. The subject may be a mammal, such as a human. In various embodiments, the vector is a viral vector selected from the group consisting of a lentiviral, adenoviral, and AAV vector. In various embodiments, the vector is a lentiviral vector. In various embodiments, the vector is an adenoviral vector. In various embodiments, the vector is an AAV vector. In various embodiments, the vector is a self-inactivating (SIN)-lentivirus vector, such as pCCL-CTNS or pCCL-LAMP2. In various embodiments, the step of introducing is performed ex vivo. In various embodiments, the HSPCs are isolated from the bone marrow of the subject.

In another aspect, the present invention provides an expression cassette comprising a promoter functionally linked to a transgene encoding a functional human lysosomal transmembrane protein selected from the group consisting of CTNS, SLC17A5, LMBRD1, CLN7, CLN3, CLC-7, OSTM1, TRPML1, HGSNAT, NPC1, and LAMP2. Also provided are a vector, such as a self-inactivating (SIN)-lentivirus vector, that includes a promoter functionally linked to a polynucleotide encoding a functional human lysosomal transmembrane protein selected from the group consisting of CTNS, SLC17A5, LMBRD1, CLN7, CLN3, CLC-7, OSTM1, TRPML1, HGSNAT, NPC1, and LAMP2. In various embodiments, the functional human lysosomal transmembrane protein is CTNS. In various embodiments, the functional human lysosomal transmembrane protein is LAMP2.

In another aspect, the present invention provides a method of treating or ameliorating a lysosomal protein disease or disorder in a subject. The method includes isolating hematopoietic stem and HSPCs cells from a subject's bone marrow, introducing a functional human lysosomal transmembrane gene into the HSPCs, wherein the gene encodes a protein corresponding to the lysosomal protein disease or disorder, and transplanting the HSPCs back into the subject, thereby treating or ameliorating the lysosomal protein disease or disorder. Thus, when the lysosomal transmembrane protein disease or disorder is cystinosis, the functional human lysosomal transmembrane gene is CTNS; the lysosomal transmembrane protein disease or disorder is Salla disease or infantile sialic acid storage disorder, the functional human lysosomal transmembrane gene is SLC17A5; the lysosomal transmembrane protein disease or disorder is Cobalamin F-type disease, the functional human lysosomal transmembrane gene is LMBRD1; the lysosomal transmembrane protein disease or disorder is late infantile neuronal ceroid lipofuscinosis, the functional human lysosomal transmembrane gene is MFSD8; the lysosomal transmembrane protein disease or disorder is juvenile neuronal ceroid lipofuscinosis, the functional human lysosomal transmembrane gene is CLN3; the lysosomal transmembrane protein disease or disorder is malignant infantile osteopoetrosis, the functional human lysosomal transmembrane gene is CLCN7 or OSTM1; the lysosomal transmembrane protein disease or disorder is mucolipidosis IV, the functional human lysosomal transmembrane gene is MCOLN1; the lysosomal transmembrane protein disease or disorder is mucopolysaccharidosis type IICIIIC, the functional human lysosomal transmembrane gene is HGSNAT; the lysosomal transmembrane protein disease or disorder is Neiman-Pick Type C, the functional human lysosomal transmembrane gene is NPC1; and the lysosomal transmembrane protein disease or disorder is Danon disease, the functional human lysosomal transmembrane gene is LAMP2.

In various embodiments, the HSPCs are CD34+ cells. In various embodiments the lysosomal protein disease or disorder is cystinosis and the functional human lysosomal transmembrane gene is CTNS. In various embodiments, the lysosomal protein disease or disorder is Danon disease and the functional human lysosomal transmembrane gene is LAMP2. In various embodiments, the step of introducing the functional human CTNS gene into the HSPCs includes using a vector, such as a viral vector. In various embodiments, the vector is a viral vector selected from the group consisting of a lentiviral, adenoviral, and AAV vector. In various embodiments, the level of cystine in the eye, skin, leukocytes, parenchymal tissue or gastrointestinal tract of the subject is reduced following treatment. In various embodiments, the dosage is about $1.0\times10^6$ to $5.0\times10^6$ cells/kg, such as $2.5\times10^6$ cells/kg, administered as a single dose.

The subject may be on cysteamine therapy, such as oral cysteamine therapy, prior to treatment. The dose administration may be intravenous. In various embodiments, cystine or cystine crystals are measure in the eye, skin, leukocytes, parenchymal tissue and/or gastrointestinal tract prior to and/or following treatment. In various embodiments, cystine or cystine crystals are measured in the eye prior to and/or following treatment. In various embodiments, cystine crystals are measured using in vivo confocal microscopy. In various embodiments, cystine levels may be measured prior to, during and/or following treatment. In various embodiments, cystine levels are measured using biological samples, such as blood, rectal biopsies, or buccal mucosa. In various embodiments, cystine levels are measured from rectal biopsies.

In another aspect, the present invention provides a method of treating or ameliorating a lysosomal protein disease or disorder in a subject. The method includes producing a functional human lysosomal transmembrane gene in the subject using gene editing. Thus, when the lysosomal transmembrane protein disease or disorder is cystinosis, the functional human lysosomal transmembrane gene is CTNS; the lysosomal transmembrane protein disease or disorder is Salla disease or infantile sialic acid storage disorder, the functional human lysosomal transmembrane gene is SLC17A5; the lysosomal transmembrane protein disease or disorder is Cobalamin F-type disease, the functional human lysosomal transmembrane gene is LMBRD1; the lysosomal transmembrane protein disease or disorder is late infantile neuronal ceroid lipofuscinosis, the functional human lysosomal transmembrane gene is MFSD8; the lysosomal transmembrane protein disease or disorder is juvenile neuronal ceroid lipofuscinosis, the functional human lysosomal transmembrane gene is CLN3; the lysosomal transmembrane protein disease or disorder is malignant infantile osteopoetrosis, the functional human lysosomal transmembrane gene is CLCN7 or OSTM1; the lysosomal transmembrane protein disease or disorder is mucolipidosis IV, the functional human lysosomal transmembrane gene is MCOLN1; the lysosomal transmembrane protein disease or disorder is mucopolysaccharidosis type IICIIIC, the functional human lysosomal transmembrane gene is HGSNAT; the lysosomal transmembrane protein disease or disorder is Neiman-Pick Type C, the functional human lysosomal transmembrane gene is NPC1; and the lysosomal transmembrane protein disease or disorder is Danon disease, the functional human lysosomal transmembrane gene is LAMP2.

In another aspect, the present invention provides a method of treating or ameliorating a lysosomal protein disease or disorder in a subject. The method includes contacting cells expressing a defective lysosomal transmembrane protein from the subject with a vector encoding a gene editing system that, when transfected into the cells, removes a trinucleotide extension mutation of the gene encoding the endogenous lysosomal transmembrane protein, thereby treating the lysosomal protein disease or disorder. Thus, when the lysosomal transmembrane protein disease or disorder is cystinosis, the lysosomal transmembrane protein is cystinosin (CTNS); the lysosomal transmembrane protein disease or disorder is Salla disease or infantile sialic acid storage disorder, the lysosomal transmembrane protein is sialin (SLC17A5); the lysosomal transmembrane protein disease or disorder is Cobalamin F-type disease, the lysosomal transmembrane protein is LMBD1; the lysosomal transmembrane protein disease or disorder is late infantile neuronal ceroid lipofuscinosis, the lysosomal transmembrane protein is CLN7; the lysosomal transmembrane protein disease or disorder is juvenile neuronal ceroid lipofuscinosis, the lysosomal transmembrane protein is Battenin (CLN3); the lysosomal transmembrane protein disease or disorder is malignant infantile osteopoetrosis, the lysosomal transmembrane protein is C1C-7 or OSTM1; the lysosomal transmembrane protein disease or disorder is mucolipidosis IV, the lysosomal transmembrane protein is TRPML-1; the lysosomal transmembrane protein disease or disorder is mucopolysaccharidosis type IICIIIC, the lysosomal transmembrane protein is HGSNAT; the lysosomal transmembrane protein disease or disorder is Neiman-Pick Type C, the lysosomal transmembrane protein is NPC-1; and the lysosomal transmembrane protein disease or disorder is Danon disease, the lysosomal transmembrane protein is LAMP2.

In various embodiments, the gene editing system is selected from the group consisting of CRISPR/Cas, zinc finger nucleases, engineered meganucleases, ARCUS, and transcription activator-life effector nucleases. In various embodiments, the step of contacting comprises administering to the subject an effective amount of the vector. In various embodiments, the step of contacting comprises obtaining a sample of cells from the subject, transfecting the gene editing system into the sample of cells, and thereafter, transplanting the transfected cells into the subject. In various embodiments, the sample of cells is selected from the group consisting of blood cells and HSPCs.

BRIEF DESCRIPTION OF THE DRAWINGS

FIGS. 1A and 1B show the results from hematoxylin & eosin staining revealing severe anomalies in $Ctns^{-/-}$ mice (FIG. 1A) whereas HSC-transplanted $Ctns^{-/-}$ mice exhibited only focal anomalies (FIG. 1B). FIGS. 1C and 1D show the results of methylene blue staining revealed the presence of abundant cystine crystals in the kidney of the $Ctns^{-/-}$ mice (FIG. 1C) and very few in the treated $Ctns^{-/-}$ mice (FIG. 1D).

FIG. 2A shows lateral cornea IVCM representations of $Ctns^{-/-}$ controls and LOW and HIGH HSC-transplanted mice. FIG. 2B shows surface crystal quantification within each layer of the full IVCM cornea scans from both eyes of $Ctns^{-/-}$ controls and transplanted (LOW and HIGH) mice. Error bars represent SEM (* $p<0.05$, ** $p<0.005$).

FIGS. 5A and 5B show histograms representing percent decrease in cystine content in DsRed-$Ctns^{-/-}$ fibroblasts (recipient cells) when plated together with contact co-culture assays (FIG. 5A) or separated by 1-μm port transwell filters from transwell assays (FIG. 5B) either GFP-MSCs or GFP-macrophages (donor cells) (N=4 replicates for each). Values are means±standard deviations. *$p<0.05$; $p<0.01$; * $p<0.005$. FIG. 5C shows a confocal image of TNTs (arrowheads) extended from GFP-macrophages to DsRed-$Ctns^{-/-}$ fibroblasts. FIG. 5D shows representative frames from a confocal movie showing migration of cystinosin-GFP-contacting vesicles via TNTs from a CTNS-GFP-expressing macrophage towards $Ctns^{-/-}$ fibroblasts (arrowheads). Bars: (FIG. 5C) 30 μm; (FIG. 5D) 20 μm.

FIG. 6A shows confocal images of kidney from 8 month-old $Ctns^{-/-}$ mice at 6 months post-transplantation with GFPWT HSPCs. GFP is in green and laminin in red. PTCs (lumen, #) was labeled by Lotus Tetragonobus-lectin (LT) (blue). FIGS. 6A-a1, 6A-a2, and 6A a3 show that eGFP-expressing HSC-derived cells display numerous extensions. Arrowheads indicate TBL crossing. Apoptotic PTC (*). FIG. 6A-a3 shows GFP-expressing green structures are located within PTCs. FIGS. 6B-6D show Z-stack confocal images of kidneys obtained from $Ctns^{-/-}$ mice transplanted with DsRed-$Ctns^{-/-}$ HSPCs (control, FIG. 6B) or DsRed-$Ctns^{-/-}$ HSPCs lentivirally transduced to express cystinosin-GFP and stained for phalloidin (FIG. 6C). Cystinosin-GFP-containing vesicles are abundant in the cytoplasm of PTCs (FIG. 6C). FIGS. 6B and 6C show nuclei that are stained in blue (DAPI). Scale bars: 5 μm (FIG. 6A), 10 μm (FIGS. 6B and 6C).

FIG. 8A shows cystine content in non-treated $Ctns^{-/-}$ mice (KO) compared with treated with pCCL-CTNS-HSCs. FIG. 8B shows quantification of cystine crystals on kidney sections stained with methylene blue. Abundant cystine crystals were observed in kidney sections from nontreated $Ctns^{-/-}$ mice (FIG. 8C) in contrast to pCCLCTNS-treated mice (FIG. 8D). Error bars are defined as Mean+SD, *$P<0.05$.

FIGS. 9A-9B are graphical diagrams showing the results from in vivo toxicology studies. FIGS. 9A-1 and 9A-2 show body weight of $Ctns^{-/-}$ males (FIGS. 9A-1) and females treated (FIG. 9A-2) with pCCL-CTNS-transduced HSCs and mock treated. FIG. 9B shows cystine content in tissues of $Ctns^{-/-}$ mice treated with pCCL-CTNS-transduced HSCs and mock treated.

FIGS. 10A-10E are pictorial diagrams showing LAMP2 expression in heart and skeletal muscle of WT-HSPC-transplant recipients. FIGS. 10A-10C are images showing LAMP2 expression in the hearts of WT (FIG. 10A), KO (FIG. 10B), and WT-HSPC transplanted showing LAMP2 expressing vesicles in cardiomyocytes adjacent to WT- GFP+ macrophages (FIG. 10C). Arrows demonstrate RFP+ vacuoles. Western blots of heart (FIG. 10D) and skeletal muscle (FIG. 10E) lysates show near WT-level restoration of LAMP2 expression in mice recipient of WT-HSPC transplant.

FIG. 12A shows representative EM images of the hearts of WT, KO, WT-HSPC transplanted, and KO-HSPC transplanted mice. FIG. 12B shows quantification of EM images demonstrating rescue of the accumulation of AVs in WT-HSPC mice to near WT levels. FIGS. 12C and 12D show Western blots and results demonstrating decreased LC-II/GAPDH levels in WT-HSPC transplanted mice vs. KO mice. *p<0.05 vs. WT; #p<0.05 vs. KO.

DETAILED DESCRIPTION OF THE INVENTION

Figure 1A:
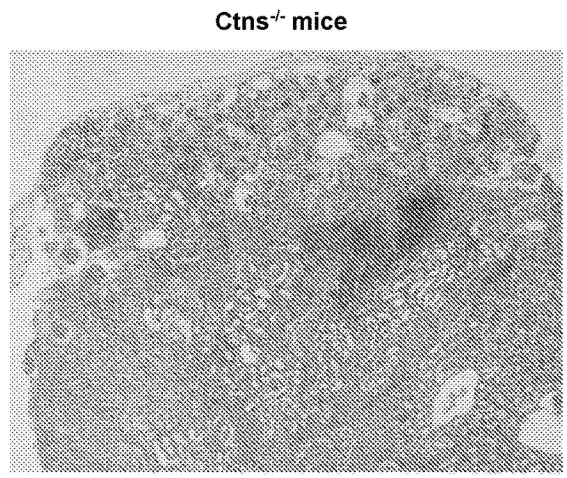
FIGS. 1A-1D are pictorial diagrams showing histological analyses of kidney sections of 15 months old $Ctns^{-/-}$ mice.
Figure 1B:
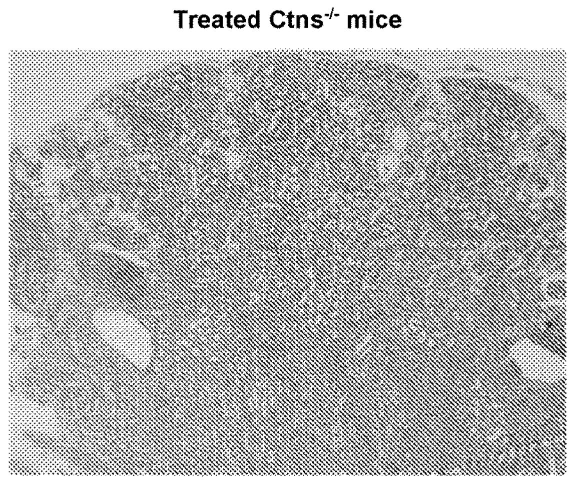
Figure 1C:
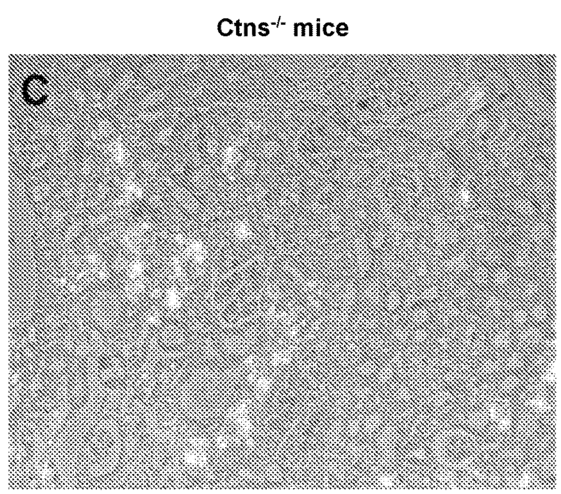
Figure 1D:
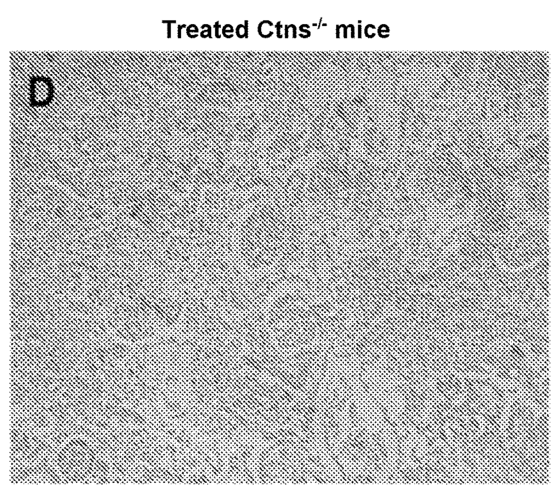
Figure 2A:
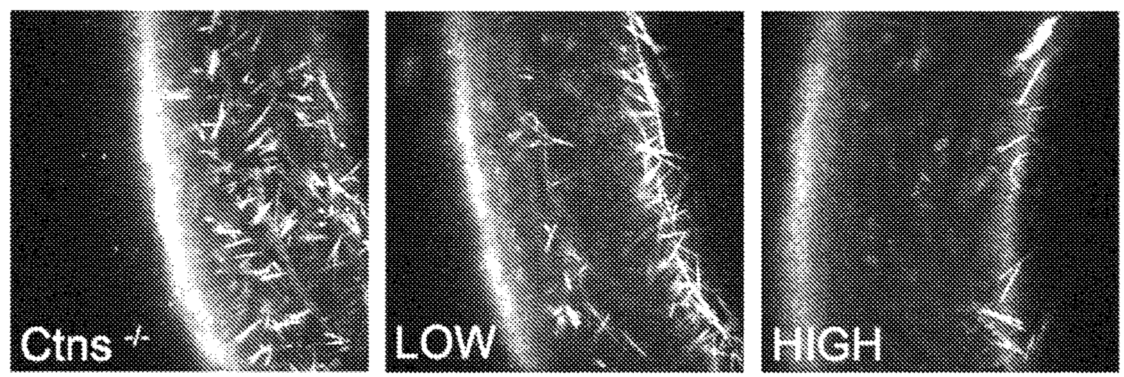
FIGS. 2A and 2B are pictorial and graphical diagrams showing cystine crystals in the cornea.
Figure 2B:
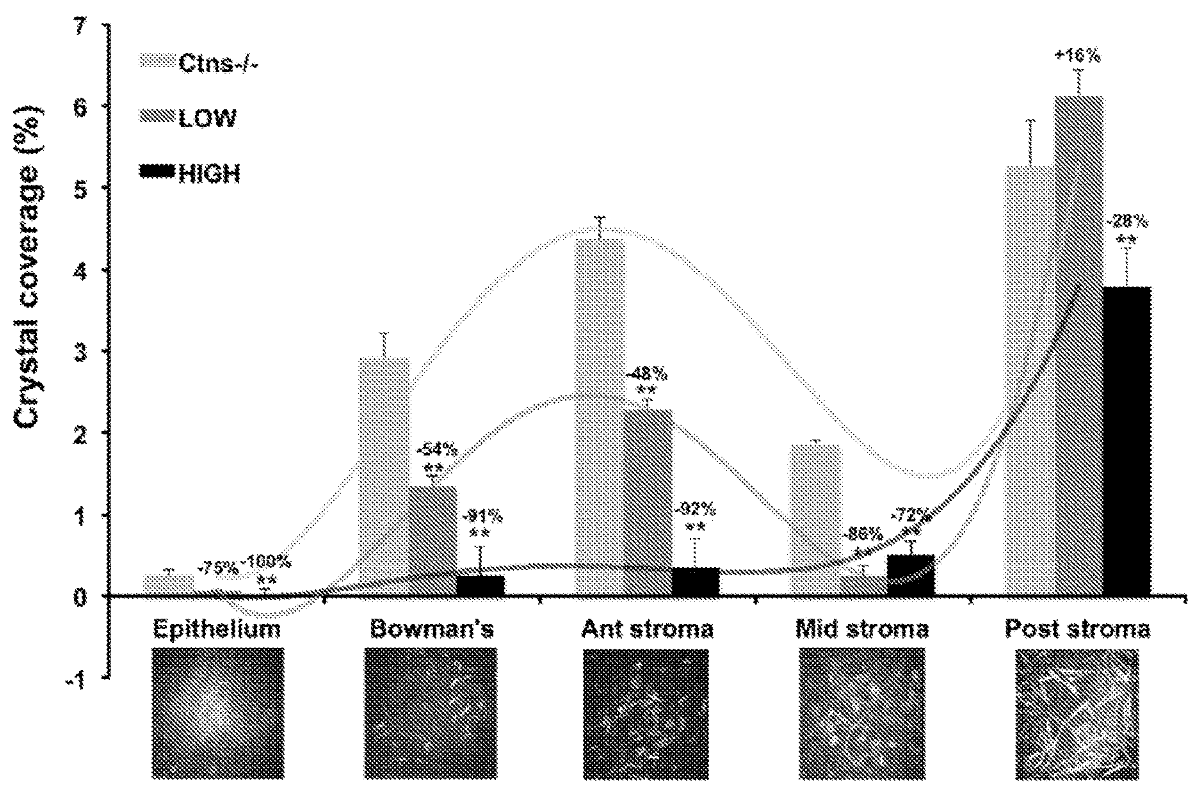

The present invention is based, in part, on the finding that a self-inactivating (SIN)-lentivirus vector containing the encoding human cystinosin (CTNS) or LAMP-2 cDNA and a functional promoter can be used to ex vivo gene-corrected patients' autologous hematopoietic stem and progenitor cells (HSPCs), which can then be re-transplanted in the patients to repopulate their bone marrow, which is a reservoir of "healthy" cells for the rest of the life of the patients. These cells mobilize and integrate into the disease tissues, brain, muscle, heart, leading to their rescue. While autologous HSPCs are used in the illustrative examples herein, one of skill in the art would recognize that other HSPCs would be useful as well (e.g., allogeneic).

Before the present compositions and methods are described, it is to be understood that this invention is not limited to particular compositions, methods, and experimental conditions described, as such compositions, methods, and conditions may vary. It is also to be understood that the terminology used herein is for purposes of describing particular embodiments only, and is not intended to be limiting, since the scope of the present invention will be limited only in the appended claims.

As used in this specification and the appended claims, the singular forms "a", "an", and "the" include plural references unless the context clearly dictates otherwise. Thus, for example, references to "the method" includes one or more methods, and/or steps of the type described herein which will become apparent to those persons skilled in the art upon reading this disclosure and so forth.

The term "comprising," which is used interchangeably with "including," "containing," or "characterized by," is inclusive or open-ended language and does not exclude additional, unrecited elements or method steps. The phrase "consisting of" excludes any element, step, or ingredient not specified in the claim. The phrase "consisting essentially of" limits the scope of a claim to the specified materials or steps and those that do not materially affect the basic and novel characteristics of the claimed invention. The present disclosure contemplates embodiments of the invention compositions and methods corresponding to the scope of each of these phrases. Thus, a composition or method comprising recited elements or steps contemplates particular embodiments in which the composition or method consists essentially of or consists of those elements or steps.

Unless defined otherwise, all technical and scientific terms used herein have the same meaning as commonly understood by one of ordinary skill in the art to which this invention belongs. Although any methods and materials similar or equivalent to those described herein can be used in the practice or testing of the invention, the preferred methods and materials are now described.

The term "subject" or "host organism," as used herein, refers to any individual or patient to which the subject methods are performed. Generally the subject is human, although as will be appreciated by those in the art, the subject may be an animal. Thus other animals, including mammals such as rodents (including mice, rats, hamsters and guinea pigs), cats, dogs, rabbits, farm animals including cows, horses, goats, sheep, pigs, etc., and primates (including monkeys, chimpanzees, orangutans and gorillas) are included within the definition of subject.

The term "biological sample," refers to any sample taken from a participant, including but not limited to cells, blood, tissue, skin, urine, etc., or hair.

The term "buccal mucosa," refers to the inside lining of the cheeks and floor of the mouth.

The term "therapeutically effective amount" or "effective amount" means the amount of a compound or pharmaceutical composition that elicits the biological or medical response of a tissue, system, animal or human that is being sought by the researcher, veterinarian, medical doctor or other clinician. Thus, the term "therapeutically effective amount" is used herein to denote any amount of a formulation that causes a substantial improvement in a disease condition when applied to the affected areas repeatedly over a period of time. The amount varies with the condition being treated, the stage of advancement of the condition, and the type and concentration of formulation applied. Appropriate amounts in any given instance will be readily apparent to those skilled in the art or capable of determination by routine experimentation. In the context of cystinosin, an example of a therapeutically effective amount of an agent, such as a population of hematopoietic stem cells transduced, gene-edited, or otherwise modified to express a human cystinosin transgene, is an amount sufficient to reduce the quantity of cystine (e.g., crystalline cystine) in the lysosomes of a cell in the patient, such as a cell in the kidney, liver, lung, spleen, muscle, brain, and/or heart.

A "dosage" or "dose" are defined to include a specified size, frequency, or exposure level are included within the definition.

A "therapeutic effect," as used herein, encompasses a therapeutic benefit and/or a prophylactic benefit as described herein.

The terms "administration" or "administering" are defined to include an act of providing a compound or pharmaceutical composition of the invention to a subject in need of treatment. The phrases "parenteral administration" and "administered parenterally" as used herein means modes of administration other than enteral and topical administration, usually orally or by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and infrasternal injection and infusion. The phrases "systemic administration," "administered systemically," "peripheral administration" and "administered peripherally" as used herein mean the administration of a compound, drug or other material other than directly into the central nervous system, such that it enters the subject's system and, thus, is subject to metabolism and other like processes, for example, subcutaneous administration.

If a viral vector specific for the cell type is not available, the vector can be modified to express a receptor (or ligand) specific for a ligand (or receptor) expressed on the target cell, or can be encapsulated within a liposome, which also can be modified to include such a ligand (or receptor). A peptide agent can be introduced into a cell by various methods, including, for example, by engineering the peptide to contain a protein transduction domain such as the human immunodeficiency virus TAT protein transduction domain, which can facilitate translocation of the peptide into the cell. In addition, there are a variety of biomaterial-based technologies such as nano-cages and pharmacological delivery wafers (such as used in brain cancer chemotherapeutics) which may also be modified to accommodate this technology.

The viral vectors most commonly assessed for gene transfer are based on DNA-based adenoviruses (Ads) and adeno-associated viruses (AAVs) and RNA-based retroviruses and lentiviruses. Lentivirus vectors have been most commonly used to achieve chromosomal integration.

The term "parenchymal," refers to the functional parts of an organ, which sometimes includes structural parts of the same and/or adjacent organ.

As used herein, the terms "reduce" and "inhibit" are used together because it is recognized that, in some cases, a decrease can be reduced below the level of detection of a particular assay. As such, it may not always be clear whether the expression level or activity is "reduced" below a level of detection of an assay, or is completely "inhibited." Nevertheless, it will be clearly determinable, following a treatment according to the present methods.

As used herein, "treatment" or "treating" means to administer a composition to a subject or a system with an undesired condition. The condition can include a disease or disorder. "Prevention" or "preventing" means to administer a composition to a subject or a system at risk for the condition. The condition can include a predisposition to a disease or disorder. The effect of the administration of the composition to the subject (either treating and/or preventing) can be, but is not limited to, the cessation of one or more symptoms of the condition, a reduction or prevention of one or more symptoms of the condition, a reduction in the severity of the condition, the complete ablation of the condition, a stabilization or delay of the development or progression of a particular event or characteristic, or minimization of the chances that a particular event or characteristic will occur.

As used herein, the term "genetic modification" is used to refer to any manipulation of an organism's genetic material in a way that does not occur under natural conditions. Methods of performing such manipulations are known to those of ordinary skill in the art and include, but are not limited to, techniques that make use of vectors for transforming cells with a nucleic acid sequence of interest. Included in the definition are various forms of gene editing in which DNA is inserted, deleted or replaced in the genome of a living organism using engineered nucleases, or "molecular scissors." These nucleases create site-specific double-strand breaks (DSBs) at desired locations in the genome. The induced double-strand breaks are repaired through nonhomologous end-joining (NHEJ) or homologous recombination (HR), resulting in targeted mutations (i.e., edits).

There are several families of engineered nucleases used in gene editing, for example, but not limited to, meganucleases, zinc finger nucleases (ZFNs), transcription activator-like effector-based nucleases (TALEN), the CRISPR-Cas system, and ARCUS. However, it should be understood that any known gene editing system utilizing engineered nucleases may be used in the methods described herein.

CRISPR (Clustered Regularly Interspaced Short Palindromic Repeats) is an acronym for DNA loci that contain multiple, short, direct repetitions of base sequences. The prokaryotic CRISPR/Cas system has been adapted for use as gene editing (silencing, enhancing or changing specific genes) for use in eukaryotes (see, for example, Cong, Science, 15:339(6121):819-823 (2013) and Jinek, et al., Science, 337(6096):816-21 (2012)). By transfecting a cell with elements including a Cas gene and specifically designed CRISPRs, nucleic acid sequences can be cut and modified at any desired location. Methods of preparing compositions for use in genome editing using the CRISPR/Cas systems are described in detail in US Pub. No. 2016/0340661, US Pub. No. 20160340662, US Pub. No. 2016/0354487, US Pub. No. 2016/0355796, US Pub. No. 20160355797, and WO 2014/018423, which are specifically incorporated by reference herein in their entireties.

Thus, as used herein, "CRISPR system" refers collectively to transcripts and other elements involved in the expression of or directing the activity of CRISPR-associated ("Cas") genes, including sequences encoding a Cas gene, a tracr (trans-activating CRISPR) sequence (e.g., tracrRNA or an active partial tracrRNA), a tracr-mate sequence (encompassing a "direct repeat" and a tracrRNA-processed partial direct repeat in the context of an endogenous CRISPR system), a guide sequence (also referred to as a "spacer", "guide RNA" or "gRNA" in the context of an endogenous CRISPR system), or other sequences and transcripts from a CRISPR locus. One or more tracr mate sequences operably linked to a guide sequence (e.g., direct repeat-spacer-direct repeat) can also be referred to as "pre-crRNA" (pre-CRISPR RNA) before processing or crRNA after processing by a nuclease.

In some embodiments, a tracrRNA and crRNA are linked and form a chimeric crRNA-tracrRNA hybrid where a mature crRNA is fused to a partial tracrRNA via a synthetic stem loop to mimic the natural crRNA:tracrRNA duplex as described in Cong, Science, 15:339(6121):819-823 (2013) and Jinek, et al., Science, 337(6096):816-21 (2012)). A single fused crRNA-tracrRNA construct can also be referred to as a guide RNA or gRNA (or single-guide RNA (sgRNA)). Within an sgRNA, the crRNA portion can be identified as the 'target sequence' and the tracrRNA is often referred to as the 'scaffold'.

There are many resources available for helping practitioners determine suitable target sites once a desired DNA target sequence is identified. For example, numerous public resources, including a bioinformatically generated list of about 190,000 potential sgRNAs, targeting more than 40% of human exons, are available to aid practitioners in selecting target sites and designing the associate sgRNA to affect a nick or double strand break at the site. See also, crispr.u-psud.fr, a tool designed to help scientists find CRISPR targeting sites in a wide range of species and generate the appropriate crRNA sequences.

In some embodiments, one or more vectors driving expression of one or more elements of a CRISPR system are introduced into a target cell such that expression of the elements of the CRISPR system direct formation of a CRISPR complex at one or more target sites. While the specifics can be varied in different engineered CRISPR systems, the overall methodology is similar. A practitioner interested in using CRISPR technology to target a DNA sequence can insert a short DNA fragment containing the target sequence into a guide RNA expression plasmid. The sgRNA expression plasmid contains the target sequence (about 20 nucleotides), a form of the tracrRNA sequence (the scaffold) as well as a suitable promoter and necessary elements for proper processing in eukaryotic cells. Such vectors are commercially available (see, for example, Addgene). Many of the systems rely on custom, complementary oligos that are annealed to form a double stranded DNA and then cloned into the sgRNA expression plasmid. Co-expression of the sgRNA and the appropriate Cas enzyme from the same or separate plasmids in transfected cells results in a single or double strand break (depending of the activity of the Cas enzyme) at the desired target site.

Zinc-finger nucleases (ZFNs) are artificial restriction enzymes generated by fusing a zinc finger DNA-binding domain to a DNA-cleavage domain. Zinc finger domains can be engineered to target specific desired DNA sequences and this enables zinc-finger nucleases to target unique sequences within complex genomes. By taking advantage of endogenous DNA repair machinery, these reagents can be used to precisely alter the genomes of higher organisms. The most common cleavage domain is the Type IIS enzyme Fok1. Fok1 catalyzes double-stranded cleavage of DNA, at 9 nucleotides from its recognition site on one strand and 13 nucleotides from its recognition site on the other. See, for example, U.S. Pat. Nos. 5,356,802; 5,436,150 and 5,487,994; as well as Li et al. *Proc., Natl. Acad. Sci. USA* 89 (1992):4275-4279; Li et al. *Proc. Natl. Acad. Sci. USA,* 90:2764-2768 (1993); Kim et al. *Proc. Natl. Acad. Sci. USA.* 91:883-887 (1994a); Kim et al. *J. Biol. Chem.* 269:31,978-31,982 (1994b), all of which are incorporated herein by reference. One or more of these enzymes (or enzymatically functional fragments thereof) can be used as a source of cleavage domains.

Transcription activator-like effector nucleases (TALENs) have an overall architecture similar to that of ZFNs, with the main difference being that the DNA-binding domain comes from TAL effector proteins, transcription factors from plant pathogenic bacteria. The DNA-binding domain of a TALEN is a tandem array of amino acid repeats, each about 34 residues long. The repeats are very similar to each other; typically they differ principally at two positions (amino acids 12 and 13, called the repeat variable diresidue, or RVD). Each RVD specifies preferential binding to one of the four possible nucleotides, meaning that each TALEN repeat binds to a single base pair, though the NN RVD is known to bind adenines in addition to guanine. TAL effector DNA binding is mechanistically less well understood than that of zinc-finger proteins, but their seemingly simpler code could prove very beneficial for engineered-nuclease design. TALENs also cleave as dimers, have relatively long target sequences (the shortest reported so far binds 13 nucleotides per monomer) and appear to have less stringent requirements than ZFNs for the length of the spacer between binding sites. Monomeric and dimeric TALENs can include more than 10, more than 14, more than 20, or more than 24 repeats. Methods of engineering TAL to bind to specific nucleic acids are described in Cermak, et al, *Nucl. Acids Res.* 1-11 (2011); US Published Application No. 2011/0145940, which discloses TAL effectors and methods of using them to modify DNA; Miller et al. *Nature Biotechnol* 29: 143 (2011) reported making TALENs for site-specific nuclease architecture by linking TAL truncation variants to the catalytic domain of Fok1 nuclease. The resulting TALENs were shown to induce gene modification in immortalized human cells. General design principles for TALE binding domains can be found in, for example, WO 2011/072246. Each of the foregoing references are incorporated herein by reference in their entireties.

The nuclease activity of the genome editing systems described herein cleave target DNA to produce single or double strand breaks in the target DNA. Double strand breaks can be repaired by the cell in one of two ways: non-homologous end joining, and homology-directed repair. In non-homologous end joining (NHEJ), the double-strand breaks are repaired by direct ligation of the break ends to one another. As such, no new nucleic acid material is inserted into the site, although some nucleic acid material may be lost, resulting in a deletion. In homology-directed repair, a donor polynucleotide with homology to the cleaved target DNA sequence is used as a template for repair of the cleaved target DNA sequence, resulting in the transfer of genetic information from a donor polynucleotide to the target DNA. As such, new nucleic acid material can be inserted/copied into the site. Therefore, in some embodiments, the genome editing vector or composition optionally includes a donor polynucleotide. The modifications of the target DNA due to NHEJ and/or homology-directed repair can be used to induce gene correction, gene replacement, gene tagging, transgene insertion, nucleotide deletion, gene disruption, gene mutation, etc.

Accordingly, cleavage of DNA by the genome editing vector or composition can be used to delete nucleic acid material from a target DNA sequence by cleaving the target DNA sequence and allowing the cell to repair the sequence in the absence of an exogenously provided donor polynucleotide. Alternatively, if the genome editing composition includes a donor polynucleotide sequence that includes at least a segment with homology to the target DNA sequence, the methods can be used to add, i.e., insert or replace, nucleic acid material to a target DNA sequence (e.g., to "knock in" a nucleic acid that encodes for a protein, an siRNA, an miRNA, etc.), to add a tag (e.g., 6×His (SEQ ID NO: 27), a fluorescent protein (e.g., a green fluorescent protein; a yellow fluorescent protein, etc.), hemagglutinin (HA), FLAG, etc.), to add a regulatory sequence to a gene (e.g., promoter, polyadenylation signal, internal ribosome entry sequence (IRES), 2A peptide, start codon, stop codon, splice signal, localization signal, etc.), to modify a nucleic acid sequence (e.g., introduce a mutation), and the like. As such, the compositions can be used to modify DNA in a site-specific, i.e., "targeted" way, for example gene knock-out, gene knock-in, gene editing, gene tagging, etc., as used in, for example, gene therapy.

ARCUS is a genome editing platform derived from a natural genome editing enzyme referred to as a "homing endonuclease." Homing endonucleases are site-specific DNA-cutting enzymes encoded in the genomes of many eukaryotic species that are able to precisely recognize long DNA sequences (12-40 base pairs). These non-destructive enzymes trigger gene conversion events that modify the genome in a very precise way, most frequently by the insertion of a new DNA sequence. Thus, the ARCUS genome editing platform relies upon engineered ARC nucleases, which are fully synthetic enzymes similar to a homing endonuclease, but with improved specificity to recognize a DNA sequence within any target gene.

The terms "polypeptide," "peptide," and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, α-carboxyglutamate, and O-phosphoserine. Amino acid analogs refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

As used herein, a "regulatory gene" or "regulatory sequence" is a nucleic acid sequence that encodes products (e.g., transcription factors) that control the expression of other genes.

As used herein, a "protein coding sequence" or a sequence that encodes a particular protein or polypeptide, is a nucleic acid sequence that is transcribed into mRNA (in the case of DNA) and is translated (in the case of mRNA) into a polypeptide in vitro or in vivo when placed under the control of appropriate regulatory sequences. The boundaries of the coding sequence are determined by a start codon at the 5' terminus (N-terminus) and a translation stop nonsense codon at the 3' terminus (C-terminus). A coding sequence can include, but is not limited to, cDNA from eukaryotic mRNA, genomic DNA sequences from eukaryotic DNA, and synthetic nucleic acids. A transcription termination sequence will usually be located 3' to the coding sequence.

As used herein, a "promoter" is defined as a regulatory DNA sequence generally located upstream of a gene that mediates the initiation of transcription by directing RNA polymerase to bind to DNA and initiating RNA synthesis. A promoter can be a constitutively active promoter (i.e., a promoter that is constitutively in an active/"ON" state), it may be an inducible promoter (i.e., a promoter whose state, active/"ON" or inactive/"OFF", is controlled by an external stimulus, e.g., the presence of a particular compound or protein), it may be a spatially restricted promoter (i.e., transcriptional control element, enhancer, etc.) (e.g., tissue specific promoter, cell type specific promoter, etc.), and it may be a temporally restricted promoter (i.e., the promoter is in the "ON" state or "OFF" state during specific stages of embryonic development or during specific stages of a biological process. Thus, in various embodiments, the promoter may be a stem cell-specific promoter that drives transgene expression. For example, constitutive promoters of different strengths can be used. Expression vectors and plasmids in accordance with the present invention may include one or more constitutive promoters, such as viral promoters or promoters from mammalian genes that are generally active in promoting transcription. Exemplary promoters include, but are not limited to, human Elongation Factor 1 alpha promoter (EFS), SV40 early promoter, mouse mammary tumor virus long terminal repeat (LTR) promoter; adenovirus major late promoter (Ad MLP); a herpes simplex virus (HSV) promoter, an endogenous cellular promoter that is heterologous to the gene of interest, a cytomegalovirus (CMV) promoter such as the CMV immediate early promoter region (CMVIE), a Rous sarcoma virus (RSV) promoter, synthetic promoters, hybrid promoters, and the like As used herein, the term "gene" means the deoxyribonucleotide sequences comprising the coding region of a structural gene. A "gene" may also include non-translated sequences located adjacent to the coding region on both the 5' and 3' ends such that the gene corresponds to the length of the full-length mRNA. The sequences which are located 5' of the coding region and which are present on the mRNA are referred to as 5' non-translated sequences. The sequences which are located 3' or downstream of the coding region and which are present on the mRNA are referred to as 3' non-translated sequences. The term "gene" encompasses both cDNA and genomic forms of a gene. A genomic form or clone of a gene contains the coding region interrupted with non-coding sequences termed "introns" or "intervening regions" or "intervening sequences." Introns are segments of a gene which are transcribed into heterogenous nuclear RNA (hnRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide.

As used herein, the terms "functionally linked" and "operably linked" are used interchangeably and refer to a functional relationship between two or more DNA segments, in particular gene sequences to be expressed and those sequences controlling their expression. For example, a promoter/enhancer sequence, including any combination of cis-acting transcriptional control elements is operably linked to a coding sequence if it stimulates or modulates the transcription of the coding sequence in an appropriate host cell or other expression system. Promoter regulatory sequences that are operably linked to the transcribed gene sequence are physically contiguous to the transcribed sequence.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The term "antibody" as used herein refers to polyclonal and monoclonal antibodies and fragments thereof, and immunologic binding equivalents thereof. The term "antibody" refers to a homogeneous molecular entity, or a mixture such as a polyclonal serum product made up of a plurality of different molecular entities, and broadly encompasses naturally-occurring forms of antibodies (for example, IgG, IgA, IgM, IgE) and recombinant antibodies such as single-chain antibodies, chimeric and humanized antibodies and multi-specific antibodies. The term "antibody" also refers to fragments and derivatives of all of the foregoing, and may further comprise any modified or derivatized variants thereof that retains the ability to specifically bind an epitope. Antibody derivatives may comprise a protein or chemical moiety conjugated to an antibody. A monoclonal antibody is capable of selectively binding to a target antigen or epitope. Antibodies may include, but are not limited to polyclonal antibodies, monoclonal antibodies (mAbs), humanized or chimeric antibodies, camelized antibodies, single chain antibodies (scFvs), Fab fragments, $F(ab')_2$ fragments, disulfide-linked Fvs (sdFv) fragments, for example, as produced by a Fab expression library, anti-idiotypic (anti-Id) antibodies, intrabodies, nanobodies, synthetic antibodies, and epitope-binding fragments of any of the above.

As used herein, the term "humanized mouse" (Hu-mouse) is a mouse developed to carry functioning human genes, cells, tissues, and/or organs. Humanized mice are commonly used as small animal models in biological and medical research for human therapeutics. Immunodeficient mice are often used as recipients for human cells or tissues, because they can relatively easily accept heterologous cells due to lack of host immunity.

HSCs possess the ability of multipotency (i.e., one HSC can differentiate into all functional blood cells) and self-renewal (i.e., HSCs can divide and give rise to an identical daughter cell, without differentiation). Through a series of lineage commitment steps, HSCs give rise to progeny that progressively lose self-renewal potential and successively become more and more restricted in their differentiation capacity, generating multi-potential and lineage-committed progenitor cells, and ultimately mature functional circulating blood cells.

The ability of hematopoietic stem and progenitor cells (HSPCs) to self-renew and differentiate is fundamental for the formation and maintenance of life-long hematopoiesis and deregulation of these processes may lead to severe clinical consequences. HSPCs are also highly valuable for their ability to reconstitute the hematopoietic system when transplanted and this has enabled their use in the clinic to treat a variety of disorders including bone marrow failure, myeloproliferative disorders and other acquired or genetic disorders that affect blood cells.

As used herein, a "pluripotent cell" refers to a cell derived from an embryo produced by activation of a cell containing DNA of all female or male origin that can be maintained in vitro for prolonged, theoretically indefinite period of time in an undifferentiated state that can give rise to different differentiated tissue types, i.e., ectoderm, mesoderm, and endoderm. "Embryonic stem cells" (ES cells) are pluripotent stem cells derived from the inner cell mass of a blastocyst, an early-stage preimplantation embryo.

As used herein, an "autologous transplant" refers to a transplant that uses a subject's own stem cells. These cells are collected in advance and returned at a later stage. Thus, an "allogeneic transplant" refers to a transplant where the donor and the recipient of the stem cells are different people. Exemplary allogeneic cells include, but are not limited to, syngeneic cells, MHC-matched cells, etc.

As used herein "pharmaceutically acceptable carrier" encompasses any of the standard pharmaceutical carriers, such as a phosphate buffered saline solution, water and emulsions such as an oil/water or water/oil emulsion, and various types of wetting agents.

As used herein, a "lysosomal protein disorder" or "lysosomal protein disease" refers to any metabolic disorders that result from defects in lysosomal function. Also referred to as "lysosomal storage disorders", such diseases/disorders are typically caused by lysosomal dysfunction usually as a consequence of deficiency of a single enzyme required for the metabolism of lipids, glycoproteins (sugar containing proteins) or so-called mucopolysaccharides. Exemplary lysosomal storage disorders include, but are not limited to, cystinosis, Salla disease, infantile sialic acid storage disorder, Cobalamin F-type disease, neuronal ceroid lipofuscinosis (both late infantile and juvenile forms), malignant infantile osteopetrosis, mucolipidosis IV, mucopolysaccharidosis type IIIC (Sanfilippo syndrome C), Niemann-Pick Type C, and Danon disease (Ruivo, et al. *Biochimica et Biophysica Acta* 1793 (2009) 636-649, incorporated herein by reference).

For example, Cystinosis is an autosomal metabolic disease that belongs to the family of the lysosomal storage disorders. Cystinosis has a devastating impact on the affected individuals, primarily children and young adults, even with cysteamine treatment. The prevalence of cystinosis is 1:100,000 to 1:200,000. The gene involved in cystinosis is the gene CTNS that encodes for the 7-transmembrane lysosomal cystine transporter, cystinosin. The most severe and the most frequent form of cystinosis is the infantile form, also called nephropathic cystinosis. Children develop a renal Fanconi syndrome at 6-8 months of age, characterized by severe fluid and electrolyte disturbance, growth retardation and rickets. Progressive loss of glomerular function leads to renal failure; according to NAPRTCS' (North American Pediatric Renal Trials and Collaborative Studies), 1.4% of children on dialysis (2011 Annual Dialysis Report) and 2.1% with kidney transplants (2010 Annual Transplant Report) have cystinosis. Cystinosis as a clinical entity is also a progressive dysfunction of multiple organs caused by the accumulation of cystine in the lysosomes of all the cells in the body; affected patients store 50-100 times the normal amounts of cystine in their cells.

Cystine storage leads to the formation of cystine crystals in all tissues. The main clinical complications in cystinosis include to diabetes, hypothyroidism, myopathy and central nervous system deterioration. Corneal cystine crystals appear from the first decade of life resulting in photophobia and visual impairment. Swallowing difficulties, directly correlated with muscle atrophy, is a major cause of death in cystinosis. In addition to cystine builds up, cellular dysfunctions such as abnormal vesicular trafficking, autophagy and TFEB (Transcription Factor EB) signaling have also been described as responsible for the pathogenesis of cystinosis.

The current treatment for cystinosis is the drug cysteamine (mercaptoethylamine), which reduces the intracellular cystine content. However, this therapy only delays disease progression and has no effect on renal Fanconi syndrome nor does it prevent end stage renal failure in affected patients. Cysteamine has also been shown to be inefficient to improve cellular dysfunctions in CTNS-deficient cells, proving that cellular defects in cystinosis are not only due to cystine accumulation but also due to the lack of the cystinosin itself that interacts directly with key cellular components.

In addition, cysteamine has to be taken every 6 hours including at night, and results in bad body odor as well as severe gastrointestinal side effects such as vomiting and diarrhea that render treatment compliance difficult. In 2013, a delayed-release formulation of cysteamine (PROCYSBI®) was FDA-approved, which requires dosing every 12 hours. While PROCYSBI® reduces the number of doses improving the patients' quality of life, the impact on the disease is similar than immediate release cysteamine and patients still experience gastric side effects. Moreover, the cost of this medication is very high, $300,000-$600,000 per year per patient.

The ocular pathology in cystinosis requires topical administration of cysteamine eye drops every hour, which causes irritation and burning so compliance is very challenging. The cost of eye drops is about $50,000 per year per patient. Cysteamine and the supportive treatment for all the complications associated with cystinosis requires patients to take up to 60 pills per day; the kids often require placement of a gastric tube to be able to tolerate the medications and get essential caloric intake. Medical complications increase in severity and number with age resulting in new and ever-increasing symptoms and treatments. There are unending doctor appointments, G-tube feedings, frequent blood draws, growth hormones shots, bone pain, daily vomiting, eye pain and severe gastrointestinal side effects. As the disease progress, their bodies deteriorate. The most severe complications for adults are myopathy, pulmonary issues and progression of corneal cystinosis. Patients with renal failure require dialysis or transplantation, both of which have significant negative health effects and due to the severe shortage of donor organs, patients may wait three to six years for transplantation. Thus, the current standard of care does not prevent the progression of the disease and significantly impacts the quality of life for patients with cystinosis who still die in early adulthood.

Danon disease has many similarities to other lysosomal membrane protein diseases and is characterized as a disorder of autophagy that affects the degradation of many cellular components and thus does not result in the accumulation of a single substrate. Danon disease has been more recently described as an autophagic vacuolar myopathy. Danon disease is caused by mutations in the gene encoding lysosomal associated membrane protein 2 (LAMP-2), resulting in decreased expression of the LAMP-2 protein. Loss of LAMP-2 expression disrupts autophagic flux, impairing the ability of cells to respond to stress and remove damaged cellular components.

Thus, the present disclosure demonstrates that one-time hematopoietic stem and progenitor cell (HSPC) transplantation holds the potential to become a life-long curative therapy for a disease or disorder associated with a defective lysosomal transmembrane protein. The therapy may further prevent kidney transplantation and long-term complications associated with cystinosis including unexpectedly the clearance of the corneal cystine crystals. This should also allow patients to withdraw from oral cysteamine, cysteamine eye drops and any other medications used for treating symptoms associated with the disease. As such, the quality of life of the patients is greatly improved and the cost of treatment highly decreased.

Due to the multi-systemic nature of cystinosis and all the drugs necessary to compensate for the absence of the protein, cystinosin, in every tissues, a gene therapy approach was investigated. Gene therapy has the potential to become an important new approach for the third millennium to treat both rare and common severe diseases because its reach extends well beyond that of conventional drugs and offers the prospect of a curative stem cell-based therapy with limited risks as compared to allogeneic HSC transplantation. Hematopoietic stem and progenitor cells (HSPCs) are therefore ideal candidates for use in regenerative medicine and cell replacement therapies because of their ease of isolation, self-renewal capacity, and safety. Moreover, gene therapy can address unmet medical need such as in the case of cystinosis, especially this strategy overcomes the unavailability of matched HSC donor and makes the treatment potentially available to all patients.

Using a rodent model of cystinosis, $Ctns^{-/-}$ mice, it has been shown that transplantation of HSCs expressing a functional Ctns gene resulted in abundant tissue integration of bone marrow-derived cells, significant decrease of cystine accumulation (up to 97% clearance), and long-term kidney preservation. Indeed, while non-treated $Ctns^{-/-}$ mice progressed to end-stage renal failure, age-matched $Ctns^{-/-}$ mice transplanted with wild-type HSCs maintained normal renal function after more than a year post-transplant. Few to no cystine crystals were observed in the kidneys of treated mice, in contrast to non-treated $Ctns^{-/-}$ mice, in which abundant cystine crystals were consistently observed in the kidney. It has also recently been demonstrated that HSC transplantation rescues eye defects in the $Ctns^{-/-}$ mice. Treated $Ctns^{-/-}$ mice exhibited almost complete resolution of cystine crystals from the epithelial layer to the middle stroma (100% to 72% reduction, respectively), and normal corneal thickness and intraocular pressure. The impact of transplanted HSCs on the thyroid gland has also been studied. $Ctns^{-/-}$ mice present with sustained TSH activation combined with thyrocyte hypertrophy, hyperplasia and vascular proliferation. In contrast, $Ctns^{-/-}$ mice treated with transplanted HSCs exhibited normalization of cystine and TSH values and normal histology. These studies are the first proof of concept that one single HSC transplantation could prevent the multi-organ degeneration associated with cystinosis As such, the present disclosure evaluates the impact of HSPC transplantation in a mouse model for cystinosis ($Ctns^{-/-}$ mice). Using a mouse model of cystinosis ($Ctns^{-/-}$ mice), the present disclosure demonstrates that transplantation of wildtype (WT) murine hematopoietic stem cells (mHSCs) led to abundant tissue integration of bone marrow-derived cells, significant decrease of tissue cystine accumulation (up to 97% reduction) and long-term kidney, eye and thyroid preservation. Given the risks of mortality and morbidity associated with allogeneic HSC transplantation, such as graft-versus-host diseases (GVHD), an autologous transplantation protocol of HSCs was developed for ex vivo modification. Using a self-inactivated-lentiviral vector (SIN-LV) to introduce a functional version of the CTNS cDNA, pCCL-CTNS (backbone pCCL-EFS-X-WPRE), efficacy in $Ctns^{-/-}$ mice has been shown.

In vitro studies using human $CD34^+$ HSPCs isolated from peripheral blood of healthy donors and cystinosis patients have now completed, and the serial transplantation in the Ctns−/− mice has been significantly advanced. Thus, the data provided herein demonstrates efficacy of transplantation of $CD34^+$ HSCs from G-CSF mobilized peripheral blood stem cells (PBSC) of patients with cystinosis, modified by ex vivo transduction using the pCCL-CTNS LV.

Cystinosis and Danon disease both arise from loss of function mutations in transmembrane lysosomal proteins, Cystinosin and LAMP-2, respectively. In fact, Cystinosin is localized to LAMP-2 positive vesicles that are transferred during cross-correction. Thus, the present disclosure also demonstrates that bone marrow was harvested from patients with Danon disease and sorted for CD34+ hematopoeitic stems cells (HPSCs). After harvest, patient HPSCs are genetically-modified using viral transduction vectors including, but not limited to, lentiviruses and other retroviruses carrying any normal variant of the LAMP-2 gene and/or any of the LAMP-2 splice isoforms (e.g., LAMP-2A, LAMP-2B, LAMP-2C), referred to hereafter collectively as "wild-type LAMP-2" or "WT LAMP-2", is inserted into the genome of the harvested HPSCs. After infection, the viral vector inserts the wild-type LAMP-2 transgene into the host cell genome at specific sites that limit genome disruption. This insertion allows the wild-type LAMP-2 transgene to then be stably expressed by the host cell. Following translation, the wild-type LAMP-2 protein is trafficked to the lysosomal membrane where it embeds and assumes its normal intracellular position. Introduction of the wild-type LAMP-2 protein into the lysosomal membrane restores autophagic flux, allowing the cell to function normally.

After the wild-type LAMP-2 gene has been introduced, the HPSCs are transplanted back into the patient from which they were harvested. These cells then re-engraft in the patient's bone marrow and begin to produce progenitor cells. Some of these progenitor cells differentiate into monocytes carrying the wild-type LAMP-2 gene. Monocytes with the wild-type LAMP-2 gene enter the circulation and subsequently invade the peripheral tissues where they transform into tissue resident macrophages. These macrophages, through a variety of mechanisms including, but not limited to, the formation of tunneling nanotubes, vesicular release, and direct cell-cell adhesion they transfer their lysosomes, which carry membrane-bound wild-type LAMP-2 protein, to diseased peripheral cells. Wild-type LAMP-2 protein may also be transferred between macrophages and diseased peripheral cells in additional forms including, but not limited to, as free protein or bound to other proteins, membranes or organelles. The transfer of wild-type LAMP-2 containing lysosomes or wild-type LAMP-2 in other forms restores normal autophagic flux in the diseased cells resulting in partial or complete amelioration of the Danon phenotype.

Accordingly, in one aspect, the invention provides a method of treating a lysosomal transmembrane protein disease or disorder in a subject. The method includes introducing ex vivo a functional human transmembrane protein corresponding to the disorder to be treated into HSPCs of the subject, and thereafter transplanting the HSPCs into the subject, thereby treating the lysosomal transmembrane protein disease or disorder. Thus, for example, when the disease or disorder to be treated is cystinosis, the functional human transmembrane protein to be introduced is CTNS. In various embodiments, the vector is a self-inactivating (SIN)-lentivirus vector, such as, for example, pCCL-CTNS (in the case of CTNS). Likewise, when the disease or disorder to be treated is Danon disease, the functional human transmembrane protein to be introduced is LAMP-2. In various embodiments, the step of introducing may include contacting a vector comprising a polynucleotide encoding the functional protein (e.g., CTNS or LAMP-2) and a functional promoter (e.g., an ubiquitous or endogenous promoter of the functionally protein) with the HSPCs and allowing expression of the functional protein. As such, the present disclosure provides a method for autologous transplantation of ex vivo gene-modified HSPCs to introduce a functional protein associated with a specific lysosomal transmembrane protein disease or disorder.

In various embodiments, the lysosomal transmembrane protein diseases or disorders include, but are not limited to, cystinosis, Salla disease, infantile sialic acid storage disorder, Cobalamin F-type disease, neuronal ceroid lipofuscinosis (both late infantile and juvenile forms), malignant infantile osteopetrosis, mucolipidosis IV, mucopolysaccharidosis type IIIC (Sanfilippo syndrome C), Niemann-Pick Type C, and Danon disease. Without being bound by theory, in cystinosis and free sialic acid storage diseases, transporters for cystine and acidic monosaccharides, respectively, are blocked or retarded. A putative cobalamin transporter and a hybrid transporter/transferase of acetyl groups are defective in cobalamin F type disease and mucopolysaccharidosis type IIIC, respectively. In neurodegenerative forms of osteopetrosis, mutations of a proton/chloride exchanger impair the charge balance required for sustained proton pumping by the V-type ATPase, thus resulting in bone-resorption lacuna neutralization. However, the mechanism leading to lysosomal storage and neurodegeneration remains unclear. Mucolipidosis type IV is caused by mutations of a lysosomal cation channel named TRPML1; its gating properties are still poorly understood and the ion species linking this channel to lipid storage and membrane traffic defects is debated. Finally, the autophagy defect of Danon disease apparently arises from a role of LAMP2 in lysosome/autophagosome fusion, possibly secondary to a role in dynein-based centripetal motility. (Ruivo, et al. *Biochimica et Biophysica Acta* 1793 (2009) 636-649, incorporated herein by reference).

Table 1 sets forth the exemplary lysosomal transmembrane protein diseases or disorders to be treated with ex vivo introduction of corresponding functional human transmembrane proteins.

TABLE 1

| Human disease/disorder | Causative gene, locus | Protein name (aliases) | Protein size, # of transmembrane helices (TM) |
|---|---|---|---|
| Cystinosis | CTNS, 17p13 | Cystinosin | 367 aa; 7 TM |
| Salla disease, infantile sialic acid storage disorder | SLC17A5, 6q14-q15 | Sialin | 495 aa; 12 TM |

TABLE 1-continued

| Human disease/disorder | Causative gene, locus | Protein name (aliases) | Protein size, # of transmembrane helices (TM) |
|---|---|---|---|
| Cobalamin F-type disease | LMBRD1, 6q13 | LMBD1 (probable lysosomal cobalamin transporter) | 540 aa; 9 TM |
| Neuronal ceroid lipofuscinosis, late infantile variant | MFSD8, 4q28.1-q28.2 | CLN7 (major facilitator superfamily domain-containing protein 8) | 518 aa; 12 TM |
| Neuronal ceroid lipofuscinosis, juvenile form | CLN3, 16p12.1 | CLN3 (Battenin) | 438 aa; 6 TM |
| Malignant infantile osteopetrosis | CLCN7, 16p13 | ClC-7 | 805 aa; 18 TM |
| | OSTM1, 6q21 | OSTM1 | 338 aa; 1 TM |
| Mucolipidosis IV | MCOLN1, 19p13.3-p13.2 | TRPML1 (mucolipin-1, MLN1) | 580 aa; 6 TM |
| Mucopolysaccharidosis type IIIC (Sanfilippo syndrome C) | HGSNAT, 8p11.1 | HGSNAT (TMEM76) | 663 aa; 11 TM |
| Niemann-Pick Type C | NPC1, 18q11-q12 | NPC1 | 1278 aa; 11 TM |
| Danon disease | LAMP2, Xq24 | LAMP2 (LAMPB, LGP110) | 410 aa; 1 TM |

Vectors derived from lentiviruses have supplanted γ-retroviral vector for gene therapy due to their superior gene transfer efficiency and better biosafety profile. Indeed, all cases of leukemogenic complications observed to date in clinical trials or animal models involved the use of retroviral vectors with LTR containing strong enhancer/promoters that can trigger distant enhancer activation. In contrast, the third-generation of lentivirus vectors, SIN-LV, with the deletions in their LTR, contains only one internal enhancer/promoter, which reduces the incidence of interactions with nearby cellular genes, and thus, decreases the risk of oncogenic integration. SIN-LV are also designed to prevent the possibility of developing replication competent lentivirus (RCL) during production of viral supernatants with three packaging plasmids necessary for production. Lentivirus vectors efficiently transduce HSPCs and do not alter their repopulation properties, which make this type of vector an attractive vehicle for stem cell gene therapy.

Clinical trials using SIN-LV to gene-correct human HSPCs are being undertaken in the U.S. and Europe for several conditions including HIV-1, β-thalassemia, immune deficiencies, metabolic diseases and cancers. For immune deficiency disorders, 35 patients have been transplanted with SIN-LV-modified HSPCs so far. A clinical trial in patients with Adrenoleukodystrophy (ALD) has achieved stable gene correction in ~20% of hematopoietic cells in two patients. Cerebral demyelination was arrested without further progression over three years of follow-up, which represents a clinical outcome comparable to that observed after allogeneic transplantation; there was no evidence of clonal dominance. Recently, a clinical trial for Wilskott-Aldrich syndrome was reported in three patients 32 months post-transplantation. Stable and long-term engraftment of the gene-modified HSPCs (25-50%) resulted in improved platelet counts, protection from bleeding and infections, and resolution of eczema. Another clinical success was recently reported in three pre-symptomatic patients with Metachromatic Leukodystrophy. Transduced cell-derived blood cell engraftment achieved 45 to 80%, and up to 24 months later, protein activity was reconstituted to above normal values in cerebrospinal fluid associated with a clear therapeutic benefit.

The recent gene therapy successes using AAV vectors in the MCK mice not only prevented heart failure when given to presymptomatic animals, but also reversed the cardiomyopathy when given after the onset. While encouraging, this approach presents potential safety and logistic concerns: i) localized delivery by direct viral injection to affected sites poses certain challenges in accessing sites such as heart and brain and leads only to tissue-specific rescue, ii) systemic AAV delivery remains difficult in humans due to the high levels of vector necessary, leading to vector synthesis and safety concerns. In contrast, HSPC gene therapy approach has the key advantages: i) it treats all the complications by a single infusion of stem cells, ii) gene-correction occurs ex vivo in a controlled environment allowing cell characterization prior to transplantation, iii) gene-corrected HSPCs reside in the bone marrow niche after transplantation where they self-renew and become a reservoir of healthy cells for the lifespan of the patients, iv) it avoids immune reaction as compared to allogeneic transplantation. Thus, autologous HSPC gene therapy could provide a cure for lysosomal transmembrane protein diseases or disorders.

Amino acid and nucleic acid sequences for the human proteins set forth in Table 1 are known in the art. See, for example,

```
GenBank Accession No.: Y15924.1, human CTNS gene, exon 3, flanking intronic regions
and joined CDS, which provides the amino acid sequence (SEQ ID NO: 1):
MIRNWLTIFILFPLKLVEKCESSVSLTVPPVVKLENGSSTNVSLTLRPPLNATLVITFEITFRSKNITILELPDEV
VVPPGVTNSSFQVTSQNVGQLTVYLHGNHSNQTGPRIRFLVIRSSAISIINQVIGWIYFVAWSISFYPQVIMNWRR
KSVIGLSFDFVALNLTGFVAYSVFNIGLLWVPYIKEQFLLKYPNGVNPVNSNDVFFSLHAVVLTLIIIVQCCLYER
GGQRVSWPAIGFLVLAWLFAFVTMIVAAVGVITWLQFLFCFSYIKLAVTLVKYFPQAYMNFYYKSTEGWSIGNVLL
DFTGGSFSLLQMFLQSYNNDQWTLIFGDPTKFGLGVFSIVFDVVFFIQHFCLYRKRPGYDQLN

GenBank Accession No.: AJ222967.1, human CTNS mRNA, which provides the nucleic acid
sequence (SEQ ID NO: 2):
cgcctctccc aaagtctagc cgggcagggg aacgcggtgc attcctgacc ggcacctggc gaggctcatg
cgtcccgtga gggcggttcc tcgagcctgg gggcgctcag attgctttgg agacgctgag agaacctttg
cgagagcgcc ggttgacgtg cggagtgcgg ggctccgggg gactgagcag cacgagaccc catcctcccc
```

-continued tccgggtttt cacactgggc gaagggagga ctcctgagct ctgcctcttc cagtaacatt gaggattact
gtgttttgtg agagctcgct aggcgcccta agcaacagag ttctgagaaa tcgagaaaca tgataaggaa
ttggctgact atttttatcc tttttcccct gaagctcgta gagaaatgtg agtcaagcgt cagcctcact
gttcctcctg tcgtaaagct ggagaacggc agctcgacca acgtcagcct caccctgcgg ccaccattaa
atgcaaccct ggtgatcact tttgaaatca catttcgttc caaaaatatt actatccttg agctccccga
tgaagttgtg gtgcctcctg gagtgacaaa ctcctctttt caagtgacat ctcaaaatgt tggacaactt
actgtttatc tacatggaaa tcactccaat cagaccggcc cgaggatacg ctttcttgtg atccgcagca
gcgccattag catcataaac caggtgattg gctggatcta ctttgtggcc tggtccatct ccttctaccc
tcaggtgatc atgaattgga ggcggaaaag tgtcattggt ctgagcttcg acttcgtggc tctgaacctg
acaggcttcg tggcctacag tgtattcaac atcggcctcc tctgggtgcc ctacatcaag gagcagtttc
tcctcaaata ccccaacgga gtgaaccccg tgaacagcaa cgacgtcttc ttcagcctgc acgcggttgt
cctcacgctg atcatcatcg tgcagtgctg cctgtatgag cgcggtggcc agcgcgtgtc ctggcctgcc
atcggcttcc tggtgctcgc gtggctcttc gcatttgtca ccatgatcgt ggctgcagtg ggagtgatca
cgtggctgca gtttctcttc tgcttctcct acatcaagct cgcagtcacg ctggtcaagt attttccaca
ggcctacatg aacttttact acaaaagcac tgagggctgg agcattggca acgtgctcct ggacttcacc
gggggcagct tcagcctcct gcagatgttc ctccagtcct acaacaacga ccagtggacg ctgatcttcg
gagacccaac caagtttgga ctcggggtct tctccatcgt cttcgacgtc gtcttcttca tccagcactt
ctgtttgtac agaaagagac cggggtatga ccagctgaac tagcacccag ggacccagtg tacccagcct
ctggcctcgt gccctgctgg ggaaggcctc acccagcgaa ggccggagaa gcggttgggc cctggcacac
agggctggct cagtgtgcgg acagaggaga ccactctgct cctggggcca gaggccattc aatagcctgc
cttcgtccgg gcccctcctg ggcctccccg gccaggcacg tggcaccgtc gccttgacac cgccatctct
tttctttaag gcttcaggca gcgcgcacag gctctggcag ccgtctcagg caggactggg caccaagctt
gcagccgaag gccttgcccc aaactaccag cgtttctgca agcagcttga agggctgacc ttgcagccgg
gtgagccaag ggcactttgc tgccaccgct gcattcccag agatcaagca gcccggtgcc gtggccagtg
aactcagagg tgctggtgga cgggctagga ctttggggtt aggccatggg gctctttctc tgaaggccac
tttcctgacg tactctctgt acataactca gcgtccgtga ctgcagtaac agccagccct acccagagta
tttctgagcc atgaggggcc caccagattg gttctgaatt ggattcatgc ccagcgcatt agcatagtaa
ctcctttcag atttttgga gggacgtttg gaagtggctt actctcttct gccctctctc ctacctccac
cttctcagat gagccccatc tgagcacatc cagctgctcc ttacccagca tctggagtac aggacatagc
tctctcctgc taccagtctg tgccttagag gtcgttaggc ctgccaaacg gcgaccagct cccctggagc
gagggcaggc cccttccctc tctttcccca gacacctact tgagactcac caatttctgg cctgttcagg
agcctcagat aagtatttgt acttgagacc acctcacaca atctgtatgg gcccaaccct gatctcaaac
ctccttccct ctgcccaaag ctgtccttcc tatggcagga ggggtggggg tcccaggacg tgcctcatac
atgacttgag cttgtcagtc cactgagttt ccttctacga gatcaacgcg aggggcctgt atcttgaatt
aaagcctact cgcttccttt c GenBank Accession No.: CAB62540.1, human sialin, which provides the amino acid sequence (SEQ ID NO: 3):

MRSPVRDLAR NDGEESTDRT PLLPGAPRAE AAPVCCSARY NLAILAFFGF FIVYALRVNL SVALVDMVDS
NTTLEDNRTS KACPEHSAPI KVHHNQTGKK YQWDAETQGW ILGSFFYGYI ITQIPGGYVA SKIGGKMLLG
FGILGTAVLT LFTPIAADLG VGPLIVLRAL EGLGEGVTFP AMHAMWSSWA PPLERSKLLS ISYAGAQLGT
VISLPLSGII CYYMNWTYVF YFFGTIGIFW FLLWIWLVSD TPQKHKRISH YEKEYILSSL RNQLSSQKSV
PWVPILKSLP LWAIVVAHFS YNWTFYTLLT LLPTYMKEIL RFNVQENGFL SSLPYLGSWL CMILSGQAAD
NLRAKWNFST LCVRRIFSLI GMIGPAVFLV AAGFIGCDYS LAVAFLTIST TLGGFCSSGF SINHLDIAPS
YAGILLGITN TFATIPGMVG PVIAKSLTPD NTVGEWQTVF YIAAAINVFG AIFFTLFAKG EVQNWALNDH
HGHRH

GenBank Accession No.: AJ387747.1, human sialin mRNA, which provides the nucleic acid sequence (SEQ ID NO: 4):

cggctacttt gcgccaatcc tacgagaact cccagaactc cgcttcccta gtccaaccca agccagagtt
gcccacacct aagatggcgg cggggggcgg agtcggcgcg gccgcctctg ggcgggaccg cggggactag
acgtggccgc ggggcggtgt catcgccccc gccccgcccg gtccagccag ctcggcccgg gggcttcggg
ctgtcgggcc ggcgctccct tctctgccag gtggcgagta cacctgctca cgtaggcgtc atgaggtctc
cggttcgaga cctggcccgg aacgatggcg aggagagcac ggaccgcacg cctcttctac cgggcgcccc
acgggccgaa gccgctccag tgtgctgctc tgctcgttac aacttagcaa ttttggcctt ttttggtttc
ttcattgtgt atgcattacg tgtgaatctg agtgttgcgt tagtggatat ggtagattca aatacaactt
tagaagataa tagaacttcc aaggcgtgtc cagagcattc tgctcccata aaagttcatc ataatcaaac
gggtaagaag taccaatggg atgcagaaac tcaaggatgg attctcggtt ccttttttta tggctacatc
atcacacaga ttcctggagg atatgttgcc agcaaaatag gggggaaaat gctgctagga tttgggatcc
ttggcactgc tgtcctcacc ctgttcactc ccattgctgc agatttagga gttggaccac tcattgtact
cagagcacta gaaggactag gagagggtgt tacatttcca gccatgcatg ccatgtggtc ttcttgggct
ccccctcttg aaagaagcaa acttcttagc atttcatatg caggagcaca gcttgggaca gtaatttctc
ttcctctttc tggaataatt tgctactata tgaattggac ttatgtcttc tactttttg gtactattgg
aatattttgg tttcttttgt ggatctggtt agttagtgac acaccacaaa aacacaagag aatttcccat
tatgaaaagg aatacattct ttcatcatta agaaatcagc tttcttcaca gaagtcagtg ccgtgggtac
ccattttaaa atccctgcca ctttgggcta tcgtagttgc acacttttct tacaactgga ctttttatac
tttattgaca ttattgccta cttatatgaa ggagatccta aggttcaatg ttcaagagaa tgggttttta
tcttcattgc cttatttagg ctcttggtta tgtatgatcc tgtctggtca agctgctgac aatttaaggg
caaaatggaa tttttcaact ttatgtgttc gcagaatttt tagccttata ggaatgattg gacctgcagt
attcctggta gctgctggct tcattggctg tgattattct ttggccgttg ctttcctaac tatatcaaca
acactgggag gcttttgctc ttctggattt agcatcaacc atctggatat tgctccttcg tatgctggta
tcctcctggg catcacaaat acatttgcca ctattccagg aatggttggg cccgtcattg ctaaaagtct
gacccctgat aacactgttg gagaatggca aaccgtgttc tatattgctg ctgctattaa tgtttttggt
gccattttct ttacactatt cgccaaaggt gaagtacaaa actgggctct caatgatcac catggacaca
gacactgaag gaaccaataa ataatcctgc ctctattaat gtatttttat ttatcatgta acctcaaagt
gccttctgta ttgtgtaagc attctatgtc tttttttaat tgtacttgta ttagattttt aaggcctata
atcatgaaat atcactagtt gccagaataa taaaatgaac tgtgtttaat tatgaataat atgtaagcta
ggacttctac tttaggttca catacctgcc tgctagtcgg gcaacatgaa gtaggacagt tctgttgatt
ttttagggcc atactaaagg gaatgagctg aaacagacct cctgatacct ttgcttaatt aaactagatg -continued ataattctca ggtactgata aacacctgtt gttgttcact ttcctcataa aaattgtcag ctctctctga
cacttagacc tcaaacttta gcatctctgt ggagctgcca tccactgtat aatttcgcct ggcaactgga
ctgaggggag tgtgcccagg cagctgccaa gcactccctc cctggcttca gggtcagagt gcccagcgtt
tatcagaggc agcatccaag cccagagcca gtgtcgactc ttcggctggt gcctttcctc tgaggggcta
tcaatgtgta gataaagccc tgagtaggca agagcagtga gatccactgc tatggtcttg atacatcctc
aaactttccc ttcccagcac agaggaatat tggctggcat gcaacctgca aaagaaaaat gc GenBank Accession No.: CCP79466.1, human LMBD1, which provides the amino acid sequence (SEQ ID NO: 5):

GAASAELVIGWCIFGPLLLAIFAFCWIYVRKYQSQRESEVVSTITAIFSLAIALITSALLPVDIFLVSYMKNQNGT
FKDWANANVSRQIEDTVLYGYYTLYSVILFCVFFWIPFVYFYYEEKDDDDTSKCTQIKTAFKYTLGFAVICALLLL
VGAFVPLNVPNNKNSTEWEKVKFLFEELGSSHGLAALSFSISSLTLIGMLAAITYTAYGMSALPLNLIKGTRSAAY
ERLENTEDIEEVEQHIQTIKSKSKDGRPLPARDKRALKQFEERLRTLRKRERHLEYIENSWWTKFCGALRPLKIIW
GIFFILVALLFIISLFLSNLDKALHSAGIDSGFIIFGANLSNPLNMLLPVLQTVFPLDYILITIIIMYFIFTSMAG
IRNIGIWFFWVRLYKIRRGRTRPQALLFLCMILLLIVLHTSYMIYSLAPQYVMYGSQNYLIESNITYDDHKNNSAF
PVPKRCDADAPEDQCTVTRTYLFLHKFWFFSAAYYFGNWAFLVVFLIGLIVSCCKGKKSVIEGVDEDDSDISDDEP
SVYSV

GenBank Accession No.: HAAF01007642.1, human LMBD1 transcribed RNA, which provides the nucleic acid sequence (SEQ ID NO: 6):

ggcgcggctt cggcggagct ggtgatcggc tggtgcatat ttggcccctt actactggct atttttgcat
tctgttggat atatgttcgt aaataccaaa gtcagcggga aagtgaagtt gtctccacca taacggcaat
tttttctctg gcgattgcac ttatcacatc agcacttctt ccagtggata tatttttggt ttcttacatg
aaaaatcaaa atggtacatt taaggactgg gccaatgcta atgtcagcag acagatcgag gacactgtgt
tatatggtta ctacacctta tattctgtta tattattctg tgtgtttttc tggatccctt ttgtctactt
ctactatgaa gaaaaggatg atgatgatac tagtaaatgt actcaaatta aaactgcatt caagtatact
ttgggatttg ctgtaatttg tgcacttctt cttttagttg gagcttttgt tcctctaaat gttcctaata
acaaaaattc tacagagtgg gaaaaagtga agttcctgtt tgaagaactt ggaagtagtc atggtttagc
tgcattgtca ttttctatta gttctctgac cttgattgga atgttggcag ctataactta cacagcctat
ggcatgtctg cattaccttt aaatctaata aaaggcacta gaagcgctgc ttacgaacgt ttagaaaaca
ctgaagacat tgaagaagtg gagcaacaca ttcaaacgat taaatcaaaa agcaaagatg gtcggccttt
gccagcaagg gataaacgcg ccttaaaaca atttgaagaa aggttaagaa cacttaggaa aagagagagg
cacttagaat acattgaaaa cagctggtgg acaaaatttt gtggtgctct gcgtcccctg aagatcattt
ggggaatatt tttcatctta gttgcattgc tgtttataat ttctctcttc ctgtcaaatt tggataaagc
ccttcattca gctggaatag attctggttt tataattttt ggagctaact tgagtaatcc actgaatatg
cttttgcctg tactacaaac agtgtttcct cttgattata ttcttataac aattattatt atgtacttta
tttttacttc aatggcggga attcgaaata tcggcatatg gttcttttgg gttagactat ataaaattag
aagaggtaga accaggcccc aggccctctt atttctttgc atgatacttc tgcttattgt ccttcacact
agctacatga tttatagtct tgctccccaa tatgtcatgt atggaagcca aaattactta atagagagca
atataactta tgatgaccat aaaaacaatt cagccttccc tgtgccaaag agatgtgatg ctgatgcccc
tgaagaccaa tgtactgtta cgcggacata cctgttcctt cacaagttct ggttctttag tgctgcatac
tattttggta actgggcttt tcttgtggta ttcttgattg gattaattgt atcctgttgt aaagggaaga
aatcagtcat tgaaggagta gatgaagatg attcagacat aagtgatgat gagccctctg tctattctgt
ttgagagcct ctgtcttagg ggttttataa tgctgactga atgtctatta tgcatttttt aaagtgttaa
actaacatta ggatgaactg actagcttca tcaaaaatgg gagcatggct attaaaaaaa ctatattttt
tatgttatct gaagtaacat tattgtatca tagattaaca tttaaaattg ctgtaataat tctatgtaaa
tataaaacta tggactttgt gagggaatgt ttgtggaaat ctttttttctc tagtgtataa tagtgttgaa
ttgattaaaa gtcttccaga attaatattc cctcttgtca cttcttaaaa acataataaa tcacttctac
ctgtgcaaaa aaaaaaaaa GenBank Accession No.: AAH295036.1, human CLN7, which provides the amino acid sequence (SEQ ID NO: 7):

MAGLRNESEQ EPLLGDTPGS REWDILETEE HYKSRWRSIR ILYLTMFLSS VGFSVVMMSI WPYLQKIDPT
ADTSFLGWVI ASYSLGQMVA SPIFGLWSNY RPRKEPLIVS ILISVAANCL YAYLHIPASH NKYYMLVARG
LLGIGAGNVA VVRSYTAGAT SLQERTSSMA NISMCQALGF ILGPVFQTCF TFLGEKGVTW DVIKLQINMY
TTPVLLSAFL GILNIILILA ILREHRVDDS GRQCKSINFE EASTDEAQVP QGNIDQVAVV AINVLFFVTL
FIFALFETII TPLTMDMYAW TQEQAVLYNG IILAALGVEA VVIFLGVKLL SKKIGERAIL LGGLIVVWVG
FFILLPWGNQ FPKIQWEDLH NNSIPNTTFG EIIIGLWKSP MEDDNERPTG CSIEQAWCLY TPVIHLAQFL
TSAVLIGLGY PVCNLMSYTL YSKILGPKPQ GVYMGWLTAS GSGARILGPM FISQVYAHWG PRWAFSLVCG
IIVLTITLLG VVYKRLIALS VRYGRIQE

GenBank Accession No.: BC029503.1, human CLN7 mRNA, which provides the nucleic acid sequence (SEQ ID NO: 8):

aggttacaag cagcagatcc caccttcagt cctggctctg acaagccctc cagcttcacg ccacccggga
tgggagaaag caggtgtcgc gagagttggg cgcaagacgc cttgtaggga gtgtaactat ggccggcctg
cggaacgaaa gtgaacagga gccgctctta ggcgacacac ctggaagcag agaatgggac attttagaga
ctgaagagca ttataagagc cgatggagat ctattaggat tttatatctt actatgtttc tcagcagtgt
agggttttct gtagtgatga tgtccatatg gccatatctc caaaagattg atccgacagc tgatacaagt
tttttgggct gggttattgc ttcatatagt cttggccaaa tggtagcttc acctatattt ggtttatggt
ctaattatag accaagaaaa gagcctctta ttgtctccat cttgatttcc gtggcagcca actgcctcta
tgcatatctc cacatcccag cttctcataa taaatactac atgctggttg ctcgtggatt gttgggaatt
ggagcaggaa atgtagcagt tgttagatca tatactgctg gtgctacttc ccttcaggaa agaacaagtt
ccatggcaaa cataagcatg tgtcaagcat taggttttat tctaggtcca gtttttcaga cttgttttac
attccttgga gaaaaaggtg tgacatggga tgtgattaaa ctgcagataa acatgtatac aacaccagtt
ttacttagcg ccttcctggg aattttaaat attattctga tccttgccat actaagagaa catcgtgtgg
atgactcagg aagacagtgt aaaagtatta attttgaaga agcaagtaca gatgaagctc aggttcccca
aggaaatatt gaccaggttg ctgttgtggc catcaatgtt ctgttttttg tgactctatt tatctttgcc
ctttttgaaa ccatcattac tccattaaca atggatatgt atgcctggac tcaagaacaa gctgtgttat
ataatggcat aatacttgct gctcttgggg ttgaagccgt tgttattttc ttaggagtta agttgctttc caaaaagatt ggcgagcgtg ctattctact gggaggactc atcgttgtat gggttggctt ctttatcttg
ttaccttggg gaaatcaatt tcccaaaata cagtgggaag atttgcacaa taattcaatc cctaatacca
catttgggga aattattatt ggtctttgga agtctccaat ggaagatgac aatgaaagac caactggttg
ctcgattgaa caagcctggt gcctctacac cccggtgatt catctggccc agttccttac atcagctgtg
ctaataggat taggctatcc agtctgcaat cttatgtcct atactctata ttcaaaaatt ctaggaccaa
aacctcaggg tgtatacatg ggctggttaa cagcatctgg aagtggagcc cggattcttg ggcctatgtt
catcagccaa gtgtatgctc actggggacc acgatgggca ttcagcctgg tgtgtggaat aatagtgctc
accatcaccc tcctgggagt ggtttacaaa agactcattg ctctttctgt aagatatggg aggattcagg
aataaactag ctaagactgt gatggaaact acttgctgtg tggcacttcc tggtctaaag ctctgctaga
caattgcggt gagccagtct ccaagaatca gactacagat attgcagatt ttgaagaaca agaacatatg
ttgaataaca gagagaattc tacatgtcat tgtgaatagt aggttatata aaaacatact agatgataat
ttcaaaaaaa aaaaaaaaa GenBank Accession No.: AAB51075.1, human CLN3, which provides the amino acid sequence (SEQ ID NO: 9):
MGGCAGSRRRFSDSEGEETVPEPRLPLLDHQGAHWKNAVGFWLLGLCNNFSYVVMLSAAHDILSHKRTSGNQSHVD
PGPTPIPHNSSSRFDCNSVSTAAVLLADILPTLVIKLLAPLGLHLLPYSPRVLVSGICAAGSFVLVAFSHSVGTSL
CGVVFASISSGLGEVTFLSLTAFYPRAVISWWSSGTGGAGLLGALSYLGLTQAGLSPQQTLLSMLGIPALLLASYF
LLLTSPEAQDPGGEEEAESAARQPLIRTEAPESKPGSSSSLSLRERWTVFKGLLWYIVPLVVVYFAEYFINQGLFE
LLFFWNTSLSHAQQYRWYQMLYQAGVFASRSSLRCCRIRFTWALALLQCLNLVFLLADVWFGFLPSIYLVFLIILY
EGLLGGAAYVNTFHNIALETSDEHREFAMAATCISDTLGISLSGLLALPLHDFLCQLS GenBank Accession No.: U32680.1, human CLN3 mRNA complete cds, which provides the nucleic acid sequence (SEQ ID NO: 10):
cccctagaca agccggagct gggaccggca atcgggcgtt gatccttgtc acctgtcgca gaccctcatc
cctcccgtgg gagccccctt tggacactct atgaccctgg accctcgggg gacctgaact tgatgcgatg
ggaggctgtg caggctcgcg gcggcgcttt tcggattccg agggggagga gaccgtcccg gagccccggc
tccctctgtt ggaccatcag ggcgcgcatt ggaagaacgc ggtgggcttc tggctgctgg gcctttgcaa
caacttctct tatgtggtga tgctgagtgc cgcccacgac atccttagcc acaagaggac atcgggaaac
cagagccatg tggacccagg cccaacgccg atcccccaca acagctcatc acgatttgac tgcaactctg
tctctacggc tgctgtgctc ctggcggaca tcctccccac actcgtcatc aaattgttgg ctcctcttgg
ccttcacctg ctgccctaca gcccccgggt tctcgtcagt gggatttgtg ctgctggaag cttcgtcctg
gttgcctttt ctcattctgt ggggaccagc ctgtgtggtg tggtcttcgc tagcatctca tcaggccttg
gggaggtcac cttcctctcc ctcactgcct tctaccccag ggccgtgatc tcctggtggt cctcagggac
tgggggagct gggctgctgg gggccctgtc ctacctgggc ctcacccagg ccggcctctc ccctcagcag
accctgctgt ccatgctggg tatccctgcc ctgctgctgg ccagctattt cttgttgctc acatctcctg
aggcccagga ccctggaggg gaagaagaag cagagagcgc agcccggcag cccctcataa gaaccgaggc
cccggagtcg aagccaggct ccagctccag cctctccctt cgggaaaggt ggacagtatt caagggtctg
ctgtggtaca ttgttccctt ggtcgtagtt tactttgccg agtatttcat taaccaggga ctttttgaac
tcctcttttt ctggaacact tccctgagtc acgctcagca ataccgctgg taccagatgc tgtaccaggc
tggcgtcttt gcctcccgct cttctctccg ctgctgtcgc atccgtttca cctgggccct ggccctgctg
cagtgcctca acctggtgtt cctgctggca gacgtgtggt tcggctttct gccaagcatc tacctcgtct
tcctgatcat tctgtatgag gggctcctgg gaggcgcagc ctacgtgaac accttccaca acatcgccct
ggagaccagt gatgagcacc gggagtttgc aatggcggcc acctgcatct ctgacacact ggggatctcc
ctgtcggggc tcctggcttt gcctctgcat gacttcctct gccagctctc ctgatactcg ggatcctcag
gacgcaggtc acattcacct gtgggcagag ggacaggtca gacacccagg cccaccccag agaccctcca
tgaactgtgc tcccagcctt cccggcaggt ctgggagtag ggaagggctg aagccttgtt tccttgcagg
ggggccagcc attgtctccc acttggggag tttcttcctg gcatcatgcc ttctgaataa atgccgattt
tgtccatgg GenBank Accession No.: AAF34711.1, human CLCN7, which provides the amino acid sequence (SEQ ID NO: 11):
MANVSKKVSWSGRDRDDEEAAPLLRRTARPGGGTPLLNGAGPGAARQSPRSALFRVGHMSSVELDDELLDPDMDPP
HPFPKEIPHNEKLLSLKYESLDYDNSENQLFLEEERRINHTAFRTVEIKRWVICALIGILTGLVACFIDIVVENLA
GLKYRVIKGNIDKFTEKGGLSFSLLLWATLNAAFVLVGSVIVAFIEPVAAGSGIPQIKCFLNGVKIPHVVRLKTLV
IKVSGVILSVVGGLAVGKEGPMIHSGSVIAAGISQGRSTSLKRDFKIFEYFRRDTEKRDFVSAGAAAGVSAAFGAP
VGGVLFSLEEGASFWNQFLTWRIFFASMISTFTLNFVLSIYHGNMWDLSSPGLINFGRFDSEKMAYTIHEIPVFIA
MGVVGGVLGAVFNALNYWLTMFRIRYIHRPCLQVIEAVLVAAVTATVAFVLIYSSRDCQPLQGGSMSYPLQLFCAD
GEYNSMAAAFFNTPEKSVVSLFHDPPGSYNPLTLGLFTLVYFFLACWTYGLTVSAGVFIPSLLIGAAWGRLFGISL
SYLTGAAIWADPGKYALMGAAAQLGGIVRMTLSLTVIMMEATSNVTYGFPIMLVLMTAKIVGDVFIEGLYDMHIQL
QSVPFLHWEAPVTSHSLTAREVMSTPVTCLRRREKVGVIVDVLSDTASNHNGFPVVEHADDTQPARLQGLILRSQL
IVLLKHKVFVERSNLGLVQRRLRLKDFRDAYPRFPPIQSIHVSQDERECTMDLSEFMNPSPYTVPQEASLPRVFKL
FRALGLRHLVVVDNRNQVVGLVTRKDLARYRLGKRGLEELSLAQT GenBank Accession No.: AF224741.1, human CLCN7 mRNA complete cds, which provides the nucleic acid sequence (SEQ ID NO: 12):
gccggcgctt cccggccggt gtcgctccgc ggcgggccat ggccaacgtc tctaagaagg tgtcctggtc
cggccgggac cgggacgacg aggaggcggc gccgctgctg cggaggacgg cgcggcccgg cggggggacg
ccgctgctga acggggctgg gcccggggct gcgcgccagt caccacgttc tgcgcttttc cgagtcggac
atatgagcag cgtggagctg gatgatgaac ttttggaccc ggatatggac cctccacatc ccttccccaa
ggagatccca cacaacgaga agctcctgtc cctcaagtat gagagcttgg actatgacaa cagtgagaac
cagctgttcc tggaggagga gcggcggatc aatcacacgg ccttccggac ggtggagatc aagcgctggg
tcatctgcgc cctcattggg atcctcacgg gcctcgtggc ctgcttcatt gacatcgtgg tggaaaacct
ggctggcctc aagtacaggg tcatcaaggg caatatcgac aagttcacag agaagggcgg actgtccttc
tccctgttgc tgtgggccac gctgaacgcc gccttcgtgc tcgtgggctc tgtgattgtg gctttcatag
agccggtggc tgctggcagc ggaatccccc agatcaagtg cttcctcaac ggggtgaaga tcccccacgt
ggtgcggctc aagacgttgg tgatcaaagt gtccggtgtg atcctgtccg tggtcggggg cctggccgtg
ggaaaggaag ggccgatgat ccactcaggt tcagtgattg ccgccgggat ctctcaggga aggtcaacgt
cactgaaacg agatttcaag atcttcgagt acttccgcag agacacagag aagcgggact tcgtctccgc

```
aggggctgcg gccggagtgt cagcggcgtt tggagccccc gtgggtgggg tcctgttcag cttggaggag
ggtgcgtcct tctggaacca gttcctgacc tggaggatct tctttgcttc catgatctcc acgttcaccc
tgaattttgt tctgagcatt taccacggga acatgtggga cctgtccagc ccaggcctca tcaacttcgg
aaggtttgac tcggagaaaa tggcctacac gatccacgag atcccggtct tcatcgccat gggcgtggtg
ggcggtgtgc ttggagctgt gttcaatgcc ttgaactact ggctgaccat gtttcgaatc aggtacatcc
accggccctg cctgcaggtg attgaggccg tgctggtggc cgccgtcacg gccacagttg ccttcgtgct
gatctactcg tcgcgggatt gccagcccct gcagggggc tccatgtcct acccgctgca gctcttttgt
gcagatggcg agtacaactc catggctgcg gccttcttca acaccccgga gaagagcgtg gtgagcctct
tccacgaccc gccaggctcc tacaaccccc tgaccctcgg cctgttcacg ctggtctact tcttcctggc
ctgctggacc tacgggctca cggtgtctgc cggggtcttc atcccgtccc tgctcatcgg ggctgcctgg
ggccggctct ttgggatctc cctgtcctac ctcacggggg cggcgatctg ggcggacccc ggcaaatacg
ccctgatggg agctgctgcc cagctgggcg ggattgtgcg gatgacactg agcctgaccg tcatcatgat
ggaggccacc agcaacgtga cctacggctt ccccatcatg ctggtgctca tgaccgccaa gatcgtgggc
gacgtcttca ttgagggcct gtacgacatg cacattcagc tgcagagtgt gcccttcctg cactgggagg
ccccggtcac ctcacactca ctcactgcca gggaggtgat gagcacacca gtgacctgcc tgaggcggcg
tgagaaggtc ggcgtcattg tggacgtgct gagcgacacg gcgtccaatc acaacggctt ccccgtggtg
gagcatgccg atgacaccca gcctgcccgg ctccagggcc tgatcctgcg ctcccagctc atcgttctcc
taaagcacaa ggtgtttgtg gagcggtcca acctgggcct ggtacagcgg cgcctgaggc tgaaggactt
ccgagacgcc tacccgcgct tcccacccat ccagtccatc cacgtgtccc aggacgagcg ggagtgcacc
atggacctct ccgagttcat gaacccctcc ccctacacgg tgccccagga ggcgtcgctc ccacgggtgt
tcaagctgtt ccgggccctg ggcctgcggc acctggtggt ggtggacaac cgcaatcagg ttgtcgggtt
ggtgaccagg aaggacctcg ccaggtaccg cctgggaaag agaggcttgg aggagctctc gctggcccag
acgtgaggcc cagccctgcc cataatgggc actggcgctg gcaccccggc ccttctgcat ttcctcccgg
agtcactggt ttctcggccc aaaccatgct ccccagcagt ggcaatggcg agcaccctgc agctgggcgg
gcaggcggca ggcgcggaac tgaccctctc gcgggactga ccctgttgtg ggcagtggtc tccccccttg
gcgcctcctt gcgcaggccc agcctccact ctcctcgtct aggtttcttt acctccaggg atcagctgtg
tgtgtgtgac ctccctaccg ggctatcggc ctcttgggag ccagcggcag ggccggcacc tgcgtgcctg
tgcccgtgtg cgtgagacag agcccttgcc cctgctgctg ccccgagggc tgccctgccc tggaagggcc
cctctgcctc cacaccagtg gagtcttcga gacttgggag ctgcttggcc tcattttcag ccatgagcag
acggcctgtg gtccctgggc ctgaggcacg gactcgtagc accagggttt ggaggctgcg accgccccgg
agagcagctt cacactggcg ccacagagga gccccacgtg cactccccgg cctgcatccg gcttgggtac
acaggcccag aggactgggg tgactcacgg gccctgtgct gtgatgttga gagctgagaa aaacctccaa
ggccctgagc cccatgccca gccctgcctt ggtcccccaa tccccagagc ttggagtctg ggccccacac
ccagccctgc cttggtccct gagcctcaaa gcgtggaatt gctgccctgt ggacact
```

GenBank Accession No.: AAH68581.1, human OSTM1, which provides the amino acid sequence (SEQ ID NO: 13):

```
MEPGPTAAQR RCSLPPWLPL GLLLWSGLAL GALPFGSSPH RVFHDLLSEQ QLLEVEDLSL SLLQGGGLGP
LSLPPDLPDL DPECRELLLD FANSSAELTG CLVRSARPVR LCQTCYPLFQ QVVSKMDNIS RAAGNTSESQ
SCARSLLMAD RMQIVVILSE FFNTTWQEAN CANCLTNNSE ELSNSTVYFL NLFNHTLTCF EHNLQGNAHS
LLQTKNYSEV CKNCREAYKT LSSLYSEMQK MNELENKAEP GTHLCIDVED AMNITRKLWS RTFNCSVPCS
DTVPVIAVSV FILFLPVVFY LSSFLHSEQK KRKLILPKRL KSSTSFANIQ ENSN
```

GenBank Accession No.: BC068581.1, human OSTM1 mRNA, which provides the nucleic acid sequence (SEQ ID NO: 14):

```
ggctgtccgc ggtgccggct gggggcggag aggcggcggt gggctccctg gggtgtgtga gcccggtgat
ggagccgggc ccgacagccg cgcagcggag gtgttcgttg ccgccgtggc tgccgctggg gctgctgctg
tggtcggggc tggccctggg cgcgctcccc ttcggcagca gtccgcacag ggtcttccac gacctcctgt
cggagcagca gttgctggag gtggaggact tgtccctgtc cctcctgcag ggtggagggc tggggcctct
gtcgctgccc ccggacctgc cggatctgga tcctgagtgc cgggagctcc tgctggactt cgccaacagc
agcgcagagc tgacagggtg tctggtgcgc agcgcccggc ccgtgcgcct ctgtcagacc tgctaccccc
tcttccaaca ggtcgtcagc aagatggaca acatcagccg agccgcgggg aatacttcag agagtcagag
ttgtgccaga agtctcttaa tggcagatag aatgcaaata gttgtgattc tctcagaatt ttttaatacc
acatggcagg aggcaaattg tgcaaattgt ttaacaaaca acagtgaaga attatcaaac agcacagtat
atttccttaa tctatttaat cacaccctga cctgctttga acataacctt caggggaatg cacatagtct
tttacagaca aaaaattatt cagaagtatg caaaaactgc cgtgaagcat acaaaactct gagtagtctg
tacagtgaaa tgcaaaaaat gaatgaactt gagaataagg ctgaacctgg aacacattta tgcattgatg
tggaagatgc aatgaacatc actcgaaaac tatggagtcg aactttcaac tgttcagtcc cttgcagtga
cacagtgcct gtaattgctg tttctgtgtt cattctcttt ctacctgttg tcttctacct tagtagcttt
cttcactcag agcaaaagaa acgcaaactc attctgccca aacgtctcaa gtccagtacc agttttgcaa
atattcagga aaattcaaac tgagacctac aaaatggaga attgacatat cacgtgaatg aatggtggaa
gacacaactt ggtttcagaa agaagataaa ctgtgatttg acaagtcaag ctcttaagaa atacaaggac
ttcagatcca tttttaaata agaattttcg atttttcttt ccttttccac ttctttctaa cagatttgga
tatttttaat ttccaggcat agcagtgtta tctattttaa tgtgtatttg tcacaataac agaacatgca
agaacaatca ttattttatt ttataggcat ttgattacta ttctagactt ctggtatctt cttactaaca
taagtatctc aagtagaaaa gtttttgaaa actaacattt aaaaattaat cagttacagt aaagactttg
aaaaagaaat gtacttgtta ggaagtagct taattacccc ccattgcagt attattgtta tatatatagt
taatatgttg tacatcacaa taatatataa ttcagtctct agtttcccta gagtcatttt tgaaaccact
gattgcaaac ctccctgaca atttttaaaa gtagtaagcc acattacatt tatctttgta aaaagattta
tggtaactgg tttcttactt gacttttata aatagtattt tacatcttat ttttgccttt atttcataag
taatttaaaa atcactggat tgctttatta tattcagggc aatatggatt atttttatac caaggatttg
catcgtgaat taaattaagt tatttggcaa tttataattt attactactt taaatcaaat gtagcattat
cacactgtat ttaaattgtc atttttttaaa ggaatatttt cttcttaaga tatatagagg attttggaga
agagagacag gaggggtaaa accagcttaa ggttcagcga gcagaaaggg acctgagagg atgctcactg
taagactgtt ggacagtggt gtgtattgag gggatgaatc ggaacgatag tctcatgcag aaaatagtga
gattaagatc atccttattg tttctaaatt atttcaatca gatgaaagtg atacgattga aatgaaatca
catagttcgt gctcagaaat tctattttgg tatgtttgta ttagccttta gaaaaaacac tccgtttcag
aattgttcac agttttattt cttaggtttt tagagttcag gatttcattt attaatttct tcttgctttt
ttggtggaaa taggctttgt tgtaaacatt aagaatataa aatctcctct atatagaaac aagaattttg
```

-continued

```
ttaaaaagag aatttgaatc ccttcctata ctataaaatg ctctataggg agacaaagtg tttctttttt
cttttatgtt tactgtttat gtggagtgaa atataaggct cttggatgta taacatactc aaaagctgtt
acactttctc tgatctgctg tgatccactg aaaatgtgct ggggtttgtt ctgctgtcac tgtttatgct
gctggaactt agcactgtct tgatttgaag catatgattg agagccattt gaagcaatct tcattaatgc
agataaaaca agtttacatg tgcagagtta gaaaatgaca tgttcaattc tgtaagtggt gactttttga
gcacctttca gtattatgta tttgtaaaaa ccattgtttt tggatataaa gctaataagc actttaaaaa
aaaaaaaaaa aaaaaaaaaa aaaaaaaaaa aaaaaaaaaa aaaaaaaaaa aaagaaaaaa aaaaaaaaa
```

GenBank Accession No.: AAG00797.1, human MCOLN1, which provides the amino acid sequence (SEQ ID NO: 15):

```
MTAPAGPRGSETERLLTPNPGYGTQAGPSPAPPTPPEEEDLRRRLKYFFMSPCDKFRAKGRKPCKLMLQVVKILVV
TVQLILFGLSNQLAVTFREENTIAFRHLFLLGYSDGADDTFAAYTREQLYQAIFHAVDQYLALPDVSLGRYAYVRG
GGDPWTNGSGLALCQRYYHRGHVDPANDTFDIDPMVVTDCIQVDPPERPPPPPSDDLTLLESSSSYKNLTLKFHKL
VNVTIHFRLKTINLQSLINNEIPDCYTFSVLITFDNKAHSGRIPISLETQAHIQECKHPSVFQHGDNSFRLLFDVV
VILTCSLSFLLCARSLLRGFLLQNEFVGFMWRQRGRVISLWERLEFVNGWYILLVTSDVLTISGTIMKIGIEAKNL
ASYDVCSILLGTSTLLVWVGVIRYLTFFHNYNILIATLRVALPSVMRFCCCVAVIYLGYCFCGWIVLGPYHVKFRS
LSMVSECLFSLINGDDMFVTFAAMQAQQGRSSLVWLFSQLYLYSFISLFIYMVLSLFIALITGAYDTIKHPGGAGA
EESELQAYIAQCQDSPTSGKFRRGSGSACSLLCCCGRDPSEEHSLLVN
```

GenBank Accession No.: AF287269.1, human MCOLN1 mRNA, complete cds, which provides the nucleic acid sequence (SEQ ID NO: 16):

```
agatcagctg atgccggagg gtttgaagcc gcgccgcgag ggagcgaggt cgcagtgaca gcggcgggcg
atcggaccca ggctgccccg ccgtacccgc ctgcgtcccg cgctcccgcc ccagcatgac agccccggcg
ggtccgcgcg gctcagagac cgagcggctt ctgaccccca accccgggta tgggacccag gcggggcctt
caccggcccc tccgacaccc ccagaagagg aagaccttcg ccgtcgtctc aaatactttt tcatgagtcc
ctgcgacaag tttcgagcca agggccgcaa gccctgcaag ctgatgctgc aagtggtcaa gatcctggtg
gtcacggtgc agctcatcct gtttgggctc agtaatcagc tggctgtgac attccgggaa gagaacacca
tcgccttccg acacctcttc ctgctgggct actcggacgg agcggatgac accttcgcag cctacacgcg
ggagcagctg taccaggcca tcttccatgc tgtggaccag tacctggcgt tgcctgacgt gtcactgggc
cggtatgcgt atgtccgtgg tgggggtgac ccttggacca atggctcagg gcttgctctc tgccagcggt
actaccaccg aggccacgtg gacccggcca acgacacatt tgacattgat ccgatggtgg ttactgactg
catccaggtg gatccccccg agcggccccc tccgcccccc agcgacgatc tcaccctctt ggaaagcagc
tccagttaca agaacctcac gctcaaattc cacaagctgg tcaatgtcac catccacttc cggctgaaga
ccattaacct ccagagcctc atcaataatg agatcccgga ctgctatacc ttcagcgtcc tgatcacgtt
tgacaacaaa gcacacagtg ggcggatccc catcagcctg gagacccagg cccacatcca ggagtgtaag
caccccagtg tcttccagca cggagacaac agcttccggc tcctgtttga cgtggtggtc atcctcacct
gctccctgtc cttcctcctc tgcgcccgct cactccttcg aggcttcctg ctgcagaacg agtttgtggg
gttcatgtgg cggcagcggg gacgggtcat cagcctgtgg gagcggctgg aatttgtcaa tggctggtac
atcctgctcg tcaccagcga tgtgctcacc atctcgggca ccatcatgaa gatcggcatc gaggccaaga
acttggcgag ctacgacgtc tgcagcatcc tcctgggcac ctcgacgctg ctggtgtggg tgggcgtgat
ccgctacctg accttcttcc acaactacaa tatcctcatc gccacactgc gggtggccct gcccagcgtc
atgcgcttct gctgctgcgt ggctgtcatc tacctgggct actgcttctg tggctggatc gtgctggggc
cctatcatgt gaagttccgc tcactctcca tggtgtctga gtgcctgttc tcgctcatca atggggacga
catgtttgtg acgttcgccg ccatgcaggc gcagcagggc cgcagcagcc tggtgtggct cttctcccag
ctctaccttt actccttcat cagcctcttc atctacatgg tgctcagcct cttcatcgcg ctcatcaccg
gcgcctacga caccatcaag catcccggcg gcgcaggcgc agaggagagc gagctgcagg cctacatcgc
acagtgccag gacagcccca cctccggcaa gttccgccgc gggagcggct cggcctgcag ccttctctgc
tgctgcggaa gggacccctc ggaggagcat tcgctgctgg tgaattgatt cgacctgact gccgttggac
cgtaggccct ggactgcaga gacccccgcc cccgaccccg cttatttatt tgtagggttt gcttttaagg
atcggctccc tgtcgcgccc gaggagggcc tggacctttc gtgtcggacc cttgggggcg gggagactgg
gtggggaggg tgttgaataa a
```

GenBank Accession No.: Q68CP4.2, human HGSNAT, which provides the amino acid sequence (SEQ ID NO: 17):

```
MTGARASAAE QRRAGRSGQA RAAERAAGMS GAGRALAALL LAASVLSAAL LAPGGSSGRD AQAAPPRDLD
KKRHAELKMD QALLLIHNEL LWTNLTVYWK SECCYHCLFQ VLVNVPQSPK AGKPSAAAAS VSTQHGSILQ
LNDTLEEKEV CRLEYRFGEF GNYSLLVKNI HNGVSEIACD LAVNEDPVDS NLPVSIAFLI GLAVIIVISF
LRLLLSLDDF NNWISKAISS RETDRLINSE LGSPSRTDPL DGDVQPATWR LSALPPRLRS VDTFRGIALI
LMVFVNYGGG KYWYFKHASW NGLTVADLVF PWFVFIMGSS IFLSMTSILQ RGCSKFRLLG KIAWRSFLLI
CIGIIIVNPN YCLGPLSWDK VRIPGVLQRL GVTYFVVAVL ELLFAKPVPE HCASERSCLS LRDITSSWPQ
WLLILVLEGL WLGLTFLLPV PGCPTGYLGP GGIGDFGKYP NCTGGAAGYI DRLLLGDDHL YQHPSSAVLY
HTEVAYDPEG ILGTINSIVM AFLGVQAGKI LLYYKARTKD ILIRFTAWCC ILGLISVALT KVSENEGFIP
VNKNLWSLSY VTTLSSFAFF ILLVLYPVVD VKGLWTGTPF FYPGMNSILV YVGHEVFENY FPFQWKLKDN
QSHKEHLTQN IVATALWVLI AYILYRKKIF WKI
```

GenBank Accession No.: NM_152419, human HGSNAT mRNA, which provides the nucleic acid sequence (SEQ ID NO: 18):

```
agggcggggc gcagcgggca ggcaagggcg gccgagcggg cggcgggcat gagcggggcg ggcagggcgc
tggccgcgct gctgctggcc gcgtccgtgc tgagcgccgc gctgctggcc cccggcggct cttcggggcg
cgatgcccag gccgcgccgc cacgagactt agacaaaaaa agacatgcag agctgaagat ggatcaggct
ttgctactca tccataatga acttctctgg accaacttga ccgtctactg gaaatctgaa tgctgttatc
actgcttgtt tcaggttctg gtaaacgttc ctcagagtcc aaaagcaggg aagcctagtg ctgcagctgc
ctctgtcagc acccagcacg gatctatcct gcagctgaac gacaccttgg aagagaaaga agtttgtagg
ttggaataca gatttggaga atttggaaac tattctctct tggtaaagaa catccataat ggagttagtg
aaattgcctg tgacctggct gtgaacgagg atccagttga tagtaacctt cctgtgagca ttgcattcct
tattggtctt gctgtcatca ttgtgatatc ctttctgagg ctcttgttga gtttggatga ctttaacaat
tggatttcta aagccataag ttctcgagaa actgatcgcc tcatcaattc tgagctggga tctcccagca
ggacagaccc tctcgatggt gatgttcagc cagcaacgtg gcgtctatct gccctgccgc cccgcctccg
cagcgtggac accttcaggg ggattgctct tatactcatg gtctttgtca attatggagg aggaaaatat
```

-continued

```
tggtacttca aacatgcaag ttggaatggg ctgacagtgg ctgacctcgt gttcccgtgg tttgtattta
ttatgggatc ttccattttt ctatcgatga cttctatact gcaacggggg tgttcaaaat tcagattgct
ggggaagatt gcatggagga gtttcctgtt aatctgcata ggaattatca ttgtgaatcc caattattgc
cttggtccat tgtcttggga caaggtgcgc attcctggtg tgctgcagcg attgggagtg acatactttg
tggttgctgt gttggagctc ctctttgcta aacctgtgcc tgaacattgt gcctcggaga ggagctgcct
ttctcttcga gacatcacgt ccagctggcc ccagtggctg ctcatcctgg tgctggaagg cctgtggctg
ggcttgacat tcctcctgcc agtccctggg tgccctactg gttatcttgg tcctgggggc attggagatt
ttggcaagta tccaaattgc actggaggag ctgcaggcta catcgaccgc ctgctgctgg gagacgatca
cctttaccag cacccatctt ctgctgtact ttaccacacc gaggtggcct atgaccccga gggcatcctg
ggcaccatca actccatcgt gatggccttt ttaggagttc aggcaggaaa aatactattg tattacaagg
ctcggaccaa agacatcctg attcgattca ctgcttggtg ttgtattctt gggctcattt ctgttgctct
gacgaaggtt tctgaaaatg aaggctttat tccagtaaac aaaaatctct ggtccctttc gtatgtcact
acgctcagtt cttttgcctt cttcatcctg ctggtcctgt acccagttgt ggatgtgaag gggctgtgga
caggaacccc attcttttat ccaggaatga attccattct ggtatatgtc ggccacgagg tgtttgagaa
ctacttcccc tttcagtgga agctgaagga caaccagtcc cacaaggagc acctgactca gaacatcgtc
gccactgccc tctgggtgct cattgcctac atcctctata gaaagaagat tttttggaaa atctgatggc
tcccactgag atgtgctgct ggaagactct agtaggcctg cagggaggac tgaagcagcc tttgttaaag
ggaagcattc attaggaaat tgactggctg cgtgtttaca gactctgggg gaagacactg atgtcctcaa
actggttaac tgtgacacgg ctcgccagaa ctctgcctgt ctatttgtga cttacagatt tgaaatgtaa
ttgtcttttt tcctccatct tctgtggaaa tggatgtctt tggaacttca ttccgaggag ataagcttta
actttccaaa agggaattgc catgggtgtt tttcttctgt ggtgagtgaa acaatctgag gtctggttct
tgctgacctt gttgccctgc aaacttcctt tccacgtgta cgcgcacacc aacacgaaat gccatcactc
ctactgcggc tgctatgaag cttactggtt gtgatgtgtt ataatttagt ctgttttttt gattgaatgc
agtttaatgt ttccagaaag ccaaagtaat ttttcttttca gatatgcaag gctttggtgg gtccaaaaaa
tgtctatcac aagccatttt ttccttttcc tctctcgaaa agttaaaata tctatgtgtt attcccaaac
cctcttacct atgtatctgc ctgtctgtcc atcatcttcc ttcctcccta tctctgtgta tctggatggc
agccgctgcc caggggagtg gctgtgggga gggcaggtac tgtctttgcc tgtgggtcca gctgagccat
ccctgctggg tgatgctggg caagaccctt ggcccgtctg ggccttggct tcctcacttg tgaaatgagc
gggaagatga ctctcagttc cttccacctc ttagacatgg tgaggtaaca gacatcaaaa gcttttctga
aatcttcaga agaaatagtt ccattacaga aaactcttca aaataaatag tagtgaaaac ttttaaaaac
tctcattgga gtaagtcttt tcaagatgat cctccacaat ggaggcagcg ttcctacttg tcatcacaca
gctgaagaca ttgtttctta ggtgtgaaat cggggacaaa ggacaaacag agacacacgg cattgttcat
gggaggcatc gtcaccctcc tgggtgttct gtgggaattt cctgtgtgag gaaaacgtgg ccacagggtt
gtgctgtacc caccctcccc cggcgagatg gccctcggcc tgtgccgctg cttccaccct cgccactcca
tggcagcttt tggtctgttt ccggctctgc cctctgccct gaactctcat ccggcttgta cctgcctgct
ggacccctcc acctggaggc cagcccatgt ctcaggccca gccctagcct cttctcctca aattctaagt
gttttctctt taggtttccc tggctttgtg aatggatcat gtgtctctag gtataaacct gacatcatct
ttccacccgg cttacctcca ccagatctcc ccagttctgt ctccatcttc tacctgcagc tgctctgttc
tcatggtcac tgctgcatca ctgagtctgg acccttgtta tcattttcaa actggcctcc ttccctcgtt
ccccacttct taaagtcacc tgtccattgc caccagatta agctttctcc agccagatca cctctctctg
agaaacctcc attgacatgg aaacaccatt gtctggcaca catactcaca tactcacctt cccgtcttga
tccccacaca tctttccagc ctcccctccc actccactcc ctgctctctc ctccacctcc ccatcctctt
gtctcccctc ccctctgaat ccagcccagc ggggcttctc ctgcctccat cacatcacag aagtacctcc
tgcttctggt tttaattaga gccttccccg attacatttt cctctgaatt ttttcctatc tacatttgat
ctgtcatgtt taaacccccct acttctaagg gaacttctct aatctcttat cctcatcccc aaatagtgtt
ttcttcctct gggttcttat aatgttggta tcaatctcac agcatttagt gcttcctgcc tggtgtgaca
gttacctgtg tgcatgtgca atttctaatt tcccacgcta gactgtgagc ttcctaaggc aagaatcatg
ccttgttggt ttctgtattc ctcatggtgc caaacacagt gccttctaca ttgcaggcgc tgaataaaca
tttttaaagc aaaatgatgt ggatttttaa aataaatatt taagtgctgg taagatgagc atgtatccgg
ggtgcccatg aaatgttctt ggggccgtgt ggggacagtc gtcattcctc ctcctgccac cctttttcttt
cagtgagtca ctgtggatgg tcccagctgt gtcatcccaa agttcagcag ggaaagctga gctgggcctc
tccaggtgag ttttctagaa gcatttctca aactgtgggt tacatcaact tgggtgtctt gagctgtaag
gaaggaactc cggagtcagc tgggctacag gggagcttct ctaagtcctg cgggaggcca gacccagcct
gagcttgctg ttagctagcg gaggcagctg ctggtggccc aggtgctcga caccaggcat cccctctcct
cccacgaagg gtgtgccata atccccttca acaggaaatg cttcccagaa gcctctcagc agcctcccct
cctgtcctat cagctagaag cgcctcgctt gtcccaagac cagcagggac agggaactgt ccgagcccgt
ggctgtgtgg aggaaggcga cccccagcac aagattggtt tcctttggga agggaagagg gagtgtgttg
gggtaagggg tagagcagag gaatggtcag gggcaacaa ccgctgacag ctgcaacagg tgcatggcat
ctcacaggga ggcagggagg tgcgagctcc taagtaatgg agcaaaaaaa ttctattctg tagaatgggg
agagaaaatg tgacatttta attttttttt gcatttatat tcctaattcc tacttaaagt gaatatactg
ccgctgtaga tcataaaatg tatcttttcc atggccaaca aggggcatct tttataaatg cataataacc
cagtttgtat caaagggtat cgacttaagt gaaatttcaa catgctgtta ctttttcctt ttaatgtaat
tctgttttcc aaataaatgg gggagacaaa tggaaaaaaa aaaaaaaa
```

GenBank Accession No.: AAB63982.1, human NPC1, which provides the amino acid sequence (SEQ ID NO: 19):

```
MTARGLALGLLLLLLCPAQVFSQSCVWYGECGIAYGDKRYNCEYSGPPKPLPKDGYDLVQELCPGFFFGNVSLCCD
VRQLQTLKDNLQLPLQFLSRCPSCFYNLLNLFCELTCSPRQSQFLNVTATEDYVDPVTNQTKTNVKELQYYVGQSF
ANAMYNACRDVEAPSSNDKALGLLCGKDADACNATNWIEYMFNKDNGQAPFTITPVFSDFPVHGMEPMNNATKGCD
ESVDEVTAPCSCQDCSIVCGPKPQPPPPPAPWTILGLDAMYVIMWITYMAFLLVFFGAFFAVWCYRKRYFVSEYTP
IDSNIAFSVNASDKGEASCCDPVSAAFEGCLRRLFTRWGSFCVRNPGCVIFFSLVFITACSSGLVFVRVTTNPVDL
WSAPSSQARLEKEYFDQHFGPFFRTEQLIIRAPLTDKHIYQPYPSGADVPFGPPLDIQILHQVLDLQIAIENITAS
YDNETVTLQDICLAPLSPYNTNCTILSVLNYFQNSHSVLDHKKGDDFFVYADYHTHFLYCVRAPASLNDTSLLHDP
CLGTFGGPVFPWLVLGGYDDQNYNNATALVITFPVNNYYNDTEKLQRAQAWEKEFINFVKNYKNPNLTISFTAERS
IEDELNRESDSDVFTVVISYAIMFLYISLALGHIKSCRRLLVDSKVSLGIAGILIVLSSVACSLGVFSYIGLPLTL
IVIEVIPFLVLAVGVDNIFILVQAYQRDERLQGETLDQQLGRVLGEVAPSMFLSSFSETVAFFLGALSVMPAVHTF
SLFAGLAVFIDFLLQITCFVSLLGLDIKRQEKNRLDIFCCVRGAEDGTSVQASESCLFRFFKNSYSPLLLKDWMRP
IVIAIFVGVLSFSIAVLNKVDIGLDQSLSMPDDSYMVDYFKSISQYLHAGPPVYFVLEEGHDYTSSKGQNMVCGGM
GCNNDSLVQQIFNAAQLDNYTRIGFAPSSWIDDYFDWVKPQSSCCRVDNITDQFCNASVVDPACVRCRPLTPEGKQ
```

RPQGGDFMRFLPMFLSDNPNPKCGKGGHAAYSSAVNILLGHGTRVGATYFMTYHTVLQTSADFIDALKKARLIASN
VTETMGINGSAYRVFPYSVFYVFYEQYLTIIDDTIFNLGVSLGAIFLVTMVLLGCELWSAVIMCATIAMVLVNMFG
VMWLWGISLNAVSLVNLVMSCGISVEFCSHITRAFTVSMKGSRVERAEEALAHMGSSVFSGITLTKFGGIVVLAFA
KSQIFQIFYFRMYLAMVLLGATHGLIFLPVLLSYIGPSVNKAKSCATEERYKGTERERLLNF

GenBank Accession No.: AF002020.1, human NPC1 mRNA, complete cds, which provides the nucleic acid sequence (SEQ ID NO: 20):

tttgctcctg ctcctccgct cctcctgcgc ggggtgctga aacagcccgg ggaagtagag ccgcctccgg
ggagcccaac cagccgaacg ccgccggcgt cagcagcctt gcgcggccac agcatgaccg ctcgcggcct
ggcccttggc ctcctcctgc tgctactgtg tccagcgcag gtgttttcac agtcctgtgt ttggtatgga
gagtgtggaa ttgcatatgg ggacaagagg tacaattgcg aatattctgg cccaccaaaa ccattgccaa
aggatggata tgacttagtg caggaactct gtccaggatt cttctttggc aatgtcagtc tctgttgtga
tgttcggcag cttcagacac taaaagacaa cctgcagctg cctctacagt ttctgtccag atgtccatcc
tgtttttata acctactgaa cctgttttgt gagctgacat gtagccctcg acagagtcag tttttgaatg
ttacagctac tgaagattat gttgatcctg ttacaaacca gacgaaaaca aatgtgaaag agttacaata
ctacgtcgga cagagttttg ccaatgcaat gtacaatgcc tgccgggatg tggaggcccc ctcaagtaat
gacaaggccc tgggactcct gtgtgggaag gacgctgacg cctgtaatgc caccaactgg attgaataca
tgttcaataa ggacaatgga caggcacctt ttaccatcac tcctgtgttt tcagattttc cagtccatgg
gatggagccc atgaacaatg ccaccaaagg ctgtgacgag tctgtggatg aggtcacagc accatgtagc
tgccaagact gctctattgt ctgtggcccc aagccccagc cccacctcc tcctgctccc tggacgatcc
ttggcttgga cgccatgtat gtcatcatgt ggatcaccta catggcgttt ttgcttgtgt tttttggagc
atttttgca gtgtggtgct acagaaaacg gtattttgtc tccgagtaca ctcccatcga tagcaatata
gctttttctg ttaatgcaag tgacaaagga gaggcgtcct gctgtgaccc tgtcagcgca gcatttgagg
gctgcttgag gcggctgttc acacgctggg ggtctttctg cgtccgaaac cctggctgtg tcattttctt
ctcgctggtc ttcattactg cgtgttcgtc aggcctggtg tttgtccggg tcacaaccaa tccagttgac
ctctggtcag cccccagcag ccaggctcgc ctggaaaaag agtactttga ccagcacttt gggcctttct
tccggacgga gcagctcatc atccgggccc ctctcactga caaacacatt taccagccat acccttcggg
agctgatgta ccctttggac ctccgcttga catacagata ctgcaccagg ttcttgactt acaaatagcc
atcgaaaaca ttactgcctc ttatgacaat gagactgtga cacttcaaga catctgcttg gcccctcttt
caccgtataa cacgaactgc accattttga gtgtgttaaa ttacttccag aacagccatt ccgtgctgga
ccacaagaaa ggggacgact tctttgtgta tgccgattac cacacgcact ttctgtactg cgtacgggct
cctgcctctc tgaatgatac aagtttgctc catgaccctt gtctgggtac gtttggtgga ccagtgttcc
cgtggcttgt gttgggaggc tatgatgatc aaaactacaa taacgccact gcccttgtga ttaccttccc
tgtcaataat tactataatg atacagagaa gctccagagg gcccaggcct gggaaaaaga gtttattaat
tttgtgaaaa actacaagaa tcccaatctg accatttcct tcactgctga acgaagtatt gaagatgaac
taaatcgtga aagtgacagt gatgtcttca ccgttgtaat tagctatgcc atcatgtttc tatatatttc
cctagccttg gggcacatca aaagctgtcg caggcttctg gtggattcga aggtctcact aggcatcgcg
ggcatcttga tcgtgctgag ctcggtggct tgctccttgg gtgtcttcag ctacattggg ttgcccttga
ccctcattgt gattgaagtc atcccgttcc tggtgctggc tgttggagtg gacaacatct tcattctggt
gcaggcctac cagagagatg aacgtcttca aggggaaacc ctggatcagc agctgggcag ggtcctagga
gaagtggctc ccagtatgtt cctgtcatcc ttttctgaga ctgtagcatt tttcttagga gcattgtccg
tgatgccagc cgtgcacacc ttctctctct ttgcgggatt ggcagtcttc attgactttc ttctgcagat
tacctgtttc gtgagtctct tggggttaga cattaaacgt caagagaaaa atcggctaga catcttttgc
tgtgtcagag gtgctgaaga tggaacaagc gtccaggcct cagagagctg tttgtttcgc ttcttcaaaa
actcctattc tccacttctg ctaaaggact ggatgagacc aattgtgata gcaatatttg tgggtgttct
gtcattcagc atcgcagtcc tgaacaaagt agatattgga ttggatcagt ctctttcgat gccagatgac
tcctacatgg tggattattt caaatccatc agtcagtacc tgcatgcggg tccgcctgtg tactttgtcc
tggaggaagg gcacgactac acttcttcca aggggcagaa catggtgtgc ggcggcatgg gctgcaacaa
tgattccctg gtgcagcaga tatttaacgc ggcgcagctg gacaactata cccgaatagg cttcgccccc
tcgtcctgga tcgacgatta tttcgactgg gtgaagccac agtcgtcttg ctgtcgagtg gacaatatca
ctgaccagtt ctgcaatgct tcagtggttg accctgcctg cgttcgctgc aggcctctga ctccggaagg
caaacagagg cctcaggggg gagacttcat gagattcctg cccatgttcc tttcggataa ccctaacccc
aagtgtggca aagggggaca tgctgcctat agttctgcag ttaacatcct ccttggccat ggcaccaggg
tcggagccac gtacttcatg acctaccaca ccgtgctgca gacctctgct gactttattg acgctctgaa
gaaagcccga cttatagcca gtaatgtcac cgaaaccatg ggcattaacg gcagtgccta ccgagtattt
ccttacagtg tgttttatgt cttctacgaa cagtacctga ccatcattga cgacactatc ttcaacctcg
gtgtgtccct gggcgcgata tttctggtga ccatggtcct cctgggctgt gagctctggt ctgcagtcat
catgtgtgcc accatcgcca tggtcttggt caacatgttt ggagttatgt ggctctgggg catcagtctg
aacgctgtat ccttggtcaa cctggtgatg agctgtggca tctccgtgga gttctgcagc cacataacca
gagcgttcac ggtgagcatg aaaggcagcc gcgtggagcg cgcggaagag gcacttgccc acatgggcag
ctccgtgttc agtggaatca cacttacaaa atttggaggg attgtggtgt tggcttttgc caaatctcaa
attttccaga tattctactt caggatgtat ttggccatgg tcttactggg agccactcac ggattaatat
ttctccctgt cttactcagt tacatagggc catcagtaaa taaagccaaa agttgtgcca ctgaagagcg
atacaaagga acagagcgcg aacggcttct aaatttctag ccctctcgca gggcatcctg actgaactgt
gtctaagggt cggtcggttt accactggac gggtgctgca tcggcaaggc caagttgaac accggatggt
gccaaccatc ggttgtttgg cagcagcttt gaacgtagcg cctgtgaact caggaatgca cagttgactt
gggaagcagt attactagat ctggaggcaa ccacaggaca ctaaacttct cccagcctct tcaggaaaga
aacctcattc tttggcaagc aggaggtgac actagatggc tgtgaatgtg atccgctcac tgacactctg
taaaggccaa tcaatgcact gtctgtcctc tcctttttag gagtaagcca tcccacaagt tctataccat
atttttagtg acagttgagg ttgtagatac actttataac attttatagt ttaaagagct ttattaatgc
aataaattaa ctttgtacac atttttatat aaaaaaacag caagtgattt cagaatgttg taggcctcat
tagagcttgg tctccaaaaa tctgtttgaa aaaagcaaca tgttcttcac agtgttcccc tagaaaggaa
gagatttaat tgccagttag atgtggcatg aaatgaggga caaagaaagc atctcgtagg tgtgtctact
gggttttaac ttatttttct ttaataaaat acattgtttt cctaaaaaaa aaa GenBank Accession No.: CAA54416.1, human LAMP-2A, which provides the amino acid sequence (SEQ ID NO: 21):

MVCFRLFPVP GSGLVLVCLV LGAVRSYALE LNLTDSENAT CLYAKWQMNF TVRYETTNKT YKTVTISDHG
TVTYNGSICG DDQNGPKIAV QFGPGFSWIA NFTKAASTYS IDSVSFSYNT GDNTTFPDAE DKGILTVDEL

-continued

LAIRIPLNDL FRCNSLSTLE KNDVVQHYWD VLVQAFVQNG TVSTNEFLCD KDKTSTVAPT IHTTVPSPTT
TPTPKEKPEA GTYSVNNGND TCLLATMGLQ LNITQDKVAS VININPNTTH STGSCRSHTA LLRLNSSTIK
YLDFVFAVKN ENRFYLKEVN ISMYLVNGSV FSIANNNLSY WDAPLGSSYM CNKEQTVSVS GAFQINTFDL
RVQPFNVTQG KYSTAQDCSA DDDNFLVPIA VGAALAGVLI LVLLAYFIGL KHHHAGYEQF

GenBank Accession No.: X77196.1, human LAMP2 mRNA, which provides the nucleic acid sequence (SEQ ID NO: 22):

ccgattcctg gcttttgcaa ggctgtggtc ggtggtcatc agtgctcttg acccaggtcc agcgagcctt
ttccctggtg ttgcagctgt tgttgtaccg ccgccgtcgc cgccgtcgcc gcctgctctg cggggtcatg
gtgtgcttcc gcctcttccc ggttccgggc tcagggctcg ttctggtctg cctagtcctg ggagctgtgc
ggtcttatgc attggaactt aatttgacag attcagaaaa tgccacttgc ctttatgcaa aatggcagat
gaatttcaca gtacgctatg aaactacaaa taaaacttat aaaactgtaa ccatttcaga ccatggcact
gtgacatata atggaagcat ttgtggggat gatcagaatg gtcccaaaat agcagtgcag ttcggacctg
gcttttcctg gattgcgaat tttaccaagg cagcatctac ttattcaatt gacagcgtct cattttccta
caacactggt gataacacaa catttcctga tgctgaagat aaaggaattc ttactgttga tgaacttttg
gccatcagaa ttccattgaa tgaccttttt agatgcaata gtttatcaac tttggaaaag aatgatgttg
tccaacacta ctgggatgtt cttgtacaag cttttgtcca aaatggcaca gtgagcacaa atgagttcct
gtgtgataaa gacaaaactt caacagtggc acccaccata cacaccactg tgccatctcc tactacaaca
cctactccaa aggaaaaacc agaagctgga acctattcag ttaataatgg caatgatact tgtctgctgg
ctaccatggg gctgcagctg aacatcactc aggataaggt tgcttcagtt attaacatca accccaatac
aactcactcc acaggcagct gccgttctca cactgctcta cttagactca atagcagcac cattaagtat
ctagactttg tctttgctgt gaaaaatgaa aaccgatttt atctgaagga agtgaacatc agcatgtatt
tggttaatgg ctccgttttc agcattgcaa ataacaatct cagctactgg gatgcccccc tgggaagttc
ttatatgtgc aacaaagagc agactgtttc agtgtctgga gcatttcaga taaatacctt tgatctaagg
gttcagcctt tcaatgtgac acaaggaaag tattctacag ctcaagactg cagtgcagat gacgacaact
tccttgtgcc catagcggtg ggagctgcct tggcaggagt acttattcta gtgttgctgg cttattttat
tggtctcaag caccatcatg ctggatatga gcaattttag aatctgcaac ctgattgatt atataaaaat
acatgcaaat aacaagattt tcttacctct cagttgttga aacactttgc ttcttaaaat tgatatgttg
aaactttaat tcttttatca atcccagcat tttgagatca gtctttatta ataaaacctg ttctctttaa
tcagcttaaa atccaaagtg tcatatttac tggtcctgga gacaaacttg ttcaaaagaa catcaacgtg
caatgtttta aggtctatct taagaagccc tggccaaatt ttgatcctaa ccttgaagta tgccttgaac
ttattaacat ggccattata agaataaaat atgtagttgt gtcttaatgg aattaataaa tgtcatttca
ctactggtgt tctgtttca atgtataagg actatagtga tttaaactca tcaatgtgcc tttgcataaa
gttgattaaa taaatattga tgtggtataa atgcccatca gatatgct GenBank Accession No.: AAA91149.1, human LAMP-2B, which provides the amino acid sequence (SEQ ID NO: 23):

MVCFRLFPVPGSGLVLVCLVLGAVRSYALELNLTDSENATCLYAKWQMNFTVRYETTNKTYKTVTISDHGTVTYNG
SICGDDQNGPKIAVQFGPGFSWIANFTKAASTYSIDSVSFSYNTGDNTTFPDAEDKGILTVDELLAIRIPLNDLFR
CNSLSTLEKNDVVQHYWDVLVQAFVQNGTVSTNEFLCDKDKTSTVAPTIHTTVPSPTTTPTPKEKPEAGTYSVNNG
NDTCLLATMGLQLNITQDKVASVININPNTTHSTGSCRSHTALLRLNSSTIKYLDFVFAVKNENRFYLKEVNISMY
LVNGSVFSIANNNLSYWDAPLGSSYMCNKEQTVSVSGAFQINTFDLRVQPFNVTQGKYSTAQECSLDDDTILIPII
VGAGLSGLIIVIVIAYVIGRRKSYAGYQTL

GenBank Accession No.: U36336.1, human LAMP-2B mRNA, complete cds, which provides the nucleic acid sequence (SEQ ID NO: 24):

ccgattcctg gcttttgcaa ggctgtggtc ggtggtcatc agtgctcttg acccaggtcc agcgagcctt
ttccctggtg ttgcagctgt tgttgtaccg ccgccgtcgc cgccgtcgcc gcctgctctg cggggtcatg
gtgtgcttcc gcctcttccc ggttccgggc tcagggctcg ttctggtctg cctagtcctg ggagctgtgc
ggtcttatgc attggaactt aatttgacag attcagaaaa tgccacttgc ctttatgcaa aatggcagat
gaatttcaca gtacgctatg aaactacaaa taaaacttat aaaactgtaa ccatttcaga ccatggcact
gtgacatata atggaagcat ttgtggggat gatcagaatg gtcccaaaat agcagtgcag ttcggacctg
gcttttcctg gattgcgaat tttaccaagg cagcatctac ttattcaatt gacagcgtct cattttccta
caacactggt gataacacaa catttcctga tgctgaagat aaaggaattc ttactgttga tgaacttttg
gccatcagaa ttccattgaa tgaccttttt agatgcaata gtttatcaac tttggaaaag aatgatgttg
tccaacacta ctgggatgtt cttgtacaag cttttgtcca aaatggcaca gtgagcacaa atgagttcct
gtgtgataaa gacaaaactt caacagtggc acccaccata cacaccactg tgccatctcc tactacaaca
cctactccaa aggaaaaacc agaagctgga acctattcag ttaataatgg caatgatact tgtctgctgg
ctaccatggg gctgcagctg aacatcactc aggataaggt tgcttcagtt attaacatca accccaatac
aactcactcc acaggcagct gccgttctca cactgctcta cttagactca atagcagcac cattaagtat
ctagactttg tctttgctgt gaaaaatgaa aaccgatttt atctgaagga agtgaacatc agcatgtatt
tggttaatgg ctccgttttc agcattgcaa ataacaatct cagctactgg gatgcccccc tgggaagttc
ttatatgtgc aacaaagagc agactgtttc agtgtctgga gcatttcaga taaatacctt tgatctaagg
gttcagcctt tcaatgtgac acaaggaaag tattctacag cccaagagtg ttcgctggat gatgacacca
ttctaatccc aattatagtt ggtgctggtc tttcaggctt gattatcgtt atagtgattg cttacgtaat
tggcagaaga aaaagttatg ctggatatca gactctgtaa cactaatcaa tacgtgatct ctgttacaaa
agaaaaaagc aagtacaagt tccaacatgc aatactggtc aacttaaggt atatttagtt gcagtccagc
tctttagaat gggtggtatg gggatttca aacttaaaca aaaaactatc aactacaaat tagttgcctg
actttggttt ttccaaccaa ggaatttaaa actgttattt ttacagcaaa agatgtgcaa aatcactgga
ttataagttc tattttactg tcttgaatta gtatttcagt gttttcattt tagacattca gactaaaaat
acaccgttta gaaaaaacaa tttttgaaaa agagattttt tttccctgca ggtagttgag ttgaacaaca
tgttctaccg tggatttgta cttgctcctt ttgctctttt tgtgtgtgtg tgtgtgtgtg tgtgtgtgtg
tgtgattttt gtttgcaggt taacttagct actttggcat tgctgcatat ttgacctttg agagatataa
tagtagattt gaacaggggc tggtattatt atgttcttag caataaatgc ttttctaatg ccttttgaat
acatttgtat ttatgtggct gtaatgacaa aagatacaaa agctttttaa aatttagagt aggtattaat
cttattgttt aatctttttt ttaaaaaaac tggatatttc aatcttttaa attgcaatat ataagactat
tccaactggg catttcaatc catttttag gtgctttaga gataattgct tgccagtgcc aattgagggc
attagtactt tgtgctcata aattggcctc tgtatgcagt actaaaatta atgcagattt ctctttagcc
ttccaacatt tcttgttgat agtgatgtat tttattattt tctttttctt aagaaatgcc agtgtgtcct -continued

```
agaacctaga taacgaagtg cacttacact tataaaataa cttgcatcta ggctgggcgt ggcggctcac
gcctgtaatc ccagcacttt gggaggccga agtgggtgga tcacttgagg ccaggagttt gagaccagcc
tggccaacat ggtgaaaccc catctctatc agaaatacaa aaaattagct gggcatggtg gtgggcgcct
gtaatcccag ttactcggga ggctgaggca ggagaatcac ttgaacccgg gaggcagagg ttgcggtgag
ccaagagcgc accattgcac tccagccttg ggcgacaaaa acgaaactcc atcttcaaaa caaaacaaaa
caaaacaaac aaacaaacaa aacttgcatc ttaaccaaaa gtcttggttt tatcttaatc cattaaaagt
tggtcttgtt tccagcttgc attgattgct acaacatcac taatttggct ttcacattta aatggttctg
tgctaatcaa aactttcgtt gttattattc gttatggtag aatcattttt aattcacgtg ctttgtgttc
agttttgtgg tctgagagat gtaccaattg tcaaattacc gtgtaccacc taatgtttat aggagaaagc
aaaatacatc agcttggtag ttaacacatc aaatatttct tgctgcttct aggagaactt ttttggtgtg
tgttggaatg gctgagcaaa tattaaaatt gttaatatgc agccatatat ggaaggttcc tgtggggttg
tttttcgtg tttttttttt ttgtggtggg attatgtgcc tcccattcac tagaaaatga gaaaattgtc
tgggttccaa aatattgaca ttgaatggat caatacacac acacagacat atatatatat atatgcacac
atatataggc agttgcatgc ctagcatggg tattttataa ccatataact gagttatatt ggaattataa
atattttccg tcacttaaat ttgttctttg tttagcctga aaacctttat ggctcaagat cagattcctg
actaacccct ctcttagagc tacagcgagc tgcattacca gcttaaaaca cttcttaggg attaaatata
gatgtaattt ttcaaaatcg tttttaattt aaactgtgtt ttagtgtaaa attgttaacc ttgtaagatg
gataatgtgt ataagaatgt aggccttaac tatttcacat gagtcaaaac aaagcagctt taaaaaaata
attggaagca caatgcatgg cactgactga atgctgttaa tatttctaaa agtttctaca ttcagattat
atgcctgatt catagtaaaa tacctctaat aaacactgtt ttatagaaaa cctgacttca gtgaatattt
ttgtatttta catgggccag tttatatact gctatttaca ctattatttc ctatagctac atgttctttg
taccttttgt agttttattt gtattactag attcatacct tgatggtaac gctctatctg gttttgggtg
tttttcatgt tttagcattt gtataaagaa actggtccat gtaaatactt tccatgtttt ttcttcaaat
gtttaaacca ctagttgatg tatggtatct ttagatattt gcctgtctgt ttgctcaaaa ttgcttctaa
aacaataaag attctt
```

GenBank Accession No.: AAS67876.1, human LAMP-2C, which provides the amino acid sequence (SEQ ID NO: 25):

```
MVCFRLFPVPGSGLVLVCLVLGAVRSYALELNLTDSENATCLYAKWQMNFTVRYETTNKTYKTVTISDHGTVTYNG
SICGDDQNGPKIAVQFGPGFSWIANFTKAASTYSIDSVSFSYNTGDNTTFPDAEDKGILTVDELLAIRIPLNDLFR
CNSLSTLEKNDVVQHYWDVLVQAFVQNGTVSTNEFLCDKDKTSTVAPTIHTTVPSPTTTPTPKEKPEAGTYSVNNG
NDTCLLATMGLQLNITQDKVASVININPNTTHSTGSCRSHTALLRLNSSTIKYLDFVFAVKNENRFYLKEVNISMY
LVNGSVFSIANNNLSYWDAPLGSSYMCNKEQTVSVSGAFQINTFDLRVQPFNVTQGKYSTAEECSADSDLNFLIPV
AVGVALGFLIIVVFISYMIGRRKSRTGYQSV
```

GenBank Accession No.: AY561849.1, human LAMP-2C mRNA, complete cds, which provides the nucleic acid sequence (SEQ ID NO: 26):

```
atggtgtgct tccgcctctt cccggttccg ggctcagggc tcgttctggt ctgcctagtc ctgggagctg
tgcggtctta tgcattggaa cttaatttga cagattcaga aaatgccact tgcctttatg caaaatggca
gatgaatttc acagtacgct atgaaactac aaataaaact tataaaactg taaccatttc agaccatggc
actgtgacat ataatggaag catttgtggg gatgatcaga atggtcccaa aatagcagtg cagttcggac
ctggcttttc ctggattgcg aattttacca aggcagcatc tacttattca attgacagcg tctcattttc
ctacaacact ggtgataaca caacatttcc tgatgctgaa gataaaggaa ttcttactgt tgatgaactt
ttggccatca gaattccatt gaatgacctt tttagatgca atagtttatc aactttggaa aagaatgatg
ttgtccaaca ctactgggat gttcttgtac aagcttttgt ccaaaatggc acagtgagca caaatgagtt
cctgtgtgat aaagacaaaa cttcaacagt ggcacccacc atacacacca ctgtgccatc tcctactaca
acacctactc caaaggaaaa accagaagct ggaacctatt cagttaataa tggcaatgat acttgtctgc
tggctaccat ggggctgcag ctgaacatca ctcaggataa ggttgcttca gttattaaca tcaaccccaa
tacaactcac tccacaggca gctgccgttc tcacactgct ctacttagac tcaatagcag caccattaag
tatctagact ttgtctttgc tgtgaaaaat gaaaaccgat tttatctgaa ggaagtgaac atcagcatgt
atttggttaa tggctccgtt ttcagcattg caaataacaa tctcagctac tgggatgccc ccctgggaag
ttcttatatg tgcaacaaag agcagactgt ttcagtgtct ggagcatttc agataaatac ctttgatcta
agggttcagc ctttcaatgt gacacaagga aagtattcta cagctgaaga atgttctgct gactctgacc
tcaactttct tattcctgtt gcagtgggtg tggccttggg cttccttata attgttgtct ttatctctta
tatgattgga agaaggaaaa gtcgtactgg ttatcagtct gtgtaa
```

In another aspect, the method of treating lysosomal transmembrane protein disease or disorder in a subject includes contacting cells expressing a protein associated with the particular disease or disorder (see Table 1) from the subject with a vector encoding a gene editing system that when transfected into the cells removes a mutation (e.g., a tri-nucleotide repeat expansion mutation) of the endogenous protein, thereby treating the lysosomal transmembrane protein disease or disorder. In various embodiments, the gene editing system is selected from the group consisting of CRISPR/Cas, zinc finger nucleases, and transcription activator-life effector nucleases. The step of contacting may be performed ex vivo by first obtaining a sample of cells from the subject, transfecting the gene editing system into the sample of cells, and thereafter transplanting the transfected cells into the subject, thereby treating the lysosomal transmembrane protein disease or disorder. The sample of cells may be any cells expressing the protein associated with the lysosomal transmembrane protein disease or disorder, such as, for example, blood cells or HSPCs of the subject.

In another aspect, the present invention provides a method of treating or ameliorating a lysosomal protein disease or disorder in a subject. The method includes transplanting a population of HSPCs into the subject, wherein the HSPCs have been genetically modified by introduction of a transgene encoding a corresponding functional human lysosomal transmembrane protein, thereby treating the lysosomal transmembrane protein disease or disorder. Thus, when the lysosomal transmembrane protein disease or disorder is cystinosis, the functional human lysosomal transmembrane gene is CTNS; the lysosomal transmembrane protein disease or disorder is Salla disease or infantile sialic acid storage disorder, the functional human lysosomal transmembrane gene is SLC17A5; the lysosomal transmembrane protein disease or disorder is Cobalamin F-type disease, the functional human lysosomal transmembrane gene is LMBRD1;

the lysosomal transmembrane protein disease or disorder is late infantile neuronal ceroid lipofuscinosis, the functional human lysosomal transmembrane gene is MFSD8; the lysosomal transmembrane protein disease or disorder is juvenile neuronal ceroid lipofuscinosis, the functional human lysosomal transmembrane gene is CLN3; the lysosomal transmembrane protein disease or disorder is malignant infantile osteopoetrosis, the functional human lysosomal transmembrane gene is CLCN7 or OSTM1; the lysosomal transmembrane protein disease or disorder is mucolipidosis IV, the functional human lysosomal transmembrane gene is MCOLN1; the lysosomal transmembrane protein disease or disorder is mucopolysaccharidosis type IIIC, the functional human lysosomal transmembrane gene is HGSNAT; the lysosomal transmembrane protein disease or disorder is Neiman-Pick Type C, the functional human lysosomal transmembrane gene is NPC1; and the lysosomal transmembrane protein disease or disorder is Danon disease, the functional human lysosomal transmembrane gene is LAMP2. In various embodiments, the HSPCs are isolated from the subject, such as from the bone marrow of the subject.

While the present invention has been demonstrated with regard to cystinosis and Danon disease, it should be understood that the methods are applicable to any of the diseases or disorders set forth in Table 1. Thus, this strategy turns HSPCs into intelligent and widespread delivery vehicles to obtain stable and sustained cross-correction after their differentiation into monocytes that enter the circulation and subsequently invade the peripheral tissues where they transform into tissue resident macrophages. These macrophages, through a variety of mechanisms including, but not limited to, the formation of tunneling nanotubes, vesicular release, and direct cell-cell adhesion, transfer their lysosomes, which carry the respective protein to diseased peripheral cells. As such, this work demonstrates the development of a HSPC gene therapy strategy for treating lysosomal transmembrane protein diseases or disorders.

The following examples are intended to illustrate but not limit the invention.

EXAMPLE 1

Preclinical Model of Cystinosis for Testing Therapeutic Approaches

Stem cell therapeutic approaches have been tested on the mouse model of cystinosis, the $Ctns^{-/-}$ mice. This murine model was engineered to produce defective cystinosin, and is thus unable to properly transport cystine out of the lysosomes. The defect results in accumulation of cystine and formation of cystine crystals, pathognomonic of cystinosis. Cystine accumulation is present from birth and increases with age. The original $Ctns^{-/-}$ mice have been backcrossed to generate a pure strain of C57BL/6 $Ctns^{-/-}$ mice, which develop renal dysfunction from 6-months of age, as observed biochemically (elevated serum urea and creatinine) and histologically, and these mice are in end stage renal failure by 18 months. Renal Fanconi syndrome also starts around 6 months old (polyuria, phosphaturia and proteinuria), proximal tubular cells appear de-differentiated, and exhibit the typical "swan-neck" deformity found in mice and humans with cystinosis resulting in atubular glomeruli. Finally, heavy infiltration of inflammatory cells can be observed in the kidney of the $Ctns^{-/-}$ mice. $Ctns^{-/-}$ mice also develop ocular defects with corneal cystine crystal depositions and thyroid dysfunction similar to those observed in affected patients.

EXAMPLE 2

Impact of BMC, HSC and MSC Transplantation on Cystinosis

To determine the appropriate cell population for transplantation in the context of cystinosis, syngeneic bone marrow cell (BMC), $Sca1^{+}$ hematopoietic stem cell (HSC) and mesenchymal stem cell (MSC) transplantations were performed in 2 month-old irradiated $Ctns^{-/-}$ mice. The cells were isolated from either green fluorescent protein (GFP)-transgenic wild-type (WT) mice or from $Ctns^{-/-}$ mice as controls. Analyses of disease parameters were performed 4 months post-transplantation. MSCs had only a short-term limited beneficial impact on the disease. In contrast, tissue cystine content was significantly reduced in all organs tested in the WT BMC and HSC-treated mice (from 57% to 94% decrease depending on tissues). Abundant $GFP^{+}$ bone marrow-derived cells were present in all organs and kidney function was improved. This was the first proof of concept that HSCs could rescue cystinosis even if cystinosin is a transmembrane lysosomal protein as opposed to a secreted enzyme.

EXAMPLE 3

Long-Term Effect of HSC Transplantation in $Ctns^{-/-}$ Mice

It was then determined if this treatment was stable for the life of the mice and could result in multi-organ preservation.

Figures 1, 9A:
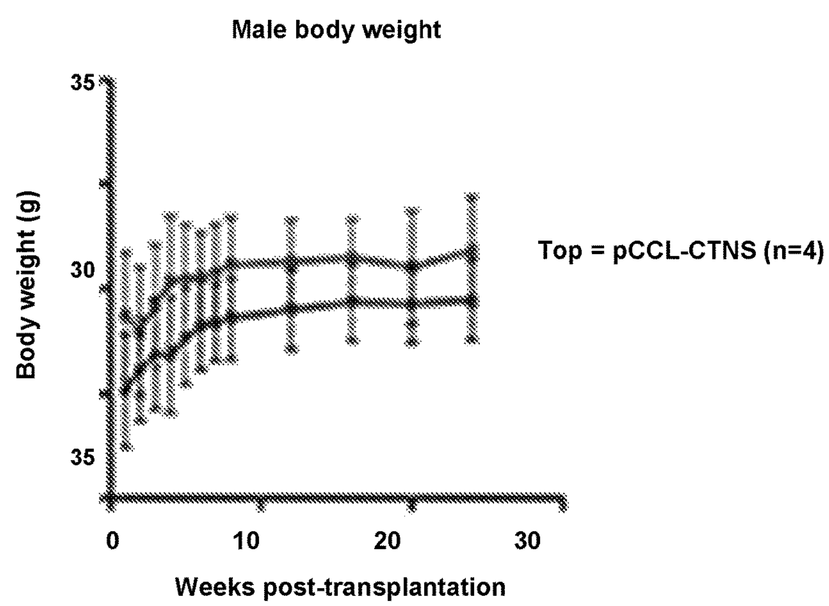

Kidney analysis: Transplantation of WT HSCs was able to provide long-term protection of the kidney function and structure and prevented the progression of the renal disease up to 15 months post-transplantation (last time point tested; FIG. 1). However, effective therapy depends on achieving a relatively high level of donor-derived blood cell engraftment of Ctns-expressing cells (>50%), which is directly linked to the quantity of Ctns-expressing cells found within the kidney. In contrast, kidney preservation was not dependent on the age of the mice at the time of transplant. Indeed, up to 10-month-old mice could exhibit normal kidney function after stem cell treatment, suggesting that if tissue injury is not consolidated, kidney could be rescued. It was also shown that cystine content was significantly decreased in all tissues (from 54% in the kidney to 96.5% in the liver) proving that the treatment, consisting in a one-time HSC transplantation, led to long-term and stably low levels of tissue cystine for the life span of the mice. Moreover, few to no cystine crystals were observed in all kidneys from treated mice whereas abundant cystine crystals were consistently observed in kidneys from non-treated $Ctns^{-/-}$ mice.

Figures 2, 9A:
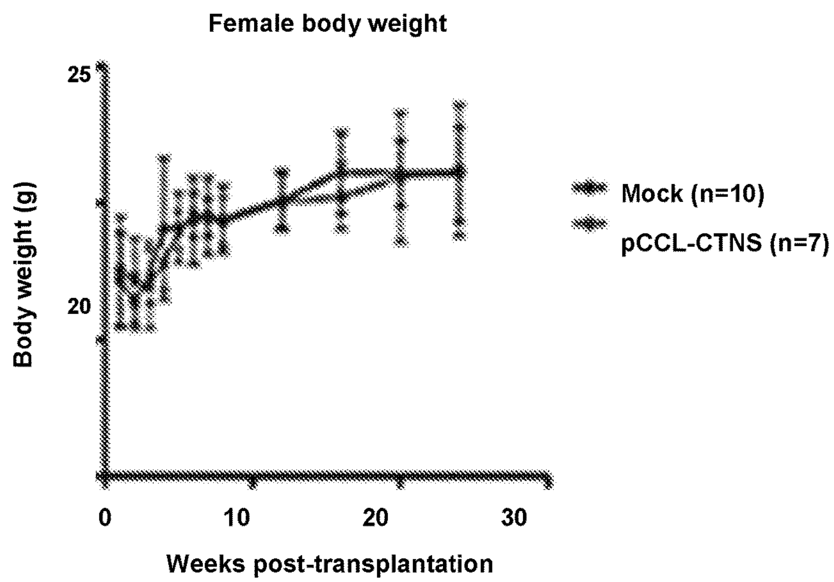

Eye analysis: $GFP^{+}$ WT HSC transplantation led to the long-term preservation of the eyes in $Ctns^{-/-}$ mice. Abundant GFP+ bone marrow-derived cells were detected within the cornea but also in the sclera, ciliary body, retina, choroid, and lens in the treated mice. To quantify cystine crystals within the cornea, in vivo confocal microscopy (IVCM) in live mice was performed. Effective therapy was dependent dependent on the level of donor-derived blood cell engraftment as previously demonstrated for the kidney. While $Ctns^{-/-}$ mice with low level of engraftment (<50%; LOW; n=5) presented a partial reduction of crystal counts, the mice with high engraftment levels (>50%; HIGH; n=5) exhibited almost a complete resolution of crystals from the epithelial layer to the middle stroma (100% to 72% clearance, respectively; FIG. 2). One-year post-transplantation, HSC-treated Ctns$^{-/-}$ mice exhibited normal corneal thickness and structure and normal intraocular pressure. This work was the first demonstration that transplanted HSCs could rescue corneal defects and brings new perspectives for ocular regenerative medicine.

Figure 3:
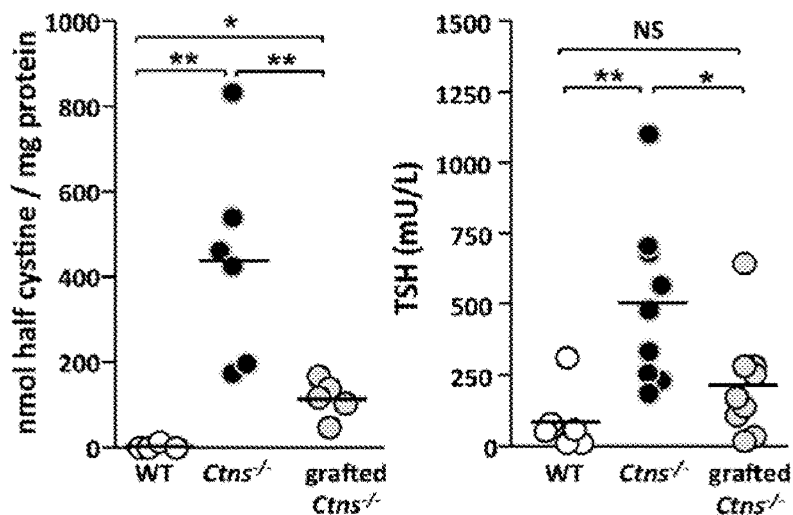
FIG. 3 is a graphical diagram showing the results of a Thyroid study. Measure of cystine content (Left panel) and TSH level (Right panel) in $Ctns^{-/-}$ mice compared to wild-type mice (WT) and $Ctns^{-/-}$ mice transplanted with Ctns-expressing HSCs (grafted $Ctns^{-/-}$).

Thyroid analysis: Since the thyroid gland is also affected in cystinosis, thyroid function and structure from Ctns$^{-/-}$ mice and HSC-transplanted mice were analyzed. Sustained thyroid stimulating hormone (TSH) activation combined with morphological evidence for increased thyroglobulin synthesis was shown in Ctns$^{-/-}$ mice. Follicular changes included thyrocyte hypertrophy, hyperplasia, colloid exhaustion and vascular proliferation. In contrast, Ctns$^{-/-}$ mice treated by HSC transplantation presented virtually normal histology and normalization of cystine and TSH values (FIG. 3).

Figure 4:
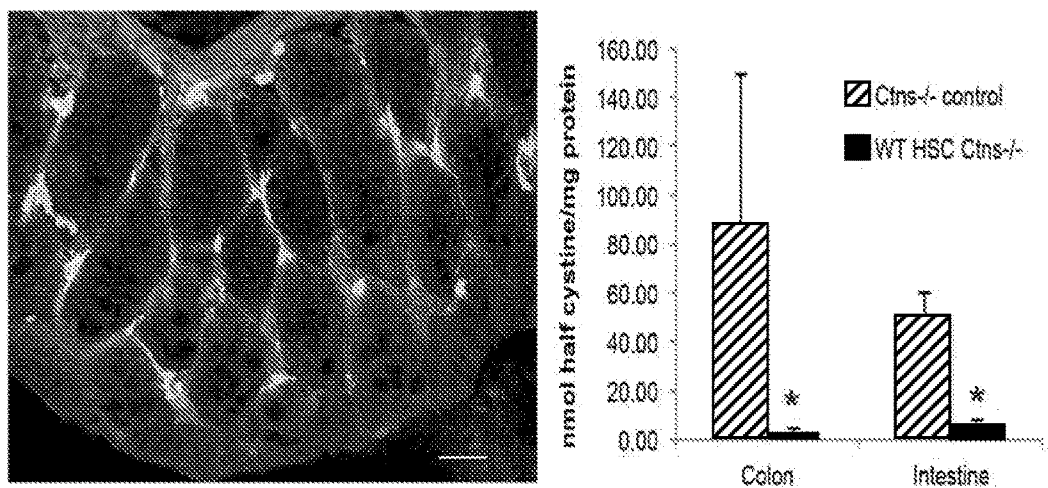
FIG. 4 is a pictorial and graphical diagram showing the impact of HSC transplantation on gastrointestinal tract in $Ctns^{-/-}$ mice. Left panel: Representative confocal picture of the colon: abundant GFP-expressing HSC-derived cells can be seen. Right panel: Cystine content in colon and intestine in HSC-transplanted $Ctns^{-/-}$ mice compared to controls. *$p<0.05$.

Gastro-intestinal tract analysis: Gastrointestinal mucosal biopsies can be used to measure gene-modified stem cell tissue engraftment and their impact on cystine and cystine crystal levels in subjects enrolled in the HSC gene therapy clinical trial for cystinosis. It has been previously described that an histologic technique for evaluating tissue cystine crystal levels on intestinal mucosal biopsies. It was shown that cystine crystal counts could be correlated with renal function and could help evaluating the response to cysteamine treatment. Thus, a rectal biopsy is planned before and every 6 months after gene-corrected HSC transplantation in the subjects with cystinosis. Up to 9 biopsies can be obtained at a time so it is possible to measure Vector Copy number (VCN), CTNS expression, cystine content and cystine crystals in this tissue at each time point. To establish if this tissue is representative of the efficacy of the treatment, the impact of GFP+ WT HSC transplantation on the gastrointestinal tract in Ctns$^{-/-}$ mice was studied. Six months posttransplant, abundant GFP+ HSC-derived cells were observed in both intestine and colon tissues and cystine content was significantly decreased in treated mice compared to controls in these compartments (FIG. 4).

Skin analysis: In vivo confocal microscopy is used on the skin as a noninvasive imaging technology for the visualization and quantification of tissue cystine crystals before and after HSC transplantation in the subjects with cystinosis enrolled in the clinical trial. Chiaverini et al. (Journal of the American Academy of Dermatology 68, e111 (2013)) showed that this technology was able to detect dermal cystine deposition in patients with cystinosis. For this purpose, a reflectance confocal imager (Caliber VIVASCOPE® 3000) adapted for skin imaging was used to test patients with cystinosis. It was also shown in the HSC-transplanted Ctns$^{-/-}$ mice that abundant GFP+ bone marrow-derived cells engrafted within the skin leading to significant cystine decrease in this tissue (79±0.87 in HSC-treated Ctns$^{-/-}$ vs 193±78 in controls, $p<0.05$).

EXAMPLE 4

Myeloablative Conditioning Regimen: Efficacy and Toxicity in Ctns$^{-/-}$ Mice Ctns$^{-/-}$ mice were exposed to myeloablative drugs currently used in clinic for HSC transplantation, Busulfan (Bu) and Cyclophosphamide (Cy) to test if drug-mediated myeloablation allow efficient engraftment of Ctns-expressing HSC in the preclinical model, decreased tissue cystine and to determine if any unexpected toxicity occurs because of cystinosis. Drugs were injected intraperitoneally (IP) in Ctns$^{-/-}$ mice and WT mice as controls. The mice were analyzed at 4 months post-transplant, demonstrating that: i) Ctns$^{-/-}$ mice did not present any toxicity to Bu or Cy compared to WT controls; ii) Renal function was similar to non-treated age-matched WT controls; iii) Myeloablation was successful in both cases and reached a donor cell engraftment measured in the peripheral blood of 94.2±1.6% for Bu/Cy and 94.0±0.8% for Bu alone; and iv) Treated Ctns$^{-/-}$ mice had a significant decrease of cystine in all tissues tested compared to non-treated. Thus, Bu and Cy are not toxic in the mouse model for cystinosis and drug-mediated myeloablation and HSC transplantation in Ctns$^{-/-}$ mice led to significant decrease of cystine in all tissues.

The dosing for myeloablation can be done using busulfan alone without cyclophosphamide. Cyclophosphamide does not ablate the hematopoietic stem cells (i.e., does not make engraftment space), and is immune suppressive and anti-leukemic. Since the HSC transplant is autologous, and not for leukemia, cyclophosphamide is not needed, as it adds unnecessary toxicity to the conditioning regimen. Moreover, it is unusual for severe nephrotoxicity to arise directly due to commonly used-conditioning regimen agents such as busulfan. Note that Dr. Donald Kohn's sickle cell trial (ClinicalTrials.gov Identifier: NCT02247843) is only using busulfan, and the sickle cell and thalassemia trials of bluebird bio, Inc. (ClinicalTrials.gov Identifier: NCT02151526) are also using busulfan without cyclophosphamide.

EXAMPLE 5

Mechanism of Therapeutic Action

The extent of efficacy of HSCs to rescue cystinosis was surprising especially considering that the ability of HSC transplantation to rescue non-hematopoietic tissue remains contentious and that cystinosin is a transmembrane lysosomal protein. To elucidate the mechanism of HSC-mediated tissue repair, a novel mouse model was developed, in which Ctns$^{-/-}$ mice back-crossed on a DsRed background so as to ubiquitously express the DsRed reporter gene (Harrison et al., Mol Ther 21, 433 (2013)). When transplanted with GFP-expressing HSCs derived from GFP-transgenic mice, this generated a bifluorescent mouse mode that not only allowed us to track the fate of the transplanted HSCs in an in vivo setting, but also enabled sensitive identification and unequivocal discrimination of events such as fusion, differentiation, and transdifferentiation.

Figure 5A:
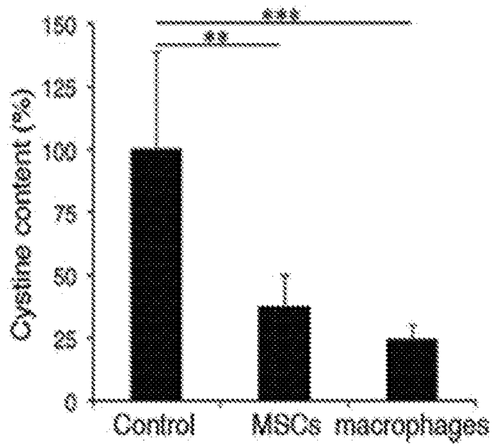
FIGS. 5A-5D are graphical and pictorial diagrams showing TNT-mediated transfer of cystinosin is the preferred mode of cross-correction.
Figure 5B:
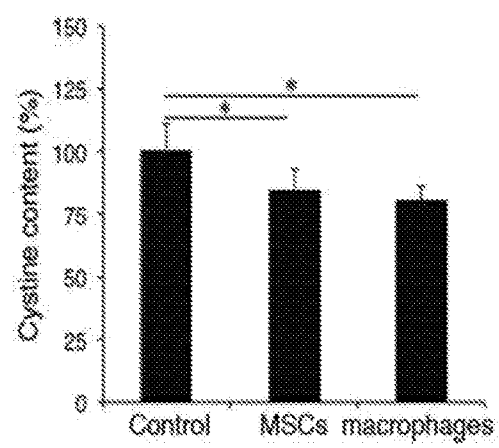
Figure 5C:
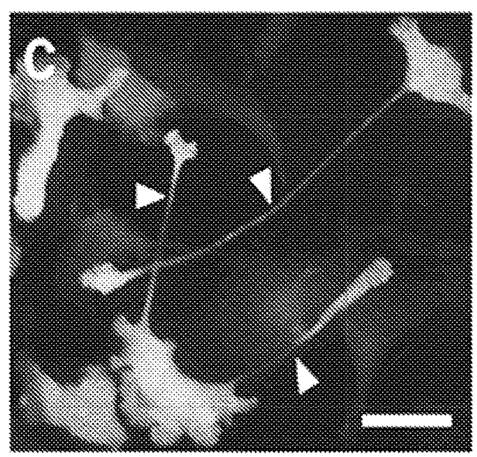
Figure 5D:
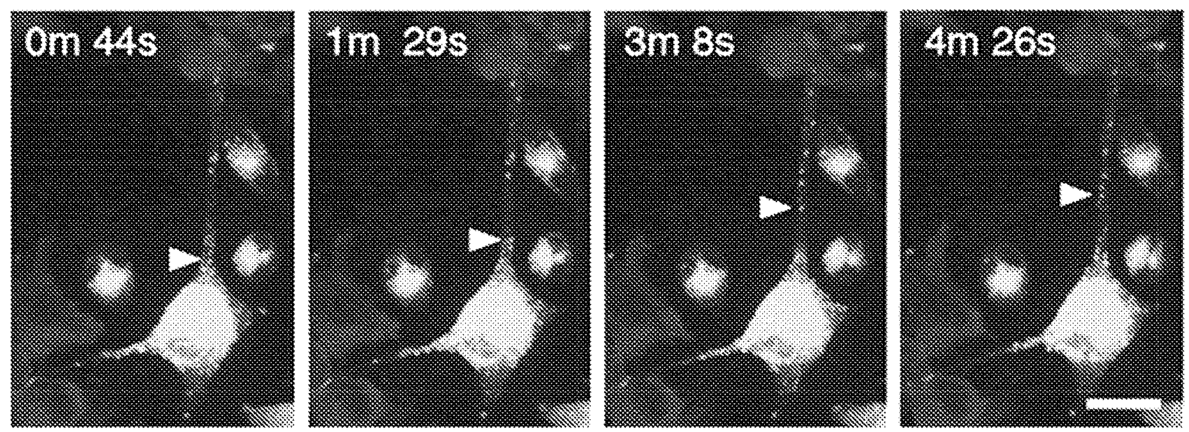

Using this model, it was first shown that HSCs differentiated into macrophages within tissues (Naphade et al., Stem Cells 33, 301 (2015)). In vitro co-culture experiments were then performed using WT GFP-macrophages and DsRed-Ctns$^{-/-}$ fibroblasts. When WT macrophages were co-cultured with Ctns$^{-/-}$ fibroblasts, cystine levels decreased by ~75% in FACS-sorted fibroblasts (FIG. 5A). In contrast, when the two populations were physically separated using a transwell porous to microvesicles, cystine levels decreased only by ~20% (FIG. 5B). These findings showed that cross-correction occurs even if cystinosin is a lysosomal transmembrane protein and that direct cell:cell contact is the main pathway for cross-correction. Using confocal microscopy (FIG. 5C), it was observed that macrophages extended long membrane protrusions called tunneling nanotubes (TNTs) (~40 μm) that established contact with the fibroblasts. To determine whether TNTs could mediate the physical transfer of cystinosin-bearing vesicles, DsRed-$Ctns^{-/-}$ fibroblasts were co-cultured with macrophages stably transduced with a lentivirus vector expressing cystinosin-GFP fusion protein (CTNS-GFP-macrophages). Live confocal microscopy revealed that vesicles containing cystinosin-GFP could migrate along TNTs towards DsRed-$Ctns^{-/-}$ fibroblasts (FIG. 5D). LysoTracker staining identified these vesicles as lysosomes (Naphade et al., Stem Cells 33, 301 (2015)).

Figure 6A:
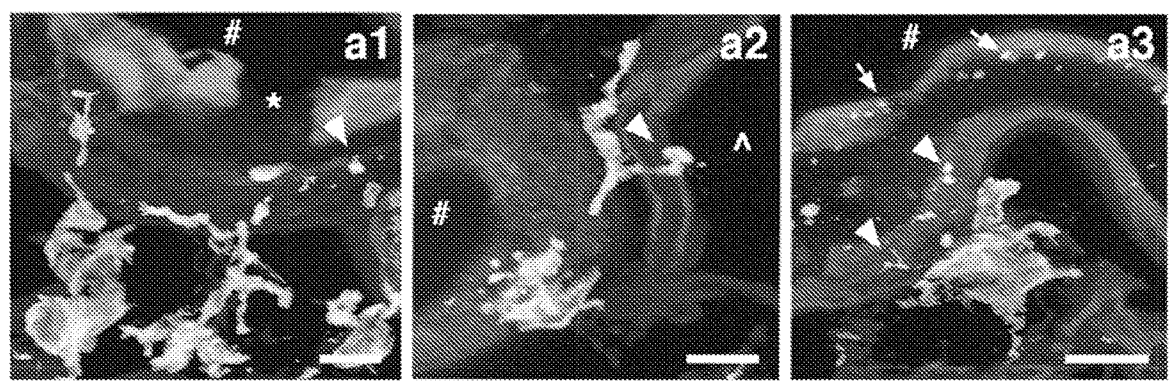
FIGS. 6A-6C are pictorial diagrams showing TNT-mediated transfer in vivo, study of the kidney.
Figure 6B:
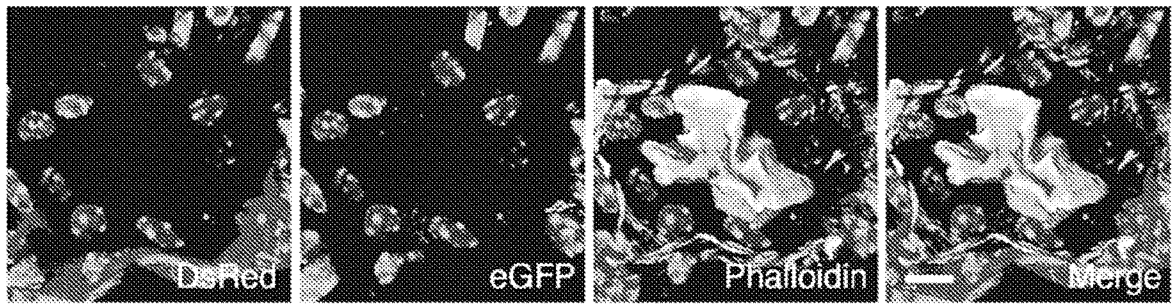
Figure 6C:
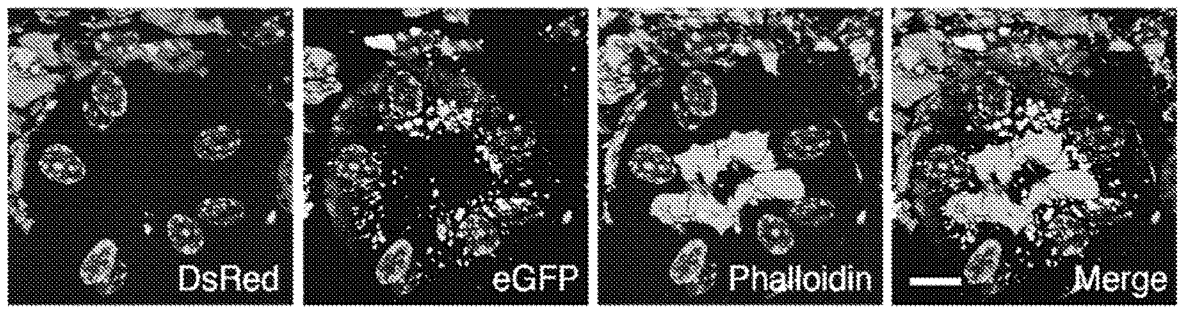

Very little is known about TNTs in vivo. It was thus examined whether intercellular vesicular exchange involving nanotubules could be detected in vivo, so as to account for the long-term kidney preservation in $Ctns^{-/-}$ mice. The initial focus was on the kidney not only because of the early occurrence of cystinosis in proximal tubular cells (PTCs) but also because of their physical isolation by the dense tubular basement lamina (TBL). In the two-color grafted mice, GFP+ bone marrow-derived cells were observed surrounding but never within the proximal tubules and numerous tubular extensions emanated from the HSC-derived macrophages and crossed the TBL (FIGS. 6A-a1 to 6A-a3). GFP-containing structures were observed within PTCs, indicating physical transfer of cytoplasm from the macrophages into the epithelia (FIG. 6A-a3). To test this hypothesis, $Ctns^{-/-}$ mice were transplanted with DsRed-$Ctns^{-/-}$ HSPCs stably expressing cystinosin-GFP fusion protein (FIG. 4C) or with DsRed-$Ctns^{-/-}$ HSPCs (FIG. 4B). Many cystinosin-GFP-vesicles were observed in PTCs (FIG. 4C) (Naphade et al., Stem Cells 33, 301 (2015)). This is the first evidence of direct transfer of proteins from interstitial macrophages to epithelial cells via TNTs penetrating the TBL, so as to correct a genetic defect leading to PTC degeneration. Similar data were obtained for the mechanism of HSC-mediated therapeutic action for the ocular defects (Rocca et al., Investigative ophthalmology & visual science 56, 7214 (2015)) and for the thyroid rescue (Chevronnay et al., Endocrinology In press, (2016)) in the $Ctns^{-/-}$ mice. These findings on HSC-mediated tissue repair bring new perspectives to regenerative medicine, as they should be applicable to other multi-compartment disorders involving deficient intracellular organelles.

EXAMPLE 6

Clinical Study for Hematopoietic Stem Cell Transplantation

The work described above represents the first proof-of-concept for using HSC transplantation as a therapy for cystinosis. To minimize the risks of Graft-versus-host (GVHD), subjects are required to have a sibling bone marrow donor who is HLA-matched on 10 of 10 alleles. This study was designed to include six subjects who are either adults ages 18 years and older with significant signs of disease progression or adolescents ages 13-17 years who do not tolerate cysteamine. However, given the rarity of the disease and strict donor requirements, the candidates so far were not complete matches with their sibling. In addition, the risk-benefit ratio for allogeneic HSC transplantation may not be ideal for young patients where the introduction of regular use of the drug cysteamine has permitted patients to live to adulthood, albeit with significant medical problems (Cherqui, Kidney Int 81, 127 (2012)). Indeed, there are significant risks of morbidity and mortality associated with allogeneic transplantation. GVHD is a major complication; in recent studies, acute GVHD grade II-IV occurred in 20% to 32% of patients and chronic GVHD in 16% to 59%, both significantly impacting survival of the recipients (Cutler et al., Blood 109, 3108 (2007); Geyer et al., Br J Haematol 155, 218 (2011); and Schleuning et al., Bone Marrow Transplant 43, 717 (2009)). Thus, a preferred candidate therapy would utilize the patient's own stem cells for an autologous HSC transplantation, thereby mitigating the risks of graft rejection and GVHD.

EXAMPLE 7

Viral Vector Selection

Given the risks associated with allogeneic HSC transplantation and considering the preclinical data for HSC gene therapy, transplantation of autologous HSC modified to express function cystinosin represents a safer approach.

With regard to gene therapy, vectors derived from lentiviruses have supplanted γ-retroviral vectors due to their superior gene transfer efficiency and improved biosafety profile (Case et al., Proc Natl Acad Sci USA 96, 2988 (1999); Miyoshi, et al. Science 283, 682 (1999); Naldini et al., Science 272, 263 (1996); and Varma et al., Nature 389, 239 (1997)). Specifically:

1. All cases of leukemogenic complications observed to date in clinical trials or animal models of gene therapy involved the use of γ-retroviral vectors such as Moloney Leukemia Virus (MLV) retrovirus with long terminal repeats (LTR) containing strong enhancer/promoters that can trigger distant enhancer activation (Hacein-Bey-Abina et al., J Clin Invest 118, 3132 (2008); Li et al., Science 296, 497 (2002)).
2. In contrast, the third-generation of lentivirus vectors, Self-inactivated (SIN)-lentivirus vectors (LV), with the deletions in their LTR, contain only one internal enhancer/promoter, which reduces the incidence of interactions with nearby cellular genes and thus decreases the risk of oncogenic integration (Modlich et al., Blood 108, 2545 (2006); Montini et al., J Clin Invest 119, 964 (2009)). Moreover, in contrast to the MLV, lentiviruses are not associated with oncogenesis. Importantly, leukemia is not a recognized side effect of HIV patients even though memory T cells are known to carry integrated virus for years.
3. SIN-LTR are also designed to prevent the possibility of developing replication competent lentivirus (RCL) during production of the viral supernatants. Indeed, transient transfection systems with three packaging plasmids are usually employed for vector production—gag, pol, and rev (Dull et al., J Virol 72, 8463 (1998)). A fourth plasmid containing the gene coding for the envelope and vesicular stomatitis virus glycoprotein (VSV-G) is frequently used as the choice of envelope. So far RCL has never been reported with this commonly used viral production system in patients after infusion of the vector transduced cell products (Sastry et al., Mol Ther 8, 830 (2003)).
4. LV efficiently transduce HSCs and do not alter their repopulation properties (Montini et al., J Clin Invest 119, 964 (2009); Gonzalez-Murillo et al., Blood 112, 3138 (2008)).
5. Clinical trials using SIN-LV to transduce human HSCs are being undertaken in the U.S. and Europe for several conditions including HIV-1, β-thalassemia, immune deficiencies and cancers (DiGiusto et al., Viruses 5, 2898 (2013); Drakopoulou et al., Current molecular medicine 13, 1314 (2013); Porter et al., N Engl J Med 365, 725 (2011); and Zhang et al., Gene Ther 20, 963

Figure 7:
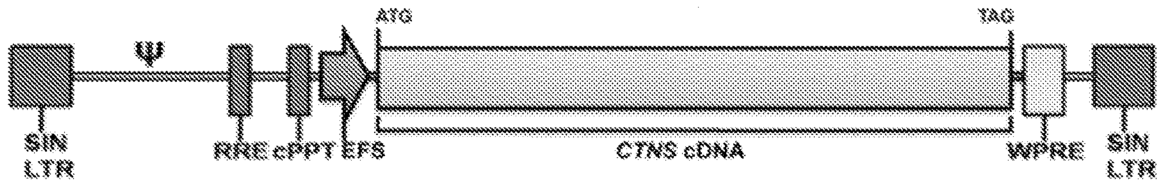
FIG. 7 is a pictorial diagram showing pCCL-CTNS lentivirus vector structure. SIN-LTR=Self-inactivating long terminal repeat; Ψ=Psi sequence; RRE=rev responsive element; cPPT=central polypurine tract; EFS=elongation factor la short; CTNS cDNA=human CTNS cDNA; WPRE=woodchuck hepatitis post-transcriptional regulatory element.

(2013)). For immune deficiency disorders, 35 patients have been transplanted with SIN-LV-modified HSCs so far (Bigger et al., Discovery medicine 17, 207 (2014)). A clinical trial using a SIN-LV to correct ex vivo HSCs in patients with X-adrenoleukodystrophy showed that cerebral demyelination was arrested in the two enrolled patients without further progression over 3 years of follow-up; and there was no evidence of clonal dominance (Cartier et al., Methods Enzymol 507, 187 (2012); Cartier et al., Science 326, 818 (2009)). Recently, a clinical trial for Wilskott-Aldrich was reported in three patients 32 months post-transplantation. Stable and long-term engraftment of the gene-modified HSCs (25-50%) resulted in improved platelet counts, protection from bleeding and infections, and resolution of eczema (Aiuti et al., Science 341, 1233151 (2013)). Another clinical success was recently reported in three presymptomatic patients with Metachromatic Leukodystrophy. Donor-derived blood cell engraftment of transduced cells achieved 45 to 80% and up to 24 months later the protein activity was reconstituted to above normal values in cerebrospinal fluid associated with a clear therapeutic benefit (Biffi et al., Science 341, 1233158 (2013)).

pCCL-CTNS lentiviral vector—a third-generation SIN-lentiviral vector in which human CTNS cDNA has been subcloned, pCCL-CTNS (FIG. 7), was prepared for use. The vector backbone pCCL-EFS-X-WPRE, described by Zufferey et al. (J Virol 72, 9873 (1998)), was provided by Dr. Donald Kohn (UCLA). A central polypurine tract (cPPT) fragment that increases the nuclear import of viral DNA was added to the CCL vector backbone (Demaison et al., Hum Gene Ther 13, 803 (2002)). A Woodchuck hepatitis virus Posttranslational Regulatory Element (WPRE) is present to boost titer and gene expression. However, its open-reading frame was eliminated (Zanta-Boussif et al., Gene Ther 16, 605 (2009)) because it overlapped with the woodchuck hepatitis virus X protein, a transcriptional activator involved in the development of liver tumors (Kingsman et al., Gene Ther 12, 3 (2005)). The transgene expression is driven by the ubiquitously expressed short intron-less human Elongation Factor 1 alpha promoter (EFS, 242 bp) (Wakabayashi-Ito, S. Nagata, J Biol Chem 269, 29831 (1994)). The EFS promoter, which lacks the intron and enhancers of the larger element used in many expression plasmids, has been shown to direct high level transcription of reporter genes in murine HSCs and to have significantly reduced trans-activation potential compared to γ-retroviral LTR (Zychlinski et al., Mol Ther, (2008)).

Vectors with this backbone are used in clinical trials conducted by Dr. Kohn: i) Autologous Transplantation of Bone Marrow CD34+ Stem/Progenitor Cells after Addition of a Normal Human ADA cDNA by the EFS-ADA Lentiviral Vector for Adenosine Deaminase (ADA)-Deficient Severe Combined Immunodeficiency (SCID) (BB IND 15440; NCT01852071); ii) Autologous Bone Marrow Stem Cells (CD34+) Cultured W/Cytokines; Transduced W/Self-inactivating (SIN) Lentiviral Vector Expressing Human β-globin (LENTI/BetaAS3-FB); following Busulfan (BB IND 16028; NCT02247843).

EXAMPLE 8

Preclinical Studies for Transplantation of pCCL-CTN-Transduced HSCs

Figure 8A:
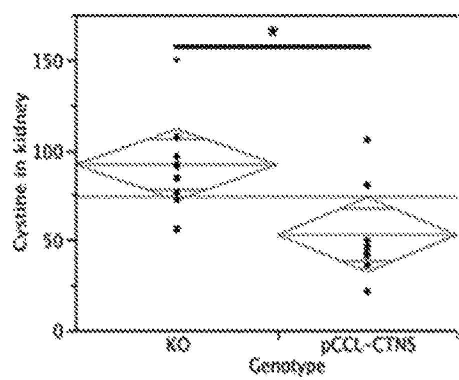
FIGS. 8A-8D are graphical and pictorial diagrams showing cystine and cystine crystal quantification in male kidney.

Sca1$^+$ HSCs isolated from Ctns$^{-/-}$ mice were transduced ex vivo with pCCL-CTNS using our optimized protocol for mHSCs and transplanted into 1 to 4 month old Ctns$^{-/-}$ mice. Cystine content in brain, eye, heart, kidney, liver, muscle, and spleen were analyzed after 4 (group 1; n=8) and 8 (group 2; n=12) months post-transplantation. As controls, age matched non-treated Ctns$^{-/-}$ mice (n=7 and n=12) were used or Ctns$^{-/-}$ mice transplanted with WT HSCs (n=4 and n=4). Decreases in cystine content were statistically significant in all the tissues tested in mice treated with pCCL-CTNS-transduced HSCs compared to Ctns$^{-/-}$ controls (FIG. 8A). The impact of Ctns$^{-/-}$ HSCs transduced with control vector, pCCL-GFP, was also tested on tissue cystine levels to exclude the possibility that the presence of any transgene results in cystine decreases. No decrease in any tissue was observed in mice transplanted with pCCL-GFP-Ctns$^{-/-}$ HSCs compared to non-treated Ctns$^{-/-}$ mice (Harrison et al., Mol Ther 21, 433 (2013)).

Figure 8B:
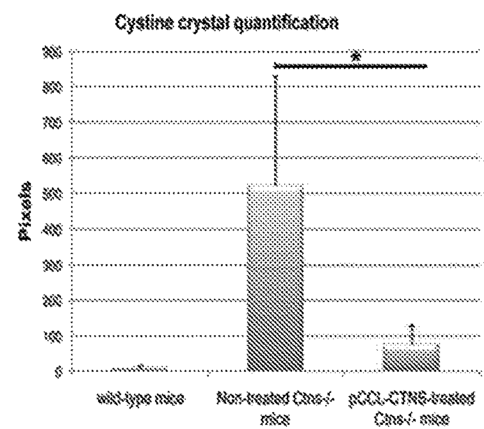
Figure 8C:
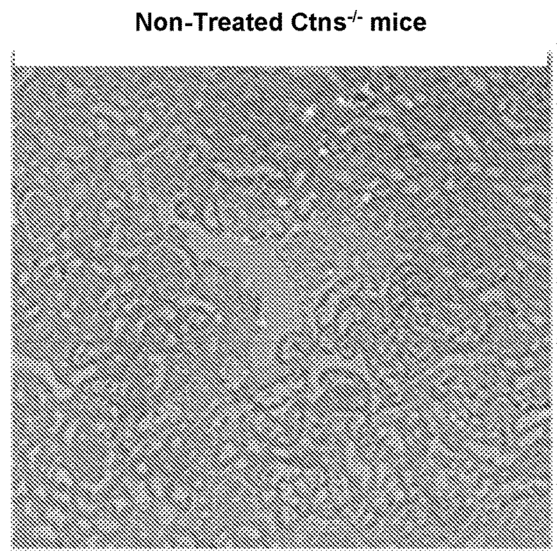
Figure 8D:
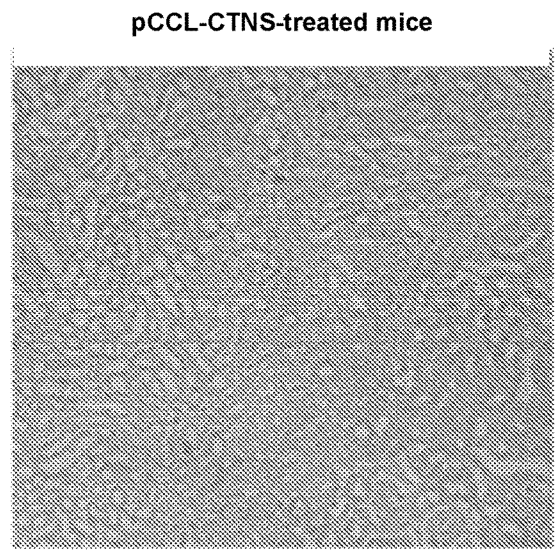

Renal glomerular and tubular function was assessed by measuring creatinine, urea, and phosphate levels in the serum, and creatinine clearance in 24-hour urine in males at 8 months post-transplant and compared to age-matched WT males (n=6). All the parameters were increased and the creatinine clearance decreased in non-treated Ctns$^{-/-}$ mice compared to WT mice. In the pCCL-CTNS-treated Ctns$^{-/-}$ mice, serum creatinine, urine phosphate and urine volume were significantly decreased compared to controls, showing a beneficial effect of the genetically modified HSC on kidney function in the Ctns$^{-/-}$ mice. Significant reduction of cystine crystals present in kidney sections was demonstrated in the treated Ctns$^{-/-}$ mice compared controls (FIGS. 8B and 8C). Note that we showed that cystine content in female kidneys was five times more elevated then in male kidney in Ctns$^{-/-}$ mice, thus studies on kidney have to be performed on males and females separately (Harrison et al., Mol Ther 21, 433 (2013)).

Quantitative PCR (qPCR) was performed on genomic DNA isolated from blood collected from pCCL-CTNS-transplanted Ctns$^{-/-}$ mice using lentiviral-specific primers to determine the Vector Copy Numbers per cell (VCN). Average VCN was 1.573±1.868, which fell in the targeted range of VCN 1-3. To determine if lentivirus levels could be predicted in tissues, linear regression analyses was performed between pCCL levels in the different tissues as a function of blood VCN levels. Direct correlation between the levels of lentivirus present in the blood and the levels present in tissues was demonstrated (Harrison et al., Mol Ther 21, 433 (2013)), which is useful to follow the future subjects enrolled in the clinical trial.

EXAMPLE 9

Pre-Clinical Pharmacology and Toxicology

The pharmacology/toxicology studies for HSCs ex-vivo gene-modified with pCCL-CTNS are performed using a batch of pCCL-CTNS lentiviral vector preparation produced under comparable-Good Manufacturing Practice (GMPc) obtained from the Indiana University Vector Production Facility (IUVPF), directed by Dr. Kenneth Cornetta. The targeted VCN range that was proposed to the FDA for safety is included between 1 and 3.

The In Vitro Immortalization (IVIM) assays, a genotoxicity test, was performed by the Translational Trials Development and Support Laboratory at the Cincinnati Children's Hospital Medical Center. This assay consists in mass culture expansion of transduced murine Lin—BMC for 2 weeks followed by culture in 96-well plates at a density of 100 or 10 cells/well for up to 7 weeks (Arumugam et al., Mol Ther 17, 1929 (2009); Modlich et al., Mol Ther 17, 1919 (2009)). The positive wells are counted and the frequency of replating cells calculated and compared to a negative (mock transduced) and positive control (MLV vector). The IVIM assays were performed in triplicates using GMPc pCCL-CTNS preparation with a VCN ranged between 1-3. No immortalized clone was produced with the construct, thus demonstrating an excellent safety profile.

Figure 9B:
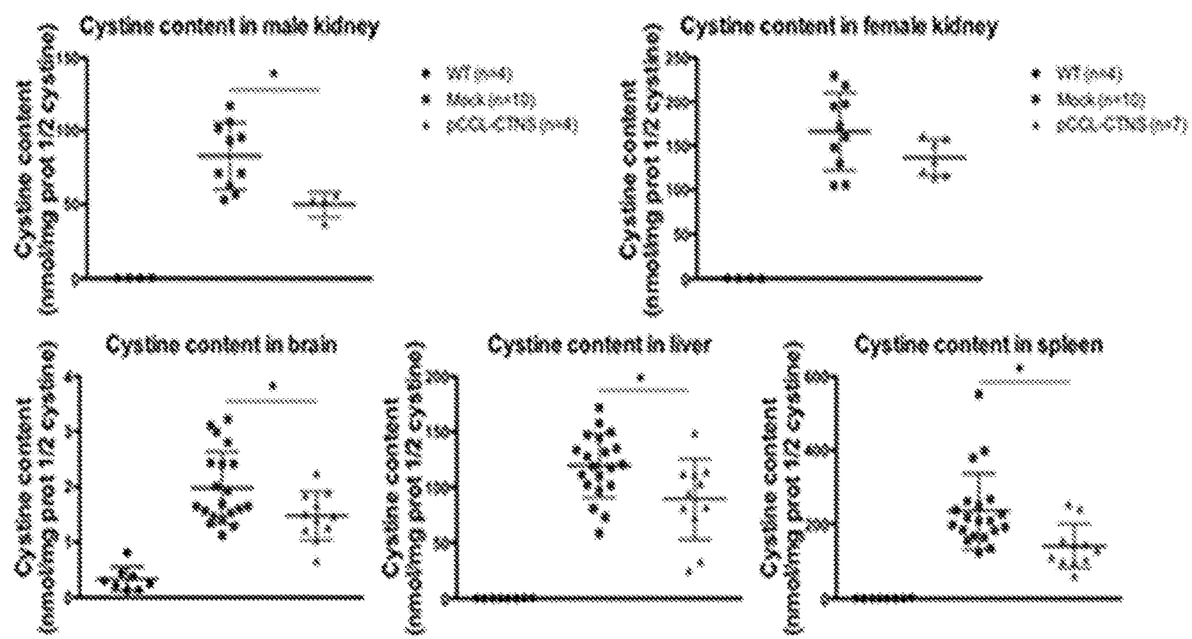

In vivo pharmacology/toxicology studies are currently being conducted with the analogous cell therapy product consisting in Sca1$^+$ mHSCs in the Ctns$^{-/-}$ mice involving serial transplantation. 15-20 Ctns$^{-/-}$ mice (10 males and 10 females) were transplanted with pCCL-CTNS-transduced Ctns mHSCs (with a VCN 1-3) and 20 with mock-transduced Ctns$^{-/-}$ mHSCs as Primary Recipients. Subsequently, bone marrow cells derived from each of these mice are transplanted into Secondary Ctns$^{-/-}$ mice. The Primary and Secondary mice have to be fully analyzed 6 months post-transplantation by comprehensive molecular, clinical and histological analyses. So far, we have 32 Primary Recipients that reached the 6-month time points: 11 Ctns$^{-/-}$ mice transplanted with pCCL-CTNS-transduced Ctns$^{-/-}$ mHSCs (with VCN included in 1-3) and 21 mock-treated mice, and 18 Secondary mice. No adverse event has been detected so far, the data show efficacy of the product as the weight of the mice treated with pCCL-CTNS-HSCs is higher and the cystine content in the tissues tested is significantly lower than the mock-treated controls (FIGS. 9A-9B). Thus, we have to reach the 6 month-time point for up to 9 additional Ctns$^{-/-}$ Primary Recipients treated with pCCL-CTNS-transduced HSCs and for 15 Secondary Recipients.

EXAMPLE 10

Manufacturing: Process Development

Using the GMPc pCCL-CTNS preparation, a protocol was optimized to transduce human CD34$^+$ HSCs from healthy donors to obtain a VCN included between 1 and 3. This protocol involved a one-hit vector transduction at a MOI 20 for 20 hours. Colony Forming Unit (CFU) assays were then performed using human CD34+ peripheral blood stem cell (PBSC) isolated from five healthy donors and four cystinotic patients and neither showed aberrant proliferation or differentiation potential with pCCL-CTNS LV compared to mock-transduced controls. Moreover, Vector Integration Site (VIS) analyses in the patient's cells showed no enrichment of the integration sites near proto-oncogene 5' ends. However, while this protocol led to an average VCN of 2 in healthy CD34+ cells, the average VCN in cystinosis patients was 0.96. Therefore, the protocol was further optimized with the cystinosis patients' cells to achieve a higher level of transduction as we have demonstrated that a higher level of cells expressing CTNS leads to a better therapeutic response (Yeagy et al., Kidney Int 79, 1198 (2011); Rocca et al., Investigative ophthalmology & visual science 56, 7214 (2015); Harrison et al., Mol Ther 21, 433 (2013)). This protocol involves a two-hit vector transduction at a MOI 20 each for 24-hour total and an average VCN of 1.9 with patients' cells was obtained. CFU assays and VIS have now to be repeated with this new protocol.

For the clinical trial, the transduction protocol is performed according to the GMP facility's standard operating procedures and uses the optimal protocol for cystinosis patients' CD34+ cells. Note that prior to enrolling the first patient, optimal conditions for large-scale transductions using the GMP-grade pCCL-CTNS vector preparation and optimal protocol are validated in small scales and Proficiency Runs using human CD34+ cells from healthy donors at the GMP facility. The clinical trial will include six patients affected with cystinosis, four adults and two adolescents. This will be a first-in-human clinical trial for an autologous stem cell and gene therapy treatment strategy for cystinosis. If successful, this treatment could be a life-long therapy that may eliminate or reduce renal deterioration and the need for kidney transplantation, as well as, the long-term complications associated with cystinosis. Additionally, the mechanism by which transplantation of pCCL-CTNS-modified CD34$^+$ HSCs provide beneficial and protective effects may be applicable to other inherited multi-organ degenerative disorders.

EXAMPLE 11

HSPC Transplantation for Danon Disease

The objective of this experiment is to determine whether Danon disease can be reduced by HSPC transplantation and to determine whether lysosomal cross-correction occurs. Using the mouse model described herein, it has been demonstrated that the hearts of Lamp2 KO mice exhibit increased numbers of abnormal mitochondria, and impairments in mitophagy and mitochondrial respiration, which is consistent with prior studies in induced pluripotent stem cell (hiPSC)-derived cardiac myocytes from Danon patients (Cherqui, *Kidney Int* 81, 127 (2012)), confirming similarities between the mouse model and human disease.

Figure 10D:
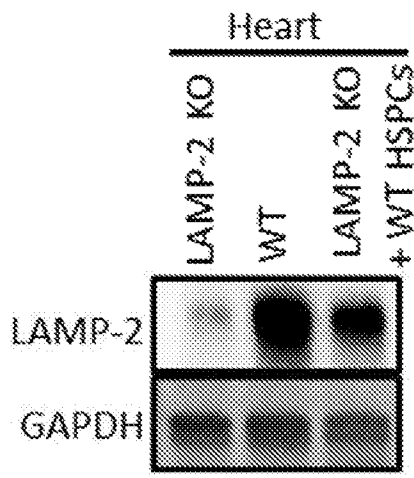
Figure 10E:
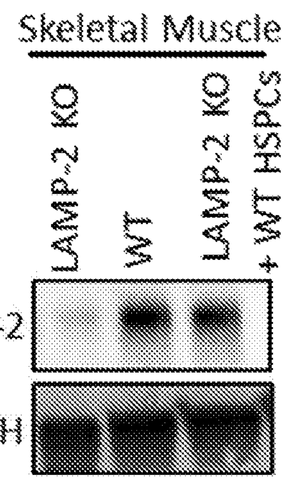
Figure 11:
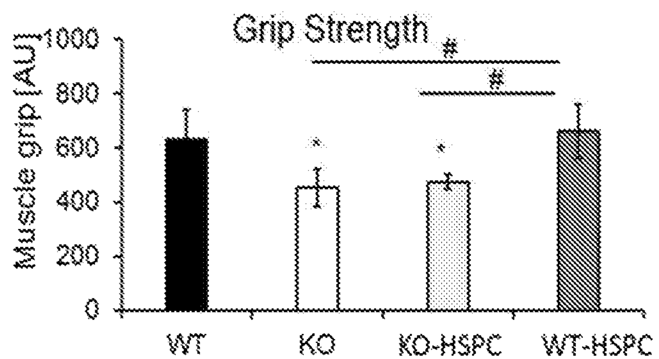
FIG. 11 is a graphical diagram showing the results of physiological assessment. Grip strength is rescued in mice recipients of WT-HSPC compared to KO (untreated) and KO-HSPC recipient mice. *p<0.05 vs. WT; #p<0.05 vs. WT-HSPC group.
Figure 12A:
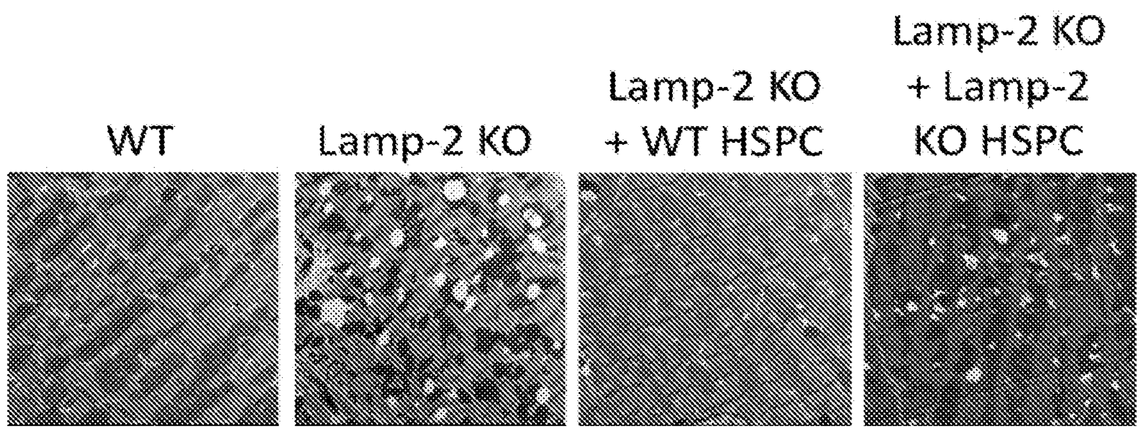
FIGS. 12A-12D are pictorial and graphical diagrams showing rescue of increased autophagic flux following WT BMT.
Figure 12B:
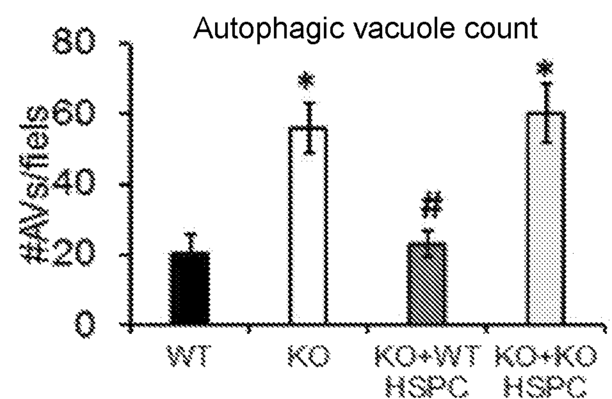
Figure 12C:
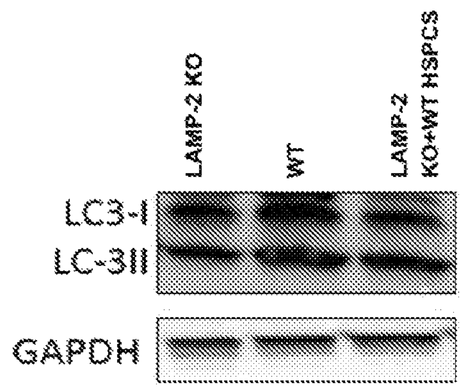
Figure 12D:
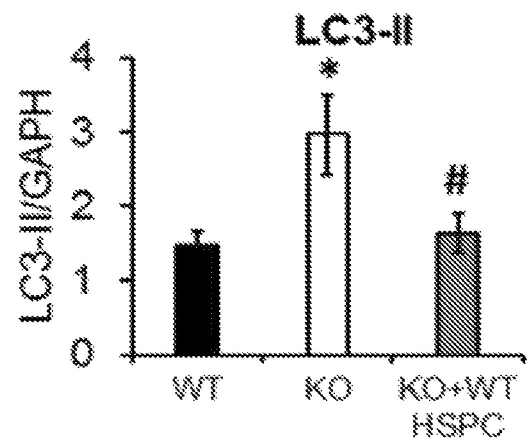

To evaluate the ability of WT HSPCs to rescue Danon disease, two month old lethally irradiated Lamp2 KO mice were transplanted with Sca1$^+$ HSPCs isolated from congenic C57BL/6 WT that ubiquitously expressed cytoplasmic eGFP (Tg(ACTB-EGFP)1Osb/J from Jackson Laboratory) (WT-HSPCs) using transplantation previously described protocols (Yeagy et al., Kidney Int 79, 1198 (2011); Naphade et al., Stem Cells 33, 301 (2015); Case et al., Proc Natl Acad Sci USA 96, 2988 (1999)). As negative controls, Lamp2 KO mice were also transplanted with Sca1$^+$ HSPCs from Lamp2 KO mice that constitutively expressed eGFP (KO-HSPCs). Skeletal muscle strength was assayed using previously described techniques and demonstrated significantly decreased grip strength in Lamp2 KO mice in comparison to both WT and Lamp2 mice that had received WT HSPCs (FIG. 11). LAMP2 protein expression, as assessed by Western blot analyses, was restored to near WT levels in hearts and skeletal muscle of Lamp2 KO mice transplanted with WT HSPCs (FIGS. 10D-10E).

To demonstrate that LAMP2 was expressed within cardiac myocytes of recipient Lamp2 KO mice, and not just within donor macrophages residing in those hearts, immunofluorescence studies were performed that demonstrated LAMP2$^+$ vesicles in cardiomyocytes ($\alpha$-actinin: white) located adjacent to donor macrophages (FIGS. 10A-10C). EM analyses showed decreased vacuoles in Lamp2 KO mice that received WT HSPCs in comparison to Lamp2 KO Mice (FIGS. 11A and 11B), exhibiting an appearance similar to that of WT mice. Improved autophagic flux following WT HSPC transplant of Lamp2 KO mice was confirmed by assessing LC3-II/GAPDH levels (FIGS. 11C-11D). In summary, these studies demonstrate the restoration of physiologic and metabolic function in Lamp2 KO mice treated with WT HSPC transplantation.

Although the invention has been described with reference to the above examples, it will be understood that modifications and variations are encompassed within the spirit and scope of the invention. Accordingly, the invention is limited only by the following claims.

What is claimed is:

1. A method of treating Danon disease in a subject comprising:

introducing a functional human lysosomal transmembrane gene into hematopoietic stem and progenitor cells (HSPCs) of the subject, wherein the gene encodes a LAMP-2 protein; and subsequently transplanting the HSPCs into the subject, wherein the step of introducing comprises contacting ex vivo the HSPCs with a lentiviral vector, thereby treating Danon disease.

2. The method of claim 1, wherein the LAMP-2 protein is a LAMP-2 isoform selected from the group consisting of LAMP-2A, LAMP-2B, and LAMP-2C.

3. The method of claim 1, wherein the subject is human.

4. The method of claim 1, wherein the lentiviral vector is a self-inactivating (SIN)-lentivirus vector.

5. The method of claim 1, wherein the HSPCs are isolated from the bone marrow of the subject.

6. A method of treating or ameliorating Danon disease in a subject comprising:

isolating hematopoietic stem and progenitor cells (HSPCs) from bone marrow from the subject;

introducing a LAMP-2 gene into the HSPCs, wherein the step of introducing is performed ex vivo; and transplanting the HSPCs back into the subject, wherein the step of introducing comprises contacting the HSPCs with a lentiviral vector, thereby treating or ameliorating the Danon disease.

7. The method of claim 6, wherein the HSPCs are CD34+ cells.

8. The method of claim 1 or 6, further comprising prior to the transplanting step exposing the subject to myeloablative drug.

9. The method of claim 8, wherein the myeloablative drugs are busulfan and cyclophosphamide.

10. The method of claim 1 or 6, wherein the lentiviral vector is a pCCL-LAMP2 vector.

* * * * *

UNITED STATES PATENT AND TRADEMARK OFFICE

CERTIFICATE OF CORRECTION

PATENT NO. : 11,806,367 B2
APPLICATION NO. : 16/493573
DATED : November 7, 2023
INVENTOR(S) : Stephanie Cherqui, Eric Adler and Sylvia Evans It is certified that error appears in the above-identified patent and that said Letters Patent is hereby corrected as shown below:

In the Claims

At Column 122, Line 50: replace “ameliorating the Danon Disease” with --ameliorating Danon Disease--

Signed and Sealed this
Eighth Day of October, 2024

Katherine Kelly Vidal

Katherine Kelly Vidal
*Director of the United States Patent and Trademark Office*